US007241742B2

(12) United States Patent
Aziz et al.

(10) Patent No.: US 7,241,742 B2
(45) Date of Patent: Jul. 10, 2007

(54) CYP1B1 NUCLEIC ACIDS AND METHODS OF USE

(75) Inventors: Nazneen Aziz, Lexington, MA (US); Mary Lynne Hedley, Lexington, MA (US); Robert G. Urban, Lexington, MA (US); Andrew J. Tomlinson, Wayland, MA (US); Geoffrey Cole, Malden, MA (US)

(73) Assignee: MGI PHARMA Biologics, Inc., Lexington, MA (US)

( * ) Notice: Subject to any disclaimer, the term of this patent is extended or adjusted under 35 U.S.C. 154(b) by 343 days.

(21) Appl. No.: 09/999,686

(22) Filed: Oct. 31, 2001

(65) Prior Publication Data

US 2003/0028000 A1 Feb. 6, 2003

Related U.S. Application Data

(60) Provisional application No. 60/298,428, filed on Jun. 15, 2001, provisional application No. 60/261,719, filed on Jan. 12, 2001, provisional application No. 60/244,501, filed on Oct. 31, 2000.

(51) Int. Cl.

| | |
|---|---|
| ***A01N 43/04*** | (2006.01) |
| ***A01N 63/00*** | (2006.01) |
| ***A61K 38/43*** | (2006.01) |
| ***C07H 21/04*** | (2006.01) |
| *C12P 21/06* | (2006.01) |
| *C12N 15/09* | (2006.01) |
| *C12N 15/12* | (2006.01) |
| *C12N 12/52* | (2006.01) |

(52) U.S. Cl. .................... 514/44; 424/93.2; 424/93.21; 424/94.1; 435/69.1; 435/69.3; 435/320.1; 435/440; 536/23.1; 536/23.2

(58) Field of Classification Search ................. 435/7.1, 435/7.23, 7.4, 320.1; 514/44; 536/23.1, 536/23.5

See application file for complete search history.

(56) References Cited

U.S. PATENT DOCUMENTS

| | | | | |
|---|---|---|---|---|
| 5,539,084 | A | * | 7/1996 | Geysen |
| 5,679,647 | A | * | 10/1997 | Carson et al. |
| 5,783,567 | A | * | 7/1998 | Hedley et al. |
| 5,807,978 | A | * | 9/1998 | Kokolus et al. |
| 5,840,839 | A | * | 11/1998 | Wang et al. |
| 6,130,077 | A | | 10/2000 | Yue et al. |
| 6,242,203 | B1 | | 6/2001 | Melvin et al. |

FOREIGN PATENT DOCUMENTS

| | | |
|---|---|---|
| WO | WO 95/05849 A1 | 3/1995 |
| WO | WO 97/12246 | 4/1997 |
| WO | WO 98/36098 | 8/1998 |
| WO | WO 00/56773 A1 | 9/2000 |
| WO | WO 01/35810 A2 | 5/2001 |
| WO | WO 01/58444 A1 | 8/2001 |
| WO | WO 01/79468 A2 | 10/2001 |

OTHER PUBLICATIONS

Tuting et al. Journal of Molecular Medicine, 75:478-491, 1997.*
Reiger et al. Glossary of Genetics and Cytogenetics, Classical and Molecular, 4th Ed., Springer-Verlay, Berlin, 1976.*
Riott et al. Immunology, Fourth Edition, 1996, Mosby, p. 7.9-7.11.*
Sonenberg et al. Cell, 27:563-572, 1981.*
Lawrence et al. Journal of Clinical Investigation, 102(6):1258-1264, 1998.*
Crystal R. G. Science, 270(5235):404-409, Oct. 20, 1995.*
Walther et al. Drugs. 60(2):249-271, Aug. 2000.*
Vile et al. Gene Therapy, (7):2-8, 2000.*
Rochlitz C. F. Swiss Medicine Weekly, 131:4-9, 2001.*
Verma et al. Nature, vol. 389, pp. 239-242, 1997.*
Lunsford et al. Journal of Drug Targeting, 8(1):39-50, Apr. 2000.*
Luby et al. Clinical Immunology, 112(1):45-53, 2004.*
Gregoriadis G. Current Opinion in Molecular Therapy, 1(1):39-42, Feb. 1999.*
Murray et al. Cancer Research, 57:3026-3031, Jul. 15, 1997.*
Albin et al., "Main Drug-metabolizing Enzyme Systems in Human Breast Tumors and Peritumoral Tissues," Cancer Research, 53:3541-3546, Aug. 1, 1993.
Aziz & Munro, "Iron regulates ferritin MRNA translation through a segment of its 5' untranslated region," Proc. Natl. Acad. Sci. USA, 84:8478-8482, Dec. 1987.
Benton & Kennedy, "DNA vaccine strategies for the treatment of cancer," Curr. Top. Microbiol. Immunol., 226:1-20, 1998.
Buchmann et al., "Development of Cytochrome P-450-altered Preneoplastic and Neoplastic Lesions during Nitrosamine-induced Hepatocarcinogenesis in the Rat," Cancer Research, 47:2911-2918, Jun. 1, 1987.
Czerwinski et al., "Quantification of CYP2B7, CYP4B1, and CYPOR Messenger RNAs in Normal Human Lung and Lung Tumors," Cancer Research, 54:1085-1091, Feb. 15, 1994.
Dela Cruz et al., "Xenogeneic and allogeneic anti-MHC immune responses induced by plasmid DNA immunization," Vaccine, 17:2479-2492, 1999.
Duenas et al., "In vitro immunization of naive human B cells yields high affinity immunoglobulin B antibodies as illustrated by phase display," Immunol., 89:1-7, 1996.
Gagliardi et al., "Presentation of peptides by cultured monocytes or activated T cells allows specific priming of human cytotoxic T-lymphocytes," Internat. Immunol., 7(11):1741-1752, 1995.

(Continued)

*Primary Examiner*—David J. Blanchard
(74) *Attorney, Agent, or Firm*—Fish & Richardson P.C.

(57) ABSTRACT

The present invention provides nucleic acids containing transcriptional units that encode CYP1B1 polypeptides or portions thereof, wherein the transcriptional units lack sequences found in the untranslated region (UTR) of naturally occurring forms of the CYP1B1 transcript. The nucleic acids of the invention lack translational repressor elements and thus provide for a system of enhanced translation of the CYP1B1 polypeptide or portions thereof. Also disclosed are methods of administering nucleic acids to a mammal and use in the treatment of proliferative disorders or cancer.

22 Claims, 12 Drawing Sheets

OTHER PUBLICATIONS

Hanke et al., "DNA multi-CTL epitope vaccines for HIV and Plasmodium falciparum: Immunogenocity in mice vaccine," 16:436-435, 1998.
Jansson et al., "Enhanced expression of CYP1B1 in *Escherichia coli*," Toxicology, 144:211-219, 2000.
Knuth et al., "Cancer immunotheraphy in clinical oncology," Cancer Chemother Pharmacol., 46(Suppl)S46-S51, 2000.
McFadyen et al., "Immunohistochemical Localization of Cytochrome P450 CYP1B1 in Breast Cancer with Monoclonal Antibodies Specific for CYP1B1," J. Histochemistry & Cytochemistry, 47(11):1457-1464, 1999.
McKay et al., "Expression of cytochrome P450 CYP1B1 in breast cancer," FEBS Letters, 374:270-272, 1995.
Minnerath et al., "The BALB/c mouse B-cell response to pigeon cytochrome *c* initiates as a heteroclitic response specific for the self antigen mouse cytochrome *c*, " Immunology, 92:12379-12383, Dec. 1995.
Murray et al., "Cytochrome P450 expression is a common molecular event in soft tissue sarcomas," J. Pathol., 171:49-52, 1993.
Murray et al., "Tumor-specific expression of cytochrome P450 CYP1B1," Cancer Research, 57:3026-31, Jul. 15, 1997.
Ribas et al., "Generation of T-Cell Immunity to a Murine Melanoma Using MART-1-Engineered Dendritic Cells," Journal of Immunotherapy, 23(1):59-66, 2000.
Sarfarazi, "Recent advances in molecular genetics of glaucomas," Human Molecular Genetics, 6(10):1667-1677, 1997.
Shimada et al., Recombinant Human Cytochrome P450 1B1 Expression in *Escherichia coli*, Archives of Biochemistry and Biophysics, 357(1):111-120, Sep. 1, 1998.
Spooner et al., "DNA vaccination for cancer treatment," Gene Therapy, 2:173-180, 1995.
Steitz et al., "Genetic Immunization of Mice with Human Tyrosinase-related Protein 2: Implications for the Immunotherapy of Melanoma," Int. J. Cancer, 86:89-94, 2000.
Stevenson, "DNA vaccines against cancer: from genes to therapy," Ann. Oncol., 10:1413-1418, 1999.
Stoilov et al., "Identification of three different runcating mutations in cytochrome P4501B1 (*CYP1B1*) as the principal cause of primary congenital glaucoma (buphthalmos) in families linked to the GLC3A locus on chromosome 2p21," Human Molecular Genetics, 6(4):641-647, 1997.
Sutter et al., "Complete cDNA sequence of a human-dioxin inducible mRNA identifies a new gene subfamily of cytochrome p450 that maps to chromosome 2," J. Biol. Chem., 269(18):13092-13099, 1994.
Tang et al., "Isolation and Characterization of the Human Cytochrome *P450 CYP1B1* Gene," J. Biological Chemistry, 271(45):28324-28330, Nov. 8, 1996.
Taylor et al., "Cytochrome P450 IBI expression in human malignant tumors," Biochem. Society Transactions, 24:328S, 1996.
Weber et al., "Tumor immunity and autoimmunity induced by immunization with homologous DNA," J. Clin. Invest., 102(6):1258-1264, Sep. 1998.
Xiang et al., "An autologous oral DNA vaccine protects against murine melanoma," Proc. Natl. Acad. Sci., 97(10):5492-5497, May 9, 2000.
Zhang et al., "Characterization of the Mouse *Cyp1B1* Gene," J. Biological Chemistry, 273(9):5174-5183, Feb. 27, 1998.
Zhou et al., "Protective immunization against melanoma by gp100 DNA-HVJ-liposome vaccine," Gene Therapy, 6:1768-1773, 1999.
Zuber et al., "Induction of Immune Responses and Break of Tolerance by DNA against the HIV-1 Coreceptor CCR5 but No Protection from SIVsm Challenge," Virology, 278:400-411, 2000.
GenBank™ Accession No. U03688, Jul. 6, 1994.
Shehin et al., "Transcriptional Regulation of the Human *CYP*1B1 Gene; Evidence for Involvement of an Aryl Hydrocarbon Receptor Response Element in Constitutive Expression", *The Journal of Biological Chemistry*, 275 (10): 6770-6776 (2000).

* cited by examiner

```
actctggagt gggagtggga gtgggagcga gcgcttctgc gactccagtt gtgagagccg    60
caagggcatg ggaattgacg ccactcaccg acccccagtc tcaatctcaa cgctgtgagg   120
aaacctcgac tttgccaggt ccccaagggc agcggggctc ggcgagcgag gcacccttct   180
ccgtccccat cccaatccaa gcgctcctgg cactgacgac gccaagagac tcgagtggga   240
gttaaagctt ccagtgaggg cagcaggtgt ccaggccggg cctgcgggtt cctgttgacg   300
tcttgcccta ggcaaaggtc ccagttcctt ctcggagccg gctgtcccgc gccactggaa   360
accgcacctc cccgcagc atg ggc acc agc ctc agc ccg aac gac cct tgg     411
                    Met Gly Thr Ser Leu Ser Pro Asn Asp Pro Trp
                    1               5                   10

ccg cta aac ccg ctg tcc atc cag cag acc acg ctc ctg cta ctc ctg     459
Pro Leu Asn Pro Leu Ser Ile Gln Gln Thr Thr Leu Leu Leu Leu Leu
            15                  20                  25

tcg gtg ctg gcc act gtg cat gtg ggc cag cgg ctg ctg agg caa cgg     507
Ser Val Leu Ala Thr Val His Val Gly Gln Arg Leu Leu Arg Gln Arg
        30                  35                  40

agg cgg cag ctc cgg tcc gcg ccc ccg ggc ccg ttt gcg tgg cca ctg     555
Arg Arg Gln Leu Arg Ser Ala Pro Pro Gly Pro Phe Ala Trp Pro Leu
    45                  50                  55

atc gga aac gcg gcg gcg gtg ggc cag gcg gct cac ctc tcg ttc gct     603
Ile Gly Asn Ala Ala Ala Val Gly Gln Ala Ala His Leu Ser Phe Ala
60                  65                  70                  75

cgc ctg gcg cgg cgc tac ggc gac gtt ttc cag atc cgc ctg ggc agc     651
Arg Leu Ala Arg Arg Tyr Gly Asp Val Phe Gln Ile Arg Leu Gly Ser
                80                  85                  90

tgc ccc ata gtg gtg ctg aat ggc gag cgc gcc atc cac cag gcc ctg     699
Cys Pro Ile Val Val Leu Asn Gly Glu Arg Ala Ile His Gln Ala Leu
            95                  100                 105

gtg cag cag ggc tcg gcc ttc gcc gac cgg ccg gcc ttc gcc tcc ttc     747
Val Gln Gln Gly Ser Ala Phe Ala Asp Arg Pro Ala Phe Ala Ser Phe
        110                 115                 120

cgt gtg gtg tcc ggc ggc cgc agc atg gct ttc ggc cac tac tcg gag     795
Arg Val Val Ser Gly Gly Arg Ser Met Ala Phe Gly His Tyr Ser Glu
    125                 130                 135

cac tgg aag gtg cag cgg cgc gca gcc cac agc atg atg cgc aac ttc     843
His Trp Lys Val Gln Arg Arg Ala Ala His Ser Met Met Arg Asn Phe
140                 145                 150                 155

ttc acg cgc cag ccg cgc agc cgc caa gtc ctc gag ggc cac gtg ctg     891
Phe Thr Arg Gln Pro Arg Ser Arg Gln Val Leu Glu Gly His Val Leu
                160                 165                 170

agc gag gcg cgc gag ctg gtg gcg ctg ctg gtg cgc ggc agc gcg gac     939
Ser Glu Ala Arg Glu Leu Val Ala Leu Leu Val Arg Gly Ser Ala Asp
            175                 180                 185
```

Figure 1A

```
ggc gcc ttc ctc gac ccg agg ccg ctg acc gtc gtg gcc gtg gcc aac      987
Gly Ala Phe Leu Asp Pro Arg Pro Leu Thr Val Val Ala Val Ala Asn
        190                 195                 200

gtc atg agt gcc gtg tgt ttc ggc tgc cgc tac agc cac gac gac ccc     1035
Val Met Ser Ala Val Cys Phe Gly Cys Arg Tyr Ser His Asp Asp Pro
    205                 210                 215

gag ttc cgt gag ctg ctc agc cac aac gaa gag ttc ggg cgc acg gtg     1083
Glu Phe Arg Glu Leu Leu Ser His Asn Glu Glu Phe Gly Arg Thr Val
220                 225                 230                 235

ggc gcg ggc agc ctg gtg gac gtg atg ccc tgg ctg cag tac ttc ccc     1131
Gly Ala Gly Ser Leu Val Asp Val Met Pro Trp Leu Gln Tyr Phe Pro
                240                 245                 250

aac ccg gtg cgc acc gtt ttc cgc gaa ttc gag cag ctc aac cgc aac     1179
Asn Pro Val Arg Thr Val Phe Arg Glu Phe Glu Gln Leu Asn Arg Asn
            255                 260                 265

ttc agc aac ttc atc ctg gac aag ttc ttg agg cac tgc gaa agc ctt     1227
Phe Ser Asn Phe Ile Leu Asp Lys Phe Leu Arg His Cys Glu Ser Leu
        270                 275                 280

cgg ccc ggg gcc gcc ccc cgc gac atg atg gac gcc ttt atc ctc tct     1275
Arg Pro Gly Ala Ala Pro Arg Asp Met Met Asp Ala Phe Ile Leu Ser
    285                 290                 295

gcg gaa aag aag gcg gcc ggg gac tcg cac ggt ggt ggc gcg cgg ctg     1323
Ala Glu Lys Lys Ala Ala Gly Asp Ser His Gly Gly Gly Ala Arg Leu
300                 305                 310                 315

gat ttg gag aac gta ccg gcc act atc act gac atc ttc ggc gcc agc     1371
Asp Leu Glu Asn Val Pro Ala Thr Ile Thr Asp Ile Phe Gly Ala Ser
                320                 325                 330

cag gac acc ctg tcc acc gcg ctg cag tgg ctg ctc ctc ctc ttc acc     1419
Gln Asp Thr Leu Ser Thr Ala Leu Gln Trp Leu Leu Leu Leu Phe Thr
            335                 340                 345

agg tat cct gat gtg cag act cga gtg cag gca gaa ttg gat cag gtc     1467
Arg Tyr Pro Asp Val Gln Thr Arg Val Gln Ala Glu Leu Asp Gln Val
        350                 355                 360

gtg ggg agg gac cgt ctg cct tgt atg ggt gac cag ccc aac ctg ccc     1515
Val Gly Arg Asp Arg Leu Pro Cys Met Gly Asp Gln Pro Asn Leu Pro
    365                 370                 375

tat gtc ctg gcc ttc ctt tat gaa gcc atg cgc ttc tcc agc ttt gtg     1563
Tyr Val Leu Ala Phe Leu Tyr Glu Ala Met Arg Phe Ser Ser Phe Val
380                 385                 390                 395
```

Figure 1B

```
cct gtc act att cct cat gcc acc act gcc aac acc tct gtc ttg ggc      1611
Pro Val Thr Ile Pro His Ala Thr Thr Ala Asn Thr Ser Val Leu Gly
                400                 405                 410

tac cac att ccc aag gac act gtg gtt ttt gtc aac cag tgg tct gtg      1659
Tyr His Ile Pro Lys Asp Thr Val Val Phe Val Asn Gln Trp Ser Val
            415                 420                 425

aat cat gac cca gtg aag tgg cct aac ccg gag aac ttt gat cca gct      1707
Asn His Asp Pro Val Lys Trp Pro Asn Pro Glu Asn Phe Asp Pro Ala
        430                 435                 440

cga ttc ttg gac aag gat ggc ctc atc aac aag gac ctg acc agc aga      1755
Arg Phe Leu Asp Lys Asp Gly Leu Ile Asn Lys Asp Leu Thr Ser Arg
    445                 450                 455

gtg atg att ttt tca gtg ggc aaa agg cgg tgc att ggc gaa gaa ctt      1803
Val Met Ile Phe Ser Val Gly Lys Arg Arg Cys Ile Gly Glu Glu Leu
460                 465                 470                 475

tct aag atg cag ctt ttt ctc ttc atc tcc atc ctg gct cac cag tgc      1851
Ser Lys Met Gln Leu Phe Leu Phe Ile Ser Ile Leu Ala His Gln Cys
                480                 485                 490

gat ttc agg gcc aac cca aat gag cct gcg aaa atg aat ttc agt tat      1899
Asp Phe Arg Ala Asn Pro Asn Glu Pro Ala Lys Met Asn Phe Ser Tyr
            495                 500                 505

ggt cta acc att aaa ccc aag tca ttt aaa gtc aat gtc act ctc aga      1947
Gly Leu Thr Ile Lys Pro Lys Ser Phe Lys Val Asn Val Thr Leu Arg
        510                 515                 520

gag tcc atg gag ctc ctt gat agt gct gtc caa aat tta caa gcc aag      1995
Glu Ser Met Glu Leu Leu Asp Ser Ala Val Gln Asn Leu Gln Ala Lys
    525                 530                 535

gaa act tgc caa taa gaagcaagag gcaagctgaa atttagaaa tattcacatc      2050
Glu Thr Cys Gln  *
540

ttcggagatg aggagtaaaa ttcagttttt ttccagttcc tcttttgtgc tgcttctcaa   2110
ttagcgttta aggtgagcat aaatcaactg tccatcaggt gaggtgtgct ccatacccag   2170
cggttcttca tgagtagtgg gctatgcagg agcttctggg agattttttt gagtcaaaga   2230
cttaaagggc ccaatgaatt attatataca tactgcatct tggttatttc tgaaggtagc   2290
attctttgga gttaaaatgc acatatagac acatacaccc aaacacttac accaaactac   2350
tgaatgaaga agtattttgg taaccaggcc atttttggtg ggaatccaag attggtctcc   2410
catatgcaga aatagacaaa aagtatatta aacaaagttt cagagtatat tgttgaagag   2470
acagagacaa gtaatttcag tgtaaagtgt gtgattgaag gtgataaggg aaaagataaa   2530
gaccagaaat tccctttca cctttttcagg aaaataactt agactctagt atttatgggt   2590
ggatttatcc ttttgccttc tgctatactt ccttactttt aaggataaat cataaagtca   2650
gttgctcaaa aagaaatcaa tagttgaatt agtgagtata gtgggttcc atgagttatc   2710
atgaatttta aagtatgcat tattaaattg taaaactcca aggtgatgtt gtacctcttt   2770
```

Figure 1C

```
tgcttgccaa agtacagaat ttgaattatc agcaaagaaa aaaaaaaaag ccagccaagc   2830
tttaaattat gtgaccataa tgtactgatt tcagtaagtc tcataggtta aaaaaaaaag   2890
tcaccaaata gtgtgaaata tattacttaa ctgtccgtaa gcagtatatt agtattatct   2950
tgttcaggaa aaggttgaat aatatatgcc ttgtgtaata ttgaaaattg aaaagtacaa   3010
ctaacgcaac caagtgtgct aaaaatgagc ttgattaaat caaccaccta tttttgacat   3070
ggaaatgaag cagggtttct tttcttcact caaattttgg cgaatctcaa aattagatcc   3130
taagatgtgt tcttattttt ataacatctt tattgaaatt ctatttataa tacagaatct   3190
tgttttgaaa ataacctaat taatatatta aaattccaaa ttcatggcat gcttaaattt   3250
taactaaatt ttaaagccat tctgattatt gagttccagt tgaagttagt ggaaatctga   3310
acattctcct gtggaaggca gagaaatcta agctgtgtct gcccaatgaa taatggaaaa   3370
tgccatgaat tacctggatg ttctttttac gaggtgacaa gagttgcgga cagaactccc   3430
attacaactg accaagtttc tcttctagat gatttttgga aagttaacat taatgcctgc   3490
tttttggaaa gtcagaatca gaagatagtc ttggaagctg tttggaaaag acagtggaga   3550
tgaggtcagt tgtgtttttt aagatggcaa ttactttggt agctgggaaa gcataaagct   3610
caaatgaaat gtatgcattc acatttagaa aagtgaattg aagtttcaag ttttaaagtt   3670
cattgcaatt aaacttccaa agaaagttct acagtgtcct aagtgctaag tgcttattac   3730
attttattaa gctttttgga atctttgtac caaaatttta aaaaagggag tttttgatag   3790
ttgtgtgtat gtgtgtgtgg ggtcggggga tgctaagaga aaagagagaa acactgaaaa   3850
gaaggaaaga tggttaaaca ttttcccact cattctgaat taattaattt ggagcacaaa   3910
attcaaagca tggacattta gaagaaagat gtttggcgta gcagagttaa atctcaaata   3970
ggctattaaa aaagtctaca acatagcaga tctgttttgt ggtttggaat attaaaaaac   4030
ttcatgtaat tttattttaa aatttcatag ctgtacttct tgaatataaa aaatcatgcc   4090
agtattttta aaggcattag agtcaactac acaaagcagg cttgcccagt acatttaaat   4150
tttttggcac ttgccattcc aaaatattat gccccaccaa ggctgagaca gtgaatttgg   4210
gctgctgtag cctatttttt tagattgaga aatgtgtagc tgcaaaaata atcatgaacc   4270
aatctggatg cctcattatg tcaaccaggt ccagatgtgc tataatctgt ttttacgtat   4330
gtaggcccag tcgtcatcag atgcttgcgg caaaagaaag ctgtgtttat atggaagaaa   4390
gtaaggtgct tggagtttac ctggcttatt taatatgctt ataacctagt taaagaaagg   4450
aaaagaaaac aaaaaacgaa tgaaaataac tgaatttgga ggctggagta atcagattac   4510
tgctttaatc agaaaccctc attgtgtttc taccggagag agaatgtatt tgctgacaac   4570
cattaaagtc agaagtttta ctccaggtta ttgcaataaa gtataatgtt tattaaatgc   4630
ttcatttgta tgtcaaagct ttgactctat aagcaaattg ctttttttcca aaacaaaaag   4690
atgtctcagg tttgttttgt gaattttcta aaagctttca tgtcccagaa cttagccttt   4750
acctgtgaag tgttactaca gccttaatat tttcctagta gatctatatt agatcaaata   4810
gttgcatagc agtatatgtt aatttgtgtg tttttagctg tgacacaact gtgtgattaa   4870
aaggtatact ttagtagaca tttataactc aaggatacct tcttatttaa tcttttctta   4930
ttttgtactt ttatcatgaa tgcttttagt gtgtgcataa tagctacagt gcatagttgt   4990
agacaaagta cattctgggg aaacaacatt tatatgtagc ctttactgtt tgatatacca   5050
aattaaaaaa aaattgtatc tcattactta tactggaca ccattaccaa aataataaaa   5110
atcactttca taatcttgaa aaaa
```

Figure 1D

CYP1B1 NUCLEIC ACIDS AND METHODS OF USE

CROSS REFERENCE TO RELATED APPLICATIONS

This application claims priority from U.S. Provisional Application No. 60/244,501, filed Oct. 31, 2000, U.S. Provisional Application No. 60/261,719, filed Jan. 12, 2001, and U.S. Provisional Application No. 60/298,428, filed Jun. 15, 2001. These applications are incorporated herein by reference in their entirety.

FIELD OF THE INVENTION

The invention relates to CYP1B1 nucleic acids and methods of use to induce an immune response.

BACKGROUND OF THE INVENTION

Cytochrome P450 constitutes a large gene family of enzymes that participate in the oxidative activation and/or deactivation of a wide range of xenobiotics, including many potential carcinogens and several anticancer drugs (Guengerich and Shimada (1991) Chem. Res. Toxicol. 4:931; Gonzalez and Gelboin (1994) Drug Metab. Rev. 26:165; Kivisto et al. (1995) Br. J. Clin. Pharmacol. 40:523).

The human CYP1 gene family, one of the major P450 families, consists of three individual forms classified into two sub-families. CYP1B1, a member of one sub-family, is 543 amino acids in length. It is structurally distinct from the two members of the CYP1A2 subfamily (Tang et al., J. Biol. Chem. (1996) 271:28324).

Studies of various types of cancer, including breast cancer, esophageal cancer and soft tissue sarcomas, have shown that there may be tumor-specific expression of a CYP1B1 form of P450 (see Murray et al. (1991) Br. J. Cancer 63:1021; Murray et al. (1993) J. Pathol. 171:49; Murray et al. (1994) Gut 35:599). Immunohistochemistry studies of CYP1B1 show a strong immunoreactivity for several different types of tumors (bladder, breast, colon, kidney, lung, esophagus, ovary, skin, stomach, uterus, bone and connective tissue, lymph node, brain, and testis) (see WO 97/12246, herein incorporated by reference).

SUMMARY OF THE INVENTION

The invention is based on the discovery that nucleic acids can be constructed that contain transcriptional units that encode CYP1B1 polypeptides or portions thereof, wherein the transcriptional units lack translational repressor elements. These elements may be located in the untranslated region (UTR) of naturally occurring forms of the CYP1B1 transcript, or in the coding sequence, or both. The nucleic acids of the invention lack some or all of the CYP1B1 endogenous translational repressor elements and thus provide for a system of enhanced translation of the CYP1B1 polypeptide or portions thereof. The nucleic acids of the invention can also contain mutations, deletions, insertions, or rearrangements that promote the immunogenicity of the encoded protein. The polypeptides encoded by the nucleic acids described herein are useful for stimulating an immune response in a mammal.

In one aspect, the invention features a nucleic acid including a transcriptional unit that contains a coding sequence that encodes a polypeptide containing CYP1B1 or a portion thereof that contains a peptide that binds to an MHC class I or class II molecule or is a B cell epitope. The transcriptional unit does not contain a translational repressor element operably linked to the coding sequence.

As used herein, a "transcriptional unit" refers to a nucleic acid containing a translation start signal, followed by an open reading frame optionally including an intron and appropriate splice donor and acceptor sites, followed by a termination codon, wherein the nucleic acid is either (1) an RNA or (2) a sequence of nucleotides that is transcribed into an RNA. A "translation start signal" refers to an initiation codon in the context of a Kozak consensus sequence. A "translational repressor element" refers to a nucleotide sequence located in the untranslated region of a transcript that, when present, decreases the level of translation of a polypeptide encoded by the transcript by at least 25% relative to the transcript lacking the nucleotide sequence. A translational repressor element can cause a decreased level of translation by, for example, preventing ribosome binding to a transcript or decreasing the half life of a transcript.

A polypeptide encoded by a nucleic acid described herein contains a segment of CYP1B1 that is at least eight amino acids in length. In one example, the polypeptide contains the sequence FLDPRPLTV (SEQ ID NO:22). In another example, the polypeptide contains the sequence of any of SEQ ID Nos:31–39. In another example, the polypeptide is less than 400, 300, 200 or 100 amino acids in length.

As used herein, a "segment" is an amino acid sequence which (a) corresponds to the sequence of a portion (i.e., fragment less than all) of a CYP1B1 protein and (b) contains one or more epitopes. For clarity, the term "segment" is used herein to denote a part of a polypeptide encoded by a nucleic acid of the invention, while the term "portion" is used to denote the corresponding part of the naturally occurring protein. By "epitope" is meant a peptide which binds to the binding groove of an MHC class I or class II molecule or to the antigen-binding region of an antibody. A methionine codon can be included at the 5' end of this or any other coding sequence of the invention, to facilitate translation. In addition, a polypeptide encoded by a nucleic acid described herein can encode a targeting signal, as described in more detail below.

A transcriptional unit described herein can contain an RNA stabilization sequence. "RNA stabilization sequence" refers to a nucleotide sequence located in the untranslated region (UTR), 5' or 3' UTR or both, of a transcript that, when present, increases the half life of the transcript relative to a transcript lacking the nucleotide sequence.

A nucleic acid described herein can contain an inducible promoter sequence operably linked to the transcriptional unit. "Inducible promoter sequence" refers to a sequence of nucleotides, wherein the binding of an agent, e.g., a metal or some other non-proteinaceous compound, to the sequence of nucleotides results in enhanced transcription of the transcriptional unit to which the sequence of nucleotides is operably linked. An example of an inducible promoter sequence is the metallothionine promoter.

A polypeptide encoded by a nucleic acid of the invention may optionally include a targeting signal. A targeting signal is a peptide which directs intracellular transport or secretion of a peptide to which it is attached. The targeting signal can be at the amino terminus, e.g., a signal sequence, or carboxy terminus, or within the hybrid polypeptide, so long as it functions in that site.

The targeting signal can be, for example, a signal sequence. Any signal sequence that directs the encoded protein to the endoplasmic reticulum and/or causes secretion of the encoded protein to which it is attached is suitable. A preferred targeting signal is the signal peptide of HLA-DRα: MAISGVPVLGFFIIAVLMSAQESWA (SEQ ID NO:27). Another signal sequence that can be linked to a polypeptide described herein has the following sequence: MAISGVPV-LGFFIIAMLMSAQESWAPRAT (SEQ ID NO:40). Another signal sequence that can be linked to a polypeptide described herein is the E1A signal sequence.

The targeting signal may optionally be modified to introduce an amino acid substitution at the junction(s) between the targeting signal and the adjacent segment(s) to promote cleavage of the targeting sequence from the epitopes by, e.g., a signal peptidase.

In another aspect, the invention features a nucleic acid including a transcriptional unit containing a coding sequence that encodes a polypeptide containing CYP1B1 or a portion thereof that contains a peptide that binds to an MHC class I or class II molecule, wherein the transcriptional unit does not contain 150 consecutive nucleotides of SEQ ID NO:18 or SEQ ID NO:19. Preferably the CYP1B1 or portion thereof corresponds to the sequence of a naturally occurring CYP1B1 polypeptide of a mammal, e.g., a human.

In one example, a transcriptional unit does not contain at least one of SEQ ID NOs:3–9 or 15–17. In another example, the transcriptional unit does not contain 50, 25, or 10 consecutive nucleotides of SEQ ID NO:18 or SEQ ID NO:19. In another example, the transcriptional unit does not contain any of SEQ ID NOs:3–9 or 15–17.

A transcriptional unit can contain a translational regulatory sequence operably linked to the coding sequence. "Translational regulatory sequence" refers to a sequence of nucleotides, wherein the binding of an agent to the sequence of nucleotides results in enhanced translation of a polypeptide encoded by the coding sequence to which the sequence is operably linked. In one example, the translational regulatory sequence is an iron responsive sequence.

In another aspect, the invention features a nucleic acid that contains a transcriptional unit that encodes a hybrid polypeptide containing a first and a second segment of CYP1B1. The first and second segments are either contiguous or separated by a spacer amino acid or spacer peptide. The first and second segments are each at least eight amino acids in length and are non-contiguous portions of CYP1B1.

By "spacer amino acid" is meant a single residue inserted between two neighboring segments ("A" and "B", in that order) in a polypeptide of the invention, where the residue is different from the amino acid which flanks the carboxy terminus of A and also is different from the amino acid which flanks the amino terminus of B in the full length CYP1B1 protein. Thus, the spacer amino acid forms a point of discontinuity from the CYP1B1-derived sequence of A and the CYP1B1-derived sequence of B, in the polypeptide of the invention. Typically, the amino acid will be one of the twenty naturally occurring amino acids, e.g., Ala, Leu, Ile, or Gly, and in general can be any amino acid except (1) the one that naturally flanks the carboxy terminus of A in CYP1B1, and (2) the one that naturally flanks the amino terminus of B in CYP1B1.

By "spacer sequence" is meant a sequence of two or more amino acids inserted between two neighboring segments, e.g., "A" and "B", in a polypeptide of the invention. The sequence of the spacer is different from the sequences which flank the carboxy terminus of A and the amino terminus of B in the full length CYP1B1 protein from which A and B were derived. Thus, the spacer sequence forms a point of discontinuity from both the CYP1B1-derived sequence of A and the Y-derived sequence of B in the polypeptide of the invention.

Examples of spacer sequences include Ala Ala, Ala Leu, Leu Leu, Leu Ala, Leu Ile, Ala Ala Ala, Ala Gly Leu, Phe Ile Ile, etc. Generally, the spacer sequence will include nonpolar amino acids, though polar residues such as Glu, Gln, Ser, His, and Asn could also be present, particularly for spacer sequences longer than three residues. The only outer limit on the total length and nature of each spacer sequence derives from considerations of ease of synthesis, proteolytic processing, and manipulation of the polypeptide and/or nucleic acid. It is generally unnecessary and probably undesirable to use spacer sequences longer than about four or five residues, though they could be, for example, up to 6, 8, 10, 15, 20, 30, or 50 residues. Of course, they could be even longer than 50 residues.

Spacer amino acids and spacer sequences are useful for altering protein stability or for promoting processing to release epitopes. The spacers are typically removed from the polypeptide by proteolytic processing in the cell, along with any sequence between epitopes within a given segment. This leaves the epitopes intact for binding to MHC molecules or (upon secretion from the cell) antibodies. Occasionally a spacer amino acid or part of a spacer sequence will remain attached to an epitope through incomplete processing. This generally will have little or no effect on binding to the MHC molecule.

The hybrid polypeptide encoded by a nucleic acid described herein can further include additional segments of CYP1B1, e.g. a third, fourth, fifth, or sixth segment. These additional segments are each at least eight amino acids in length and constitute non-contiguous portions of CYP1B1.

The spacer can optionally encode a T cell and/or B cell epitope from a protein other than CYP1B1. For example, the spacer can encode the tetanus toxoid or a PADRE T cell epitope (see, e.g., U.S. Pat. No. 5,662,907).

The invention also features a composition containing a nucleic acid described herein and an adjuvant or immunostimulatory agent. Adjuvants and "immunostimulatory agents" refer to substances that stimulate an immune response in a non-antigen specific manner or induce differentiation or activation of professional antigen presenting cells such as dendritic cells. Examples of adjuvants include alum, gold, monophosphoryl lipid A, saponin, oil based emulsions, QS21, and Freund's adjuvant. Examples of immunostimulatory agents include: a CpG containing oligonucleotide of, e.g., 18–30 nucleotides in length; cytokines such as IL-12, GM-CSF, IL-2, or IFN-gamma; cell surface receptors such as B7-1, B7-2, CCR5; and lipids, nucleic acids, carbohydrates, and bacterial polypeptides.

The invention also includes a composition containing a nucleic acid described herein and a nucleic acid encoding an immunostimulatory agent, e.g., IL-12, GM-CSF, IL-2, IFN-gamma, or a bacterial polypeptide.

The invention also includes a therapeutic composition containing a nucleic acid described herein and a pharmaceutically acceptable carrier. The invention also includes a microparticle, e.g., a microsphere containing a polymeric matrix or shell and a nucleic acid described herein. The invention also includes a polymeric network, e.g., a hydrogel and a nucleic acid described herein.

In another aspect, the invention features a method of inducing an immune response in a mammal by administering a nucleic acid described herein to the mammal. In one example, the mammal suffers from or is at risk for cancer. The nucleic acid can be administered by various routes, e.g., subcutaneously, intranasally, or intramuscularly. Injection of the nucleic acid may be followed by electroporation at the injection site. The immune response generated by this method can be directed to CYP1B1. The method can generate a T cell response and/or a B cell response.

The invention also features a method of inducing an immune response in a mammal by administering a microparticle or polymeric network described herein to the mammal.

The invention also features a method of generating an immune response that includes the steps of: (1) detecting a tumor or expression of CYP1B1 in a tumor of a mammal; and (2) administering a nucleic acid described herein to the mammal, wherein the administration results in the generation of an anti-CYP1B1 immune response in the mammal.

The invention also features a method of reducing tumor growth or tumor activity in a mammal. The method includes the following steps: (1) identifying a mammal having a tumor; (2) administering a nucleic acid described herein to the mammal; and (3) detecting a reduction in the size or activity of the tumor following the administration of the nucleic acid. As used herein, "tumor activity" refers to soluble factors secreted by a tumor cell that promote tumor cell growth. The method can further include a step of detecting CYP1B1 expression in the tumor before administering the nucleic acid.

The invention also features a method of increasing the time to relapse, life expectancy, or quality of life of a mammal. The method includes the following steps: (1) identifying a mammal having a tumor; (2) administering a nucleic acid described herein to the mammal; and (3) measuring an increase in the time to relapse, life expectancy, or quality of life of the mammal following administration of the nucleic acid. Increases in time to relapse, life expectancy, or quality of life can be measured, e.g., by a decreased need for chemotherapy or a decrease in duration of chemotherapy administration, a decreased need for pain medication or a decrease in duration of pain medication administration, or a decreased need or duration of hospitalization or medical treatment.

In another aspect, the invention features a method of inducing an immune response by delivering a nucleic acid described herein to a cell. The induction of the immune response can occur in vitro, in vivo, or ex vivo. For example, anti-CYP1B1 T cells can be generated in cell culture, e.g., by incubation with antigen presenting cells such as dendritic cells expressing CYP1B1 or pulsed with CYP1B1 protein or peptides, and then reintroduced into an individual, e.g., an individual suffering from or at risk of having cancer.

In another aspect, the invention features a method of inducing an immune response in a mammal by administering a nucleic acid to the mammal. In this method the mammal belongs to a first species, e.g., the mammal is a human, and the nucleic acid encodes a polypeptide that contains CYP1B1 or portion thereof that binds to an MHC class I or class II molecule or immunoglobulin receptor, wherein the CYP1B1 or portion thereof is identical to a sequence of a naturally occurring CYP1B1 polypeptide of a second species, e.g., a rodent such as a rat or a mouse.

The nucleic acid administered according to this method can be any nucleic acid that encodes a polypeptide that contains CYP1B1 or portion thereof that binds to an MHC class I or class II molecule or immunoglobulin receptor. In one example, the nucleic acid is a nucleic acid of the invention. The nucleic acid can be delivered to the mammal as a naked nucleic acid or associated with a delivery vehicle such as a microparticle. Preferably the CYP1B1 or portion thereof that binds to an MHC class I or class II molecule is not identical to a sequence of a naturally occurring CYP1B1 polypeptide of the first species. The nucleic acid can optionally be administered together with an immunostimulatory agent, as described herein.

The mammal to which the nucleic acid is administered may have or be at risk of having a cellular proliferative disorder, e.g., cancer. In one example, the mammal is identified as having a cellular proliferative disorder, e.g., a tumor, prior to administering the nucleic acid to the mammal.

An advantage of the invention is that the nucleic acids described herein permit the translation of the CYP1B1 polypeptide or a portion thereof in a cell where a CYP1B1 polypeptide is either not normally produced or is produced at low levels.

A further advantage of some of the nucleic acid constructs described herein is that they permit the translation of polypeptides with altered stability and/or altered, reduced, or absent enzymatic activity. Altering the stability of a polypeptide can enhance its processing and subsequent recognition by the immune system. Altering the enzymatic activity of a CYP1B1 protein reduce or eliminate an unwanted biological activity.

A further advantage of selected constructs of the invention is that they permit the delivery of MHC class I- or class II-binding epitopes from polypeptides having only a partial or altered sequence of a CYP1B1 protein. Thus, deleterious effects associated with expression of the full length CYP1B1 polypeptide are avoided. In addition, alterations in the coding sequence of the encoded CYP1B1 protein could break self-tolerance to the antigen.

A further advantage of selected constructs of the invention is that the assortment of epitopes within the polypeptides described herein increases the likelihood that at least one, and generally more than one, CYP1B1 epitope will be presented by each of a variety of HLA allotypes. This allows for immunization of a population of individuals polymorphic at the HLA locus, using a single nucleic acid encoding the polypeptide.

Unless otherwise defined, all technical and scientific terms used herein have the same meaning as commonly understood by one of ordinary skill in the art to which this invention belongs. Suitable methods and materials are described below, although methods and materials similar or equivalent to those described herein can also be used in the practice or testing of the present invention. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 1A–1D depict the sequence of a CYP1B1-encoding nucleic acid (SEQ ID NO:1) and polypeptide (SEQ ID NO:2).

DETAILED DESCRIPTION

Figure 2:
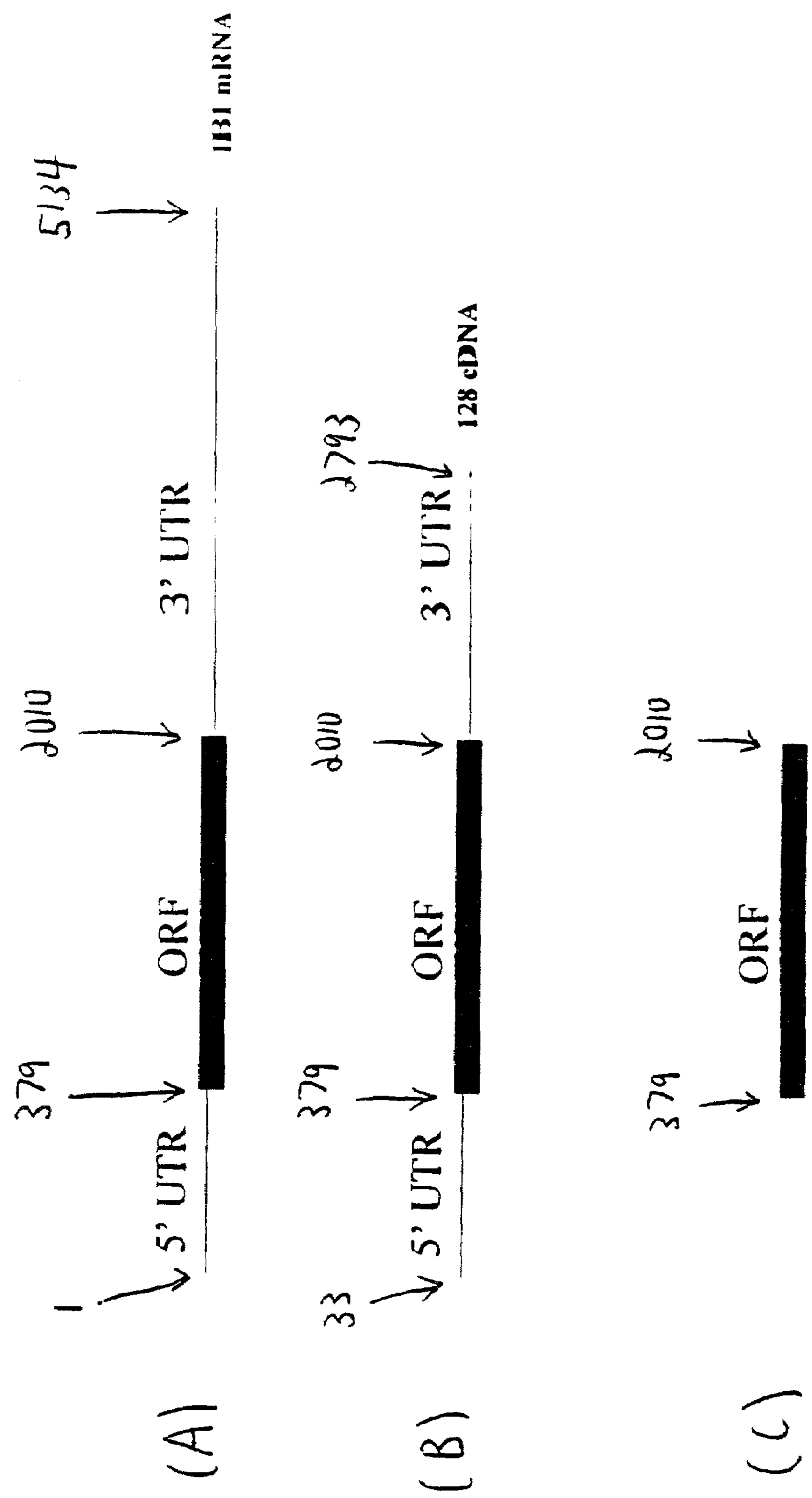
FIGS. 2A–2C are schematic drawings of CYP1B1 cDNA constructs containing an open reading frame (ORF) and various amounts of untranslated region (UTR).

The present invention provides nucleic acids containing transcriptional units that encode CYP1B1 polypeptides or portions thereof, wherein the transcriptional units lack sequences found in the untranslated region (UTR) of naturally occurring forms of the CYP1B1 transcript. Naturally occurring forms of a CYP1B1 transcript are thought to contain translational repressor elements that contribute to the partial or total suppression of translation, at least in some cellular environments. The nucleic acids of the invention lack translational repressor elements and thus provide for a system of enhanced translation of the CYP1B1 polypeptide or portions thereof.

Nucleic acids of the invention are useful as tools for generating or enhancing a CYP1B1-specific immune response in an individual. Because the nucleic acids lack translational repressor elements contained in naturally occurring CYP1B1 transcripts, they allow for production of a CYP1B1 protein or portion thereof and thus promote the development of an immune response. Because the nucleic acids of the invention can encode multiple CYP1B1 epitopes, they are useful in generating immune responses in a population containing a wide variety of MHC allotypes. The nucleic acids of the invention can also contain mutations, deletions, insertions, or rearrangements that help to promote the immunogenicity of the encoded protein. In this way, a protein containing an altered CYP1B1 sequence may cause tolerance to self may to be broken. In addition, the nucleic acids of the invention, because they lack translational repressor elements contained in naturally occurring CYP1B1 transcripts, are useful for generating CYP1B1 polypeptides or portions thereof, either in vitro or in vivo.

Nucleic Acids

The nucleic acids of the invention contain a transcriptional unit that (1) encodes a CYP1B1polypeptide or a portion thereof, but (2) does not correspond to a naturally occurring CYP1B1 transcript. The sequence of a human CYP1B1 nucleic acid (SEQ ID NO:1) and protein (SEQ ID NO:2) are depicted in FIGS. 1A–1D. These sequences are used herein as references to describe nucleic acids of the invention. Sequences of naturally-occurring human CYP1B1 nucleic acids are described in GenBank™ Accession U03688 and Tang et al. (1996) J. Biol. Chem. 271: 28324, the contents of which are incorporated by reference. Orthologous CYP1B1 sequences have been identified in other mammals, such as rat and mouse (Walker et al. (1995) Carcinogenesis 16:1319; Shen et al. (1994) DNA Cell Biology 13:763; Savas et al. (1994) J. Biol. Chem. 269:14905; herein incorporated by reference). Modified forms of eukaryotic CYP1B1 nucleic acids, e.g., human, rat, and mouse, are encompassed by the invention.

The nucleic acids of the invention differ from naturally occurring CYP1B1 nucleic acids in that the transcriptional units lack certain sequences contained in the 5' and/or 3' UTR that act as translational repressor elements. The identity of a translational repressor element can be determined in various ways.

In a first method of determining whether a nucleotide sequence contains a translational repressor element, the sequence of the full length RNA is analyzed, e.g., by a computer program, for the presence of consensus sequences associated with translational repression. For example, a computer analysis can identify sequences that may be bound by repressor agents, e.g., repressor proteins. In another example, a computer analysis can identify sequences that act as RNA destabilization sequences, e.g., nucleotide sequences whose presence reduces the half life of a transcript, at least in certain cellular environments. In another example, a computer analysis can identify consensus sequences that may form a secondary structure in a transcript and that are associated with translational repression.

An analysis of the UTR of the CYP1B1 RNA transcript corresponding to the sequence of SEQ ID NO:1 identified regions of putative secondary structure. This analysis was performed using the program mfold version 3.0 by Zuker and Turner (Zuker et al. (1999) Algorithms and Thermodynamics for RNA Secondary Structure Prediction: A Practical Guide, In RNA Biochemistry and Biotechnology, 11–43, J. Barciszewski & B. F. C. Clark, eds., NATO ASI Series, Kluwer Academic Publishers; Mathews et al. (1999) J. Mol. Biol. 288:911–940). mfold is a an implementation of the Zuker algorithm for RNA secondary structure prediction based on free energy minimization. The folding temperature in this analysis is fixed at 37° C.

Regions of predicted secondary structure in the CYP1B1 RNA transcript are depicted in Table 1. Because these regions constitute putative repressors of translation, a nucleic acid of the invention can lack one or more, e.g., 2, 3, 4, 5, 6, 7, 8, 9, 10, 11, 12, 13, 14, or 15, of these sequences, SEQ ID NOs:3–17.

TABLE 1

Secondary Structure Analysis of Untranslated Regions of the CYP1B1 Transcript

| Location in SEQ ID NO: 1 | UTR | Length | SEQ ID NO: |
|---|---|---|---|
| nucleotides 42–62 | 5' | 21 | 3 |
| nucleotides 72–112 | 5' | 41 | 4 |
| nucleotides 262–322 | 5' | 61 | 5 |
| nucleotides 262–362 | 5' | 101 | 6 |
| nucleotides 2022–2092 | 3' | 71 | 7 |
| nucleotides 2092–2162 | 3' | 71 | 8 |
| nucleotides 2222–2242 | 3' | 21 | 9 |
| nucleotides 2092–4272 | 3' | 2181 | 10 |
| nucleotides 2287–2762 | 3' | 476 | 11 |
| nucleotides 2252–4972 | 3' | 2721 | 12 |
| nucleotides 4352–4812 | 3' | 461 | 13 |
| nucleotides 4372–4822 | 3' | 451 | 14 |
| nucleotides 4832–4892 | 3' | 61 | 15 |
| nucleotides 4942–5002 | 3' | 61 | 16 |
| nucleotides 5012–5134 | 3' | 123 | 17 |

In a second method of determining whether a nucleotide sequence contains a translational repressor element, translational repressor elements can be identified by an empirical determination of the amount of protein produced by a modified CYP1B1 transcript as compared to a wild type CYP1B1 transcript. For example, a UTR deletion mutant of the sequence of SEQ ID NO:1 is constructed, the mutant and the sequence of SEQ ID NO:1 are each expressed in separate cell populations, and the amount of CYP1B1 protein produced from each of the mutant and the wild type is compared. If the modified transcript results in enhanced protein production as compared to the wild type CYP1B1, then it is expected to have one or more translational repressor elements. For example, a nucleic acid of the invention may lack the 5' UTR sequence of SEQ ID NO:18 (nucleotides 1–362 of SEQ ID NO:1). In another example, a nucleic acid can lack the 3' UTR sequence of SEQ ID NO:19 (nucleotides 2011–5128 of SEQ ID NO:1). In another example, a nucleic acid can lack both SEQ ID NO:18 and 19. In addition to nucleic acids lacking all of SEQ ID NO:18 and/or SEQ ID NO:19, the invention also includes nucleic acids that lack a specific number of consecutive nucleotides, e.g., at least 400, 300, 200, 150, 100, 50, 25, or 10, of SEQ ID NO:18 and/or SEQ ID NO:19. This analysis can be performed in conjunction with the computer analysis described above.

The nucleic acids of the invention can also differ from naturally occurring CYP1B1 nucleic acids in that they may contain mutations, deletions, insertions, or rearrangements that help to promote the immunogenicity of the encoded CYP1B1 protein or variant thereof. Methods of determining immunogenicity of a protein are well known in the art and include immunization of an animal with the nucleic acid, and subsequent removal and analysis of the lymph node, spleen, blood, or serum for T cell or B cell responses. Standard assays are described herein and include Cr51, Elispot, tetramer, ELISA, and intracellular cytokine staining analysis by FACS to measure cytotoxic T cells (CTL) specific for CYP1B1, Elispot and T cell proliferation studies to measure T helper responses, and ELISA and western analysis to measure B cell responses.

Modifications to a CYP1B1 nucleic acid, e.g., SEQ ID NO:1, can be made by methods well known to those of skill in the art. Deletions of particular 5' and/or 3' UTR sequences can be achieved by PCR amplification of a template using appropriate primer pairs and subcloning of the amplified product into an expression vector. For example, a nucleic acid lacking SEQ ID NO:18 and SEQ ID NO:19 can be constructed by PCR amplification, with the nucleic acid of SEQ ID NO:1 as a template, using primers that correspond to regions 363–382 of SEQ ID NO:1 (primer 1) and regions 1991–2010 of SEQ ID NO:1 (primer 2).

FIGS. 2A–2C depict three examples of CYP1B1-encoding nucleic acids. These figures refer to nucleotide positions of SEQ ID NO:1. FIG. 2A is the full length CYP1B1 nucleic acid of SEQ ID NO:1. FIG. 2B is a truncated form of SEQ ID NO:1, lacking a portion of the 5' UTR and 3' UTR. FIG. 2C lacks all 5' UTR as well as all 3' UTR sequences present in the CYP1B1 nucleic acid of FIG. 2A.

Regulatory elements can be included in the nucleic acid to facilitate expression of the nucleic acid encoding the polypeptide. These elements include sequences for enhancing expression in human or other mammalian cells, e.g., promoters and/or enhancers. For example, a T7 polymerase promoter, a viral promoter such as CMV, RSV, or LTR, a tissue-specific promoter such as a muscle-specific promoter, a cell-specific promoter such as an APC-specific promoter, or an inducible promoter is optionally present at the 5' end of the coding sequence. Examples of inducible promoters include a metallothionine promoter (see, e.g., Testa et al. (1994) Cancer Res. 54:4508) an a tetracycline-responsive promoter (see, e.g., Giavazzi et al. (2001) Cancer Res. 61:309).

The nucleic acid can also include an RNA stabilization sequence, e.g., an RNA stabilization sequence derived from the *Xenopus laevis* β-globin gene, 5' and/or 3' to the coding sequence; an intron (which can be placed at any location within or adjacent to the coding sequence); a poly(A) addition site; an origin of replication; and one or more genes encoding selectable markers, e.g., a kanarmycin resistance gene or auxotrophic marker, enabling the constructs to replicate and be selected in prokaryotic and/or eukaryotic hosts.

The nucleic acid can also include a translational regulatory sequence that is not derived from a naturally occurring CYP1B1 transcript. Examples of translational regulatory sequence are known in the art (see, e.g., Aziz and Munro (1987) Proc. Natl. Acad. Sci. USA 84:8478). The addition of a translational regulatory sequence to a transcriptional unit described herein can allow for translational regulation of protein expression. For example, the first 67 nucleotides of the 5' UTR of the ferritin mRNA (Aziz and Munro supra) can be coupled to a transcriptional unit described herein to render translation of the encoded protein an iron-responsive event.

The nucleic acid may also contain other transcriptional and translational signals, such as a Kozak sequence, as well as a sequence encoding an antibody determinant such as a FLAG, myc, HA, or His tag, optionally present at the 5' or 3' end of the coding sequence before the termination codon.

Nucleic acids encoding CYP1B1 polypeptides can be used in any vector that allows for expression in antigen-presenting cells (APC) of a mammal. The nucleic acid may be cloned into an expression vector, i.e., a vector in which the coding sequence is operably linked to expression control sequences. Vectors useful in this invention include linear nucleic acid fragments or circular DNAs, plasmid vectors, viral vectors, fungal vectors, and bacterial vectors. A "plasmid" is an autonomous, self-replicating, extrachromosomal, circular DNA. Preferred viral vectors are those derived from retroviruses, adenovirus, adeno-associated virus, pox viruses, SV40 virus, alpha viruses or herpes viruses. An example of a suitable vector is the family of pcDNA mammalian expression vectors (Invitrogen).

A nucleic acid can encode a single polypeptide or multiple polypeptides, each under the control of a different promoter, e.g., dual promoter vectors. A dual promoter vector permits two shorter polypeptides to replace the single longer version, with no loss in the number of epitopes produced from a given vector. It also allows adding new CYP1B1 sequences without altering the sequence, and perhaps the processing, of the first polypeptide. It also allows coding of two unrelated proteins such as CYP1B1 and an immunostimulating agent. Alternatively, a nucleic acid contains IRES sequences located between two coding sequences, e.g., between nucleic acid sequences encoding two polypeptides described herein. The IRES sequences cause the ribosome to attach to the initiator codon of the downstream translational unit and translate a second protein from a single polycistronic mRNA. Expression vectors encoding two or more polypeptides can optionally encode one secreted polypeptide and one non-secreted polypeptide. Such a vector can be used to induce both a T cell response and a B cell response. It also can be used to code for two unrelated proteins such as CYP1B1 and an immunostimulating agent.

CYP1B1 Polypeptides

The nucleic acids of the invention encode polypeptides containing CYP1B1 or a portion thereof that contains at least one peptide epitope that binds to an MHC class I or class II molecule or immunoglobulin receptor. The nucleic acids encoding the polypeptide described herein can encode a methionine residue at the amino terminus of the polypeptide to facilitate translation. The polypeptide can contain multiple epitopes of CYP1B1 as well as multiple segments of CYP1B1, each of which contains one or more epitopes. MHC-binding epitopes of CYP1B1 can be identified by methods well known to those of skill in the art. MHC class I-binding peptides are typically 8–10 amino acid residues in length, whereas MHC class II-binding peptides are typically 12–30 amino acid residues in length.

Epitopes that bind to a specific MHC allele can be identified by first synthesizing a series of overlapping peptide fragments from CYP1B1 and testing the peptides in art-recognized binding studies with a radio labeled peptide known to bind to the MHC allele. If a test peptide demonstrates specific binding to an MHC allele as measured by, for example, competition with the radio labeled test peptide (i.e., it is an epitope), the epitope can be combined with additional epitopes (overlapping or adjacent) to produce or define a segment. Examples of these and related methods can be found in U.S. Pat. No. 6,037,135, WO 99/45954, and WO 044775A2, herein incorporated by reference.

Alternatively, epitopes can be identified by refolding soluble MHC class I molecules in the presence of radiolabeled β2-microglobulin and a test peptide. The complete complex will refold and produce a receptor of the correct size. β2-microglobulin dissociates from the complex at a measurable rate that is directly correlated with the binding affinity of the test peptide (Garboczi et al. (1992) Proc. Nat. Acad. Sci. USA 89:3429; Parker et al. (1992) J. Biol. Chem. 267:5451; and Parker et al. (1992) J. Immunol. 149:1896). Analysis of this type of data has resulted in an algorithm that predicts the dissociation times of a given test peptide for an HLA-A2 receptor (Parker et al. (1994) J. Immunol. 52:163). Fast dissociation has been correlated with low affinity, and slow dissociation with high affinity. This algorithm has been expanded and is available for predicting binding affinity of epitopes for the HLA-A allotypes, -A1, -A2, -A3, -A11, and -A24. For an epitope to generate effective cytotoxic T cell (CTL) responses, it must bind to an MHC molecule on an antigen-presenting cell (APC), and the resulting receptor-ligand complex must be recognized by a T cell receptor expressed on the CTL.

Alternatively, epitopes may be identified by identifying MHC class I or class II-binding peptides using techniques described in, e.g., U.S. Pat. No. 5,827,516, and U.S. Ser. No. 09/372,380, now abandoned, herein incorporated by reference.

Epitopes that bind in vitro to MHC molecules as described above can be analyzed for their effectiveness at stimulating human T cell-responses (or used to generate a T cell response) in an in vitro immunization assay (see, e.g., Schultze et.al. (1997) J. Clin. Invest. 100:2757). Such an assay has been used previously to identify human and murine T cell-responsive epitopes (Alexander et al. (1996) Amer. J. Obstet. and Gynecol. 175:1586; Tarpey et al. (1994) Immunology 81:222). These assays have also been used to generate large numbers of specific CTL for immunotherapy (Tsai et al. (1998) Crit. Rev. Immunol. 18:65). To ensure reliability, it is desirable to perform the first round of T cell stimulation in the presence of dendritic cells (DCs) pulsed with the test peptide. Moreover, inclusion of IL-10 during the stimulation may suppress the non-specific responses that may sometimes arise during culture of the cells. T cell activation may then be examined using an ELISA assay to measure λ-IFN secretion, by ELISPOT to measure cytokines such as IL-10, IL-4, TNFα, IFN-γ or IL-2, or by use of FACS to determine the increase in CD8+, CD16− cells containing cytokines such as λ-IFN by tricolor analysis. Alternatively, T cell activation can be measured using a $^{51}$Cr release CTL assay or a tetramer-based assay (see, e.g., Molldrem et.al. (2000) Nature Med. 6:1018).

It is possible that not every individual with a given allotype will respond to a particular epitope. For example, one individual whose cells bear the HLA-A2 allotype may respond to a given epitope, whereas a second such individual may not. To overcome this difficulty, T cells from two donors, and even more preferably three donors, for each HLA allotype can be tested to verify that it is a T cell epitope. For the more common alleles (i.e., HLA-A2 and -A3) up to four donors are preferably tested.

Each epitope is tested initially with cells from one donor. If an epitope does not stimulate a T cell response using cells of the first donor, it is tested again with cells from a second donor, and then a third donor. If the epitope does not demonstrate T cell reactivity after two or three attempts, it is optionally not chosen for inclusion in a polypeptide.

Altering the method by which the in vitro presentation of antigen is performed may enhance analysis. An initial stimulation of T cells with DCs is typically part of the in vitro immunization. To enhance the immunization, DCs can be added at each round of stimulation to ensure adequate antigen presentation and T cell stimulation, e.g., using previously generated and subsequently frozen DCs. Alternatively, enhanced T cell stimulation can be achieved by activating the antigen presenting cells (APC) with an antibody binding to the APCs cell surface CD40 receptor.

Alternatively, the epitopes can be selected for inclusion in the construct based solely on their binding affinity to HLA molecules, or identified based upon analysis of naturally processed peptides, as described herein and in Chicz et al. (1993) J. Exp. Med. 178:27 and U.S. Pat. No. 5,827,516.

B cell epitopes can be selected based on their ability to induce immune responses in mammals. For example, CYP1B1 peptides are mixed with freund's adjuvant and injected into mice. Serum from immunized animals is collected and tested by Western blot for reactivity to CYP1B1 (commercially available, Gentest, Woburn Mass.).

Polypeptides encoded by nucleic acids of the invention do not necessarily include the full length CYP1B1 protein of SEQ ID NO:2. For example, a polypeptide encoded by a nucleic acid of the invention can lack the bioactivation properties of naturally occurring CYP1B1 (see, e.g., Heidel et al. (2000) Cancer Res. 60:3454). A nucleic acid encoding a CYP1B1 polypeptide or portion thereof can include a coding sequence that contains a loss of function mutation, e.g., an insertion, a deletion, a frame shift mutation, or a single nucleotide mutation (Bailey et al. (1998) Cancer Res. 58:5038). Examples of frame shift mutations in a CYP1B1 coding sequence are described in Stoilov et al. (1997) Hum. Mol. Gen. 6:641 and Sarfarazi et al. (1997) Hum. Mol. Gen. 6:1667. In another example, a polypeptide can lack all or part of the hinge region (e.g., about amino acids 38–61 of SEQ ID NO:2) or conserved core sequence of the heme-binding portion of CYP1B1 located between about amino acids 400–540 of SEQ ID NO:2 (Stoilov et al. (1998) Am. J. Human Genet. 62:573). In another example, a polypeptide can lack all or part the oxidation-reduction domain of CYP1B1, or have mutations in active site regions (Lewis et al. (1999) Toxicology 139:53), or in regions required for protein folding or stability. In another example, a polypeptide can lack all or part of a CYP1B1 transmembrane region located between about amino acids 18–37 of SEQ ID NO:2.

Figure 3:
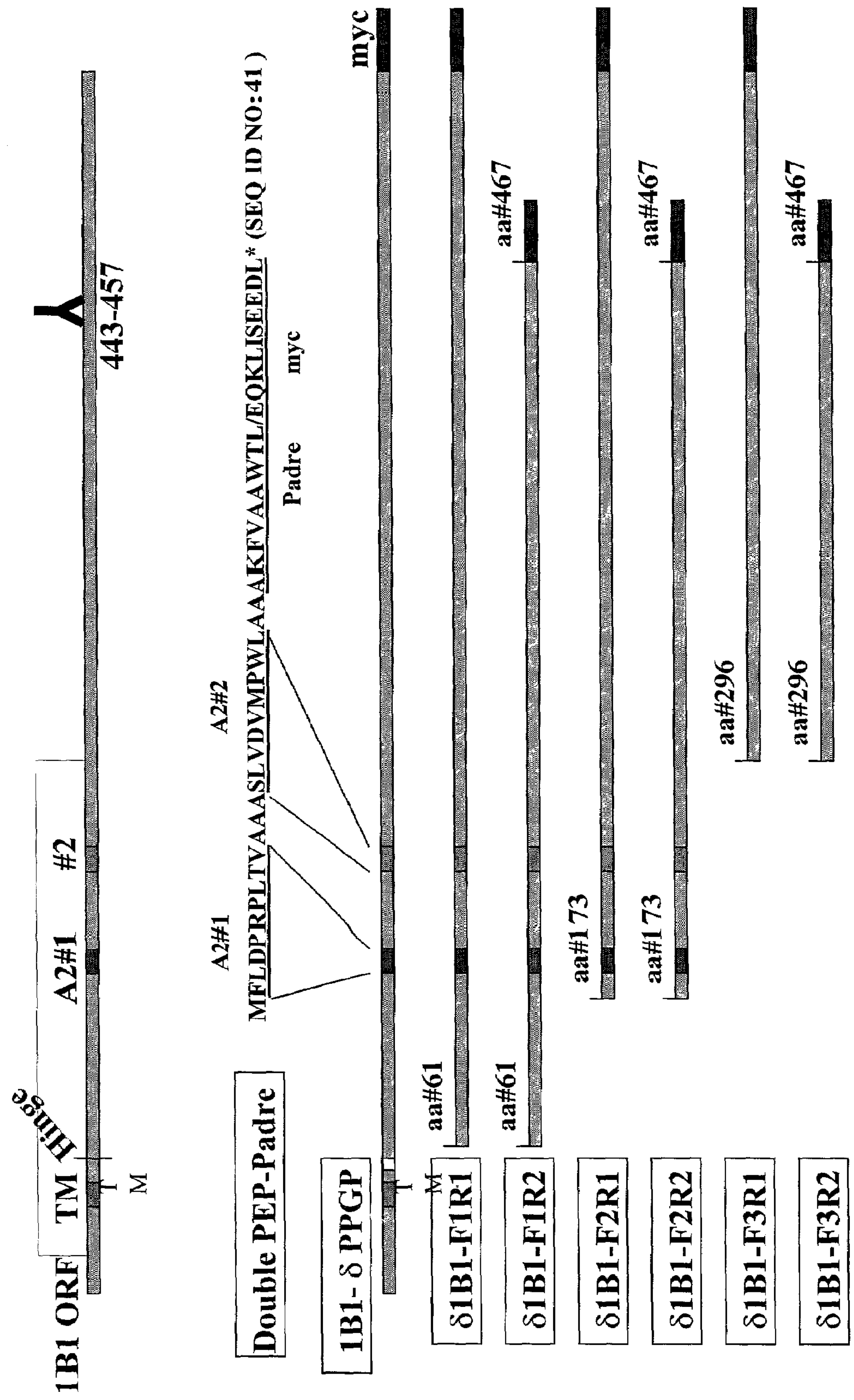
FIG. 3 is a schematic drawing of a CYP1B1 polypeptide (SEQ ID NO:2) and several CYP1B1 truncation and deletion mutants.

FIG. 3 depicts a CYP1B1 polypeptide (SEQ ID NO:2) and fragments and variants thereof. The various polypeptides depicted in FIG. 3 can be encoded by CYP1B1-encoding nucleic acids described herein, e.g., nucleic acids lacking all or a portion of a 5' UTR and/or a 3' UTR. Some of the polypeptides include the peptide of SEQ ID NO:22. The following is a description of the CYP1B1 fragments and variants depicted in FIG. 3.

SEQ ID NO:31

This polypeptide contains a deletion of four amino acids (residues 51–54 of SEQ ID NO:2) in the hinge region of CYP1B1. This polypeptide contains amino acid changes, as compared to the wild type protein, at residues 57(W to C), 61(G to E), 365(G to W), 379(P to L), and 387(E to K). The altered residues are underlined. The amino acid sequence of SEQ ID NO:31 is recited as follows:

MGTSLSPNDPWPLNPLSIQQTTLLLLLSVLATVHVGQRLLRQRRRQLRSA
FACPLIENAAAVGQAAHLSFARLARRYGDVFQIRLGSCPIVVLNGERAIH
QALVQQGSAFADRPAFASFRVVSGGRSMAFGHYSEHWKVQRRAAHSMMRN
FFTRQPRSRQVLEGHVLSEARELVALLVRGSADGAFLDPRPLTVVAVANV
MSAVCFGCRYSHDDPEFRELLSHNEEFGRTVGAGSLVDVMPWLQYFPNPV
RTVFREFEQLNRNFSNFILDKFLRHCESLRPGAAPRDMMDAFILSAEKKA
AGDSHGGGARLDLENVPATITDIFGASQDTLSTALQWLLLLFTRYPDVQT
RVQAELDQVVWRDRLPCMGDQPNLLYVLAFLYKAMRFSSFVPVTIPHAT
TANTSVLGYHIPKDTVVFVNQWSVNHDPVKWPNPENFDPARFLDKDGLIN
KDLTSRVMIFSVGKRRCIGEELSKMQLFLFISILAHQCDFRANPNEPAKM
NFSYGLTIKPKSFKVNVTLRESMELLDSAVQNLQAKETCQEQKLISEED
L.

SEQ ID NO:32

This polypeptide contains a deletion of amino acids 1–60 of SEQ ID NO:2. The deletion encompasses the ER domain, transmembrane domain, and hinge region of CYP1B1. A methionine (underlined) is positioned at the amino terminus of the polypeptide of SEQ ID NO:32. This polypeptide contains amino acid changes, as compared to the wild type protein, at residues 365(G to W), 379(P to L), and 387(E to K). The altered residues are also underlined. This sequence has been denoted F1R1. The amino acid sequence of SEQ ID NO:32 is recited as follows:

MGNAAAVGQAAHLSFARLARRYGDVFQIRLGSCPIVVLNGERAIHQALVQ
QGSAFADRPAFASFRVVSGGRSMAFGHYSEHWKVQRRAAHSMMRNFFTRQ
PRSRQVLEGHVLSEARELVALLVRGSADGAFLDPRPLTVVAVANVMSAVC
FGCRYSHDDPEFRELLSHNEEFGRTVGAGSLVDVMPWLQYFPNPVRTVFR
EFEQLNRNFSNFILDKFLRHCESLRPGAAPRDMMDAFILSAEKKAAGDSH
GGGARLDLENVPATITDIFGASQDTLSTALQWLLLLFTRYPDVQTRVQAE
LDQVVWRDRLPCMGDQPNLLYVLAFLYKAMRFSSFVPVTIPHATTANTSV

-continued

LGYHIPKDTVVFVNQWSVNHDPVKWPNPENFDPARFLDKDGLINKDLTSR
VMIFSVGKRRCIGEELSKMQLFLFISILAHQCDFRANPNEPAKMNFSYGL
TIKPKSFKVNVTLRESMELLDSAVQNLQAKETCQEQKLISEEDL.

SEQ ID NO:33

This polypeptide contains a deletion of amino acids 1–60 and 462–543 of SEQ ID NO:2. The deletion encompasses the ER domain, transmembrane domain, and hinge region of CYP1B1. A methionine (underlined) is placed at the amino terminus of the polypeptide of SEQ ID NO:33. This polypeptide contains amino acid changes, as compared to the wild type protein, at residues 365(G to W), 379(P to L), and 387(E to K). The altered residues are also underlined. This sequence has been denoted F1R2. The amino acid sequence of SEQ ID NO:33 is recited as follows:

MGNAAAVGQAAHLSFARLARRYGDVFQIRLGSCPIVVLNGERAIHQALVQ
QGSAFADRPAFASFRVVSGGRSMAFGHYSEHWKVQRRAAHSMMRNFFTRQ
PRSRQVLEGHVLSEARELVALLVRGSADGAFLDPRPLTVVAVANVMSAVC
FGCRYSHDDPEFRELLSHNEEFGRTVGAGSLVDVMPWLQYFPNPVRTVFR
EFEQLNRNFSNFILDKFLRHCESLRPGAAPRDMMDAFILSAEKKAAGDSH
GGGARLDLENVPATITDIFGASQDTLSTALQWLLLLFTRYPDVQTRVQAE
LDQVVWRDRLPCMGDQPNLLYVLAFLYKAMRFSSFVPVTIPHATTANTSV
LGYHIPKDTVVFVNQWSVNHDPVKWPNPENFDPARFLDKDGLINKDLTSR
VMEQKLISEEDL.

SEQ ID NO:34

This polypeptide contains a deletion of amino acids 1–171 of SEQ ID NO:2. The deletion encompasses the ER domain, transmembrane domain, and hinge region of CYP1B1. A methionine (underlined) is placed at the amino terminus of the polypeptide of SEQ ID NO:34. This polypeptide contains amino acid changes, as compared to the wild type protein, at residues 365(G to W), 379(P to L), and 387(E to K). The altered residues are also underlined. This sequence has been denoted F2R1. The amino acid sequence of SEQ ID NO:34 is recited as follows:

MSEARELVALLVRGSADGAFLDPRPLTVVAVANVMSAVCFGCRYSHDDPE
FRELLSHNEEFGRTVGAGSLVDVMPWLQYFPNPVRTVFREFEQLNRNFSN
FILDKFLRHCESLRPGAAPRDMMDAFILSAEKKAAGDSHGGGARLDLENV
PATITDIFGASQDTLSTALQWLLLLFTRYPDVQTRVQAELDQVVWRDRLP
CMGDQPNLLYVLAFLYKAMRFSSFVPVTIPHATTANTSVLGYHIPKDTVV
FVNQWSVNHDPVKWPNPENFDPARFLDKDGLINKDLTSRVMIFSVGKRRC
IGEELSKMQLFLFISILAHQCDFRANPNEPAKMNFSYGLTIKPKSFKVNV
TLRESMELLDSAVQNLQAKETCQEQKLISEEDL.

SEQ ID NO:35

This polypeptide contains a deletion of amino acids 1–171 and 462–543 of SEQ ID NO:2. The deletion encompasses the ER domain, transmembrane domain, and hinge region of CYP1B1. A methionine (underlined) is placed at the amino terminus of the polypeptide of SEQ ID NO:35. This polypeptide contains amino acid changes, as compared to the wild type protein, at residues 365(G to W), 379(P to L), and 387(E to K). The altered residues are also underlined. This sequence has been denoted F2R2. The amino acid sequence of SEQ ID NO:35 is recited as follows:

MSEARELVALLVRGSADGAFLDPRPLTVVAVANVMSAVCFGCRYSHDDPE
FRELLSHNEEFGRTVGAGSLVDVMPWLQYFPNPVRTVFREFEQLNRNFSN
FILDKFLRHCESLRPGAAPRDMMDAFILSAEKKAAGDSHGGGARLDLENV
PATITDIFGASQDTLSTALQWLLLLFTRYPDVQTRVQAELDQVVWRDRLP
CMGDQPNLLYVLAFLYKAMRFSSFVPVTIPHATTANTSVLGYHIPKDTVV
FVNQWSVNHDPVKWPNPENFDPARFLDKDGLINKDLTSRVMEQKLISEED
L.

SEQ ID NO:36

This polypeptide contains a deletion of amino acids 1–292 of SEQ ID NO:2. The deletion encompasses the ER domain, transmembrane domain, and hinge region of CYP1B1. This polypeptide contains amino acid changes, as compared to the wild type protein, at residues 365(G to W), 379(P to L), and 387(E to K). The altered residues are underlined. This sequence has been denoted F3R1. The amino acid sequence of SEQ ID NO:36 is recited as follows:

MDAFILSAEKKAAGDSHGGGARLDLENVPATITDIFGASQDTLSTALQWL
LLLFTRYPDVQTRVQAELDQVVWRDRLPCMGDQPNLLYVLAFLYKAMRFS
SFVPVTIPHATTANTSVLGYHIPKDTVVFVNQWSVNHDPVKWPNPENFDP
ARFLDKDGLINKDLTSRVMIFSVGKRRCIGEELSKMQLFLFISILAHQCD
FRANPNEPAKMNFSYGLTIKPKSFKVNVTLRESMELLDSAVQNLQAKETC
QEQKLISEEDL.

SEQ ID NO:37

This polypeptide contains a deletion of amino acids 1–292 and 462–543 of SEQ ID NO:2. The deletion encompasses the ER domain, transmembrane domain, and hinge region of CYP1B1. This polypeptide contains amino acid changes, as compared to the wild type protein, at residues 365(G to W), 379(P to L), and 387(E to K). The altered residues are underlined. This sequence has been denoted F3R2. The amino acid sequence of SEQ ID NO:37 is recited as follows:

MDAFILSAEKKAAGDSHGGGARLDLENVPATITDIFGASQDTLSTALQWL
LLLFTRYPDVQTRVQAELDQVVWRDRLPCMGDQPNLLYVLAFLYKAMRFS
SFVPVTIPHATTANTSVLGYHIPKDTVVFVNQWSVNHDPVKWPNPENFDP
ARFLDKDGLINKDLTSRVMEQKLISEEDL.

An insertion, deletion, frame shift mutation, or single nucleotide mutation can be introduced into a CYP1B1 polypeptide sequence to result in a polypeptide with an altered stability and/or biological activity as compared to the wild type protein. By altering the stability of a CYP1B1 polypeptide, this can affect its processing by the cellular machinery. For example, a CYP1B1 polypeptide with decreased stability is expected to undergo increased processing, thereby resulting in an increase in CYP1B1 peptides presented by MHC class I and/or class II molecules. By altering (e.g., reducing or eliminating) the biological activity of CYP1B1, unwanted activity such as enzymatic activity can be reduced or eliminated.

The following are examples of CYP1B1 polypeptides containing alterations at three (SEQ ID NO:38) and five (SEQ ID NO:39) amino acid residues, as compared to the wild type CYP1B1 protein.

SEQ ID NO:38

This polypeptide contains amino acid changes, as compared to the wild type protein, at residues 57(W to C), 61(G to E), and 365(G to W). The altered residues are underlined. The amino acid sequence of SEQ ID NO:38 is recited as follows:

MGTSLSPNDPWPLNPLSIQQTTLLLLLSVLATVHVGQRLLRQRRRQLRSA
PPGPFACPLIENAAAVGQAAHLSFARLARRYGDVFQIRLGSCPIVVLNGE
RAIHQALVQQGSAFADRPAFASFRVVSGGRSMAFGHYSEHWKVQRRAAHS
MMRNFFTRQPRSRQVLEGHVLSEARELVALLVRGSADGAFLDPRPLTVVA
VANVMSAVCFGCRYSHDDPEFRELLSHNEEFGRTVGAGSLVDVMPWLQYF
PNPVRTVFREFEQLNRNFSNFILDKFLRHCESLRPGAAPRDMMDAFILSA
EKKAAGDSHGGGARLDLENVPATITDIFGASQDTLSTALQWLLLLFTRYP
DVQTRVQAELDQVVWRDRLPCMGDQPNLPYVLAFLYEAMRFSSFVPVTIP
HATTANTSVLGYHIPKDTVVFVNQWSVNHDPVKWPNPENFDPARFLDKDG
LINKDLTSRVMIFSVGKRRCIGEELSKMQLFLFISILAHQCDFRANPNEP
AKMNFSYGLTIKPKSFKVNVTLRESMELLDSAVQNLQAKETCQ.

SEQ ID NO:39

This polypeptide contains amino acid changes, as compared to the wild type protein, at residues 57(W to C), 61(G to E), 365(G to W), 379(P to L), and 387(E to K). The altered residues are underlined. The amino acid sequence of SEQ ID NO:39 is recited as follows:

MGTSLSPNDPWPLNPLSIQQTTLLLLLSVLATVHVGQRLLRQRRRQLRSA
PPGPFACPLIENAAAVGQAAHLSFARLARRYGDVFQIRLGSCPIVVLNGE
RAIHQALVQQGSAFADRPAFASFRVVSGGRSMAFGHYSEHWKVQRRAAHS
MMRNFFTRQPRSRQVLEGHVLSEARELVALLVRGSADGAFLDPRPLTVVA
VANVMSAVCFGCRYSHDDPEFRELLSHNEEFGRTVGAGSLVDVMPWLQYF
PNPVRTVFREFEQLNRNFSNFILDKFLRHCESLRPGAAPRDMMDAFILSA
EKKAAGDSHGGGARLDLENVPATITDIFGASQDTLSTALQWLLLLFTRYP
DVQTRVQAELDQVVWRDRLPCMGDQPNLLYVLAFLYKAMRFSSFVPVTIP
HATTANTSVLGYHIPKDTVVFVNQWSVNHDPVKWPNPENFDPARFLDKDG
LINKDLTSRVMIFSVGKRRCIGEELSKMQLFLFISILAHQCDFRANPNEP
AKMNFSYGLTIKPKSFKVNVTLRESMELLDSAVQNLQAKETCQ.

As described above, polypeptides encoded by the nucleic acids described herein include all of CYP1B1 or a portion thereof that binds to an MHC class I or class II molecule or immunoglobulin receptor. A polypeptide can contain 25, 50, 150, 200, 250, 300, 400, 500 or more amino acids corresponding to a sequence of consecutive amino acids present in SEQ ID NO:2. Additionally, the polypeptide can be less than 300, 200, 150, 100, or 50 amino acids in length. For example, the polypeptide can contain SEQ ID NO:20(amino acids 1–272 of SEQ ID NO:2) or SEQ ID NO:21(amino acids 273–544 of SEQ ID NO:2).

Any of the CYP1B1 polypeptides or fragments thereof described herein can contain all or a portion of a sequence identical to the wild type CYP1B1 protein or an altered CYP1B1 sequence. For example, polypeptides having the structure of any of those described herein (e.g., the polypeptides depicted in FIG. 3) can be made so as to include any one or more (e.g., one, two, three, four, or five) of the amino acid alterations contained in the polypeptides of SEQ ID NO:38 and/or SEQ ID NO:39.

A polypeptide encoded by a nucleic acid described herein can contain the amino acid sequence FLDPRPLTV (SEQ ID NO:22), which corresponds to amino acid residues 190–198 of SEQ ID NO:2). The peptide of SEQ ID NO:22 is a naturally processed epitope of the CYP1B1 polypeptide. Additionally, a polypeptide can include at least 8 amino acids derived from the sequence of SEQ ID NO:23 (amino acid residues 185–205 of SEQ ID NO:2). A polypeptide containing SEQ ID NO:22 or SEQ ID NO:23 can be less than 300, 200, 150, 100, or 50 amino acids in length.

The nucleic acids of the invention may in addition include one or more sequences encoding targeting signals that direct the polypeptide to a desired intracellular compartment, the targeting signal being linked to the polypeptide. Targeting signals (the term is used interchangeably with trafficking signal or targeting sequence) can target the protein for secretion or can direct the polypeptide to endoplasmic reticulum (ER), the golgi, the nucleus, a lysosome, a class II peptide loading compartment, or an endosome, and include signal peptides (the amino terminal sequences which direct proteins into the ER during translation), ER retention peptides such as KDEL (SEQ ID NO:24), and lysosome-targeting peptides such as KFERQ (SEQ ID NO:25), QREFK (SEQ ID NO:26), and other pentapeptides having Q flanked on one side by four residues selected from K, R, D, E, F, I, V, and L. Also included are targeting signals that direct the secretion of the polypeptide (e.g., SEQ ID NO:40). Also included are targeting signals that direct insertion of the polypeptide into a membrane (e.g., a transmembrane sequence). Polypeptides including a membrane insertion sequence can be constructed either with or without a cytoplasmic tail.

An example of an ER-targeting sequence is the HLA-DRα leader sequence, MAISGVPVLGFFIIAVLMSAQESWA (SEQ ID NO:27). The targeting sequence may include only a portion (e.g., at least ten amino acid residues) of this specified 25 residue sequence, provided that the portion is sufficient to cause targeting of the polypeptide to the ER. Another example of a targeting sequence is the E1A sequence.

Nuclear localization sequences include nucleoplasmin- and SV40-like nuclear targeting signals, as described in Chelsky et al. (1989) Mol. Cell Biol. 9:2487; Robbins (1991) Cell 64:615; and Dingwall et al. (1991) TIBS 16:478. Some nuclear localization sequences include AVKRPAATKKAGQAKKK (SEQ ID NO:28), RPAATKKAGQAKKKKLD (SEQ ID NO:29), and AVKRPAATKKAGQAKKKLD (SEQ ID NO:30).

In some cases it is desirable to modify the amino acid sequence of the targeting signal to facilitate cleavage by a signal peptidase or other proteolytic agent. Recognition sequences for signal peptidases are described in Von Heijne (1986) Nucleic Acids Research 14:4683. The −3, −1 rules of von Heijne can be used to select a sequence that increases the probability of successful cleavage by signal peptidase when the targeting signal is present.

In some cases it is desirable to modify the polypeptide sequence, with respect to the wild type CYP1B1 sequence, by altering the stability of the polypeptide. One method of decreasing the stability of a polypeptide is by facilitating its targeting it to the proteasome. For example, a targeting signal comprising ubiquitin sequences can be linked to a polypeptide described herein, so as to target the polypeptide to the cellular proteasome for degradation (see, e.g., Hochstrasser (1995) Curr. Opin. Cell. Biol. 7:215–223; Rodriguez et al. (1997) J. Virol. 71:8497–8503). In another method of decreasing the stability of a polypeptide, a polypeptide can lack all or a portion of a CYP1B1 sequence that contributes to protein stability, e.g., all or a portion of the hinge region (about amino acids 38–61 of SEQ ID NO:2). In one example, a polypeptide lacks the PPGP region located between amino acids 51–54 of SEQ ID NO:2(see, e.g., the polypeptide of SEQ ID NO:31).

Alternatively, a polypeptide can lack a targeting signal, which will cause the polypeptide to be located in the cytoplasm.

Once expressed in a cell, the encoded peptide can be processed into one of several MHC class I binding epitopes. The MHC molecule, upon binding to the peptide, can activate a T cell response. MHC class II binding peptides may also be generated from the encoded peptide. These peptides would be expected to activate T helper cells or CTL upon presentation by the MHC class II expressing cells. Other receptors may also bind the encoded peptide or its processed fragments to activate immune cells such as NK or B cells. These cells may also be activated by cytokines elicited in response to the peptides of the invention. In one example, secretion signals such as SEQ ID NO:40 are added to the polypeptide, resulting in the secretion of the polypeptide and the activation of immune cells such as B cells.

In those polypeptides containing multiple segments of CYP1B1, the order of the segments within the polyepitope polypeptide can correspond to the order in which the segments appear in the native CYP1B1 protein, though some of the amino acid sequence (i.e., at least one residue) between the individual segments in the native protein may be deleted. Alternatively, the segment order may differ from that in the naturally occurring protein. A protein created by this process may have been designed via molecular evolution (see, e.g., U.S. Pat. No. 6,132,970), exon shuffling or domain shuffling approaches.

To determine whether the polypeptide is processed and the epitopes are presented by MHC, an in vitro T cell stimulation assay can be performed using autologous spleen cells, PBL, or EBV-transformed cells infected with a recombinant vaccinia virus that contain the polyepitope polypeptide coding sequence. These target cells are generated by incubating spleen cells or PBL with the recombinant vaccinia at an multiplicity of infection (moi) of 3–10 plaque forming units (pfu)/cell at 37° C. for 2 hours. After infection, cells are pelleted, washed and used as targets in the in vitro stimulation assay. The stimulated T cells from one or more individuals, e.g., a mouse or a human, with the different MHC allotypes (or from one or more individuals immunized with CYP1B1 polypeptides or nucleic acid constructs) are incubated with the target cells, and the ability of the target cells to stimulate the T cells is measured, e.g., by λ-interferon expression or secretion.

Alternatively, epitope processing from the polyepitope polypeptide can be examined using proteasomes purified from human cells (Theobald et al. (1998) J. Exp. Med. 188:1017; Kisselev et al. (1999) J. Biol. Chem. 289:3363; and Nussbaum et al. (1998) Proc. Nat. Acad. Sci. (USA) 95:12404).

In addition to the T cell assays, an assay that utilizes mice, e.g., transgenic mice, can be used to verify that the construct functions (e.g., epitopes are correctly processed and presented) when delivered in vivo. For measuring HLA-A2-restricted presentation, the polyepitope construct in a mammalian expression vector (e.g., a plasmid) is encapsulated in microparticles and introduced into HLA-A2 transgenic mice by a route such as intramuscular or subcutaneous injection. The construct may alternatively be administered without the microparticle delivery vehicle, e.g., in a recombinant viral or bacterial vector, e.g., vaccinia virus or as naked DNA. T cell responses are subsequently examined in vitro (Hedley et al., Nature Med. 4:365–68, 1998). Target cells can be T2A2 cells (T2 cells transfected with DNA encoding HLA-A2) or EL4.A2 cells (EL4 cells transfected with DNA encoding HLA-A2) pulsed with the A2 epitope being tested and T2A2 cells into which has been introduced a nucleic acid of the invention. Parallel studies are performed using EL4.A2 or T2A2 cells pulsed with no peptide or with an irrelevant peptide. In this way, HLA-A2 epitopes that are processed and presented in vivo following administration of the nucleic acid of the invention are identified. A positive result suggests that processing of the polyepitope polypeptide is occurring as predicted.

Alternately, polyepitope polypeptides may be made according to methods of Hanke, et al. (1998) Vaccine 16:426, or as described in U.S. Ser. No. 60/154,665 and U.S. Ser. No. 60/169,846, which are hereby incorporated by reference.

Immunostimulatory Agent

A composition can include a nucleic acid as described herein as well as an adjuvant or immunostimulatory agent or a nucleic acid encoding an immunostimulatory agent. Examples of useful adjuvants and immunostimulatory agents include: ISCOMS, virus like particles (VLPs), alum, gold, freund's adjuvant, cytokines such as IL-12, GM-CSF, IL-2, or IFN-gamma; cell surface receptors such as B7-1, B7-2 or CCR5; lipopolysaccharide (LPS); monophosphoryl lipid A; QS21; CpG-containing oligonucleotides, e.g., of 18–30 nucleotides in length, and bacterial polypeptides such as a bacteriotoxin. Any compound that stimulates differentiation or activation of professional antigen presenting cells such as dendritic cells is a useful immunostiumulatory agent. Examples of CpG-containing oligonucleotides are described in U.S. Pat. No. 6,239,116. A nucleic acid encoding a polypeptide described herein and an immunostimulatory agent can optionally be included in a single vector, e.g., a two promoter vector or IRES vector as described herein. Alternatively, a nucleic acid of the invention can encode a CYP1B1 polypeptide or portion thereof fused in frame to an immunostimulatory agent. Methods of creating such fusion proteins are well known in the art and are described in, for example, WO 95/05849.

Methods

The nucleic acids of the invention can be used as immunogens in individuals known to have various types of cell proliferative disorders, such as lymphoproliferative disorders or cancer, individuals suspected of having various types of cancer, or individuals susceptible to various types of cancer (e.g., individuals having genetic and/or hereditary indicia of cancer susceptibility, e.g., mutations in the BRCA1 gene). Other suitable individuals include those displaying symptoms of, or likely to develop, cancer-associated conditions. The nucleic acids can be used, prophylactically or therapeutically, to prevent or treat conditions associated with several different cell proliferative disorders or cancers, e.g., cancers of the bladder, breast, colon, connective tissue, lung, esophagus, skin, lymph node, brain, ovary, stomach, uterus, testis, and prostate. In one example, the nucleic acid is used as a vaccine.

The nucleic acids encoding the peptides can administered alone or in combination with other therapies known in the art, e.g., chemotherapeutic regimens, radiation, and surgery, to treat various types of proliferative disorders or cancer, or diseases associated with these proliferative disorders or cancers. In addition, the nucleic acid of the invention can be administered in combination with other treatments designed to enhance immune responses, e.g., by co-administration with adjuvants, vitamins, immunostimulatory agents, or cytokines (or nucleic acids encoding cytokines), as is well known in the art. Compositions containing nucleic acids and immunostimulatory agents are described herein.

The nucleic acid of the invention can also be used in manufacture of a medicament for the prevention or treatment of various cancers, or conditions associated with these cancers.

Nucleic acids encoding CYP1B1 polypeptides or portions thereof can be used in immunotherapy to stimulate the immune reaction of a cancer patient against a rapidly proliferating cell population or tumor, e.g., a tumor that expresses the CYP1B1 protein and presents CYP1B1 peptides in the context of an MHC molecule or a tumor that expresses the CYP1B1 protein on the cell surface. Because naturally occurring forms of a CYP1B1 transcript are thought to contain translational repressor elements that contribute to the partial or total suppression of translation, the immune system of an individual may be naive or tolerant to CYP1B1. CYP1B1 protein expression in other cells may result in immunologic self-tolerance and thus mechanisms to break self-tolerance may increase the efficacy of the nucleic acids of the invention. For example, the nucleic acids of the invention lack at least one translational repressor element and thus provide for a system of enhanced translation of the CYP1B1 polypeptide or portions thereof, thereby enabling an individual's immune system to generate an anti-CYP1B1 immune response. A polypeptide described herein can be produced in one cell of an individual, e.g., a non-cancerous cell such as a non-cancerous APC, and cause the generation of an immune response, e.g., a humoral and/or cellular immune response, against another cell of the individual, e.g., a cancer cell.

Some individuals exposed to high levels of carcinogens, such as smokers, may express high levels of CYP1B1 and therefore display tolerance to the protein. By generating an anti-CYP1B1 immune response by methods described herein, this tolerance may be broken in such an individual, thereby resulting in the generation of an immune response against a CYP1B1-expressing cell, e.g., a cancer cell.

The nucleic acid constructs described herein can also be used in ex vivo treatment. For example, cells such as dendritic cells, peripheral blood mononuclear cells, or bone marrow cells can be obtained from an individual or an appropriate donor and activated ex vivo with a nucleic acid composition or polypeptides encoded by the nucleic acids described herein, and then returned to the individual. In addition, cells such as myoblasts can be transfected or infected with a nucleic acid expression vector described herein, and then administered to an individual. The CYP1B1-expressing myoblasts can thus act as an in vivo source of CYP1B1 for generating an anti-CYP1B1 immune response.

The methods described herein for generating an anti-CYP1B1 immune response can also include generating an immune response against one or more additional cancer related antigens, such as telomerase, carcinoembryonic antigen (CEA), or p53, incident to the generation of an anti-CYP1B1 immune response. Such an immune response can be achieved by a variety of methods, including administration of a nucleic acid encoding two polypeptides, wherein the first polypeptide is a CYP1B1-containing polypeptide described herein and the second is a polypeptide containing all or a portion of a cancer related antigen.

In some embodiments, the polypeptides encoded by the constructs can be used to enhance the immune response or break self tolerance via an indirect approach. Nucleic acids and polypeptides encoded by them can contain an immunostimulatory agent which would result in stimulation of local or systemic inflammatory responses. An example of inserting peptide epitopes into proteins to make the resulting protein immunogenic is found in WO 95/05849, herein incorporated by reference.

The effect of nucleic acids and the encoded polypeptides can be enhanced with a prime (e.g., a plasmid, viral vector, or bacterial vector or polypeptide) followed by a boost of the same material, to help enhance the immune response (see, e.g., WO 98/56919).

Nucleic acids or polypeptides encoded by the nucleic acids of the invention can be used to monitor tumor development in murine tumor models (Table 2). Mice are immunized with 50–100 ug of a plasmid containing a nucleic acid of the invention one to three times at three week intervals. The plasmid can be delivered in a microparticle or other delivery vehicle, or may be delivered as naked DNA. Then the tumor cells are implanted into mice. At a time post-immunization (varies for individual tumors), tumor development is monitored by assessing tumor growth or activity relative to its initial growth or activity. A determination is made that the tumor has either been slowed or inhibited in its growth or has decreased in activity. The experiment can also be performed by administering the tumor prior to immunization with the CYP1B1-encoding nucleic acid to demonstrate the therapeutic effects of the nucleic acid formulation.

TABLE 2

Tumor/Strain Combinations

| Tumor | Type | Host | MHC |
|---|---|---|---|
| P815 | Mastocytoma | DBA/2 | H-2$^{d}$ |
| Clone M3 (Cloudman S91) | Melanoma | DBA/2 | H-2$^{d}$ |
| CT26.WT | Colon carcinoma | BALB/c | H-2$^{d}$ |
| A20 | B cell lymphoma | BALB/c | H-2$^{d}$ |
| J558 | Plasmacytoma | BALB/c | H-2$^{d}$ |
| EL4 | Thymoma | C57BL/6 | H-2$^{b}$ |
| B16/F10 | Melanoma | C57BL/6 | H-2$^{b}$ |
| 3LL | Lung Carcinoma | C57BL/6 | H-2$^{b}$ |
| Sa1 | Fibrosarcoma | A/J | H-2$^{a(k/d)}$ |

The invention also includes methods of stimulating an immune response in a mammal belonging to a first species by administering to the mammal, e.g., a human or a mouse, a nucleic acid encoding a polypeptide containing a CYP1B1 polypeptide or portion thereof that binds to an MHC class I or class II molecule or immunoglobulin receptor. In these methods, the CYP1B1 polypeptide or MHC-binding portion or immunoglobulin binding portion thereof is identical to a sequence of a naturally occurring CYP1B1 polypeptide of a second species, e.g., a rodent such as a mouse or rat. The nucleic acid used in this method can optionally be a nucleic acid of the invention, e.g., a nucleic acid that lacks sequences found in the untranslated region (UTR) of naturally occurring forms of a CYP1B1 transcript, or a nucleic acid encoding a CYP1B1 with mutations, deletions, insertions, or rearrangements. The nucleic acid can be administered to the mammal naked or via any of the delivery vehicles described herein, e.g., in a microparticle or a polymeric hydrogel matrix. Delivery of a nucleic acid to a first species as described above may result in the development of a herteoclitic immune response in the first species, e.g., an immune response directed to CYP1B1 sequences endogenously produced by the first species. This method could therefore be used to break T cell tolerance and induce a CYP1B1 T cell response in the first species. In these methods, the mammal may have or be at risk of developing a cellular proliferative disorder, e.g., cancer.

Delivery of Nucleic Acids

The compositions of the invention may be used to deliver, into appropriate cells, nucleic acids that express peptides intended to stimulate an immune response against various cancers. An advantage of gene delivery is that the antigenic peptide can be produced inside the target cell itself, where the interaction with a MHC molecules to which the immunogenic peptide binds is kinetically favored. This is in contrast to some vaccine protocols that do not specifically direct antigenic peptides to MHC molecules. Alternatively, the polypeptide can be secreted, resulting in the activation of immune cells such as B cells.

The nucleic acids of the invention can be administered using standard methods, e.g., those described in Donnelly et al., J. Imm. Methods 176:145, 1994, and Vitiello et al., J. Clin. Invest. 95:341, 1995. Nucleic acids of the invention can be injected into subjects in any manner known in the art, e.g., intramuscularly, intravenously, intraarterially, intradermally, intraperitoneally, intranasally, intravaginally, intrarectally or subcutaneously, or they can be introduced into the gastrointestinal tract, the mucosa, or the respiratory tract, e.g., by inhalation of a solution or powder containing microparticles. Alternately, the compositions of the invention may be applied to the skin or electroporated into cells or tissue, either in vitro or in vivo. Alternately, the compositions of the invention may be treated with ultrasound to cause entry into the cells or tissue. Additionally, the compositions of the invention may be administered via a gene gun. Long lasting continuous release of the polypeptides, analogs or nucleic acids of the invention can also be obtained, for example, through the use of osmotic pumps. Administration can be local (e.g., intramuscularly or at the tumor or other site of infection) or systemic.

The nucleic acids can be delivered in a pharmaceutically acceptable carrier such as saline, lipids, liposomes, microparticles, or nanospheres, as hydrogels, as colloidal suspensions, or as powders. They can be naked or associated or complexed with delivery vehicles and/or transfection facilitating agents and delivered using delivery systems known in the art, such as lipids, liposomes, microspheres, microparticles, microcapsules, gold, nanoparticles, polymers, condensing agents, polysaccharides, polyamino acids, dendrimers, saponins, adsorption enhancing materials, membrane permeabilizing agents such as streptolysin O, or fatty acids.

Examples of hydrogel networks are described in U.S. Ser. No. 60/270,256, filed Feb. 20, 2001.

The nucleic acids can include nuclear localization signals that promote the translocation of the nucleic acid to the nucleus. For example, a nucleic acid can include a sequence of nucleotides that is bound by a DNA binding protein, such as a transcription factor. In another example, a peptide based nuclear localization signal can be provided with a nucleic acid of the invention, to thereby promote the translocation of the nucleic acid to the nucleus. Examples of useful signals include hnRNPA sequences and the SV40 nuclear localization signal. A nuclear localization peptide sequence can be, for example, mixed with a nucleic acid, conjugated to a nucleic acid, or incorporated in a delivery vehicle such as a liposome or microparticle.

Other standard delivery methods, e.g., biolistic transfer, or ex vivo treatment, can also be used. In ex vivo treatment, e.g., antigen presenting cells (APCs), dendritic cells, peripheral blood mononuclear cells, or bone marrow cells can be obtained from a patient or an appropriate donor and activated ex vivo with the immunogenic compositions, and then returned to the mammal.

Microparticles, including those described in U. S. Pat. No. 5,783,567 and U.S. Ser. No. 60/208,830, filed Jun. 2, 2000, can be used as vehicles for delivering macromolecules such as DNA, RNA, or polypeptides into cells. They may therefore be useful for delivering nucleic acids described herein, optionally with immunostimulatory agents, to a cell of an individual. Microparticles contain macromolecules embedded in a polymeric matrix or enclosed in a shell of polymer. Microparticles act to maintain the integrity of the macromolecule, e.g., by maintaining the enclosed DNA in a nondegraded state. Microparticles can also be used for pulsed delivery of the macromolecule, and for delivery at a specific site or to a specific cell or target cell population such as macrophages, monocytes, or dendritic cells. Microparticle formulations can also be used to activate relevant cell populations such as macrophages, monocytes or dendritic cells.

The polymeric matrix can be a biodegradable co-polymer such as poly-lactic-co-glycolic acid, starch, gelatin, or chitin. Microparticles can be used in particular to maximize delivery of DNA molecules into a subject's phagocytotic cells. Alternatively, the microparticles can be injected or implanted in a tissue, where they form a deposit. As the deposit breaks down, the nucleic acid is released gradually over time and taken up by neighboring cells (including APCS) as free DNA.

Microparticles may also be formulated as described by Mathiowitz et al. (WO 95/24929) and U.S. Pat. Nos. 5,817, 343 and 5,922,253, herein incorporated by reference.

The nucleic acids of the invention can be administered into subjects via lipids, dendrimers, or liposomes using techniques that are well known in the art. For example, liposomes carrying immunogenic polypeptides or nucleic acids encoding immunogenic peptides are known to elicit CTL responses in vivo (Reddy et al., J. Immunol. 148:1585, 1992; Collins et al., J. Immunol. 148:3336–3341, 1992; Fries et al., Proc. Natl. Acad. Sci. USA 89:358, 1992; Nabel et al., Proc. Nat. Acad. Sci. (USA) 89:5157, 1992).

The nucleic acids of the invention can be administered by using Immune Stimulating Complexes (ISCOMS), which are negatively charged cage-like structures 30–40 nm in size formed spontaneously on mixing cholesterol and Quil A (saponin), or saponin alone. The peptides and nucleic acid of the invention can be co-administered with the ISCOMS, or can be administered separately.

Protective immunity has been generated in a variety of experimental models of infection, including toxoplasmosis and Epstein-Barr virus-induced tumors, using ISCOMS as the delivery vehicle for antigens (Mowat et al., Immunology Today 12:383–385, 1991). Doses of antigen as low as 1 Fg encapsulated in ISCOMS have been found to produce class I-mediated CTL responses, where either purified intact HIV-1-IIIB gp 160 envelope glycoprotein or influenza hemagglutinin is the antigen (Takahashi et al. (1990) Nature 344:873).

It is expected that a dosage of approximately 1 to 200 μg of DNA would be administered per kg of body weight per dose. Where the patient is an adult human, vaccination regimens can include, e.g., intramuscular, intravenous, oral, intranasal, intrarectal, or subcutaneous administrations of 10–1000 μg of DNA when delivered in a microparticle or other delivery vehicle, or of about 1–18 mg of naked DNA delivered intramuscularly or intradermally, repeated 1–12 times. Of course, as is well known in the medical arts, dosage for any given patient depends upon many factors, including the patient's size, body surface area, age, sex, and general health; the time and route of administration; the particular compound to be administered; and other drugs being administered concurrently. Determination of optimal dosage is well within the abilities of a pharmacologist of ordinary skill.

Measuring Responses of the Immune System to the Nucleic Acids

The ability of nucleic acids described herein to elicit an immune response can be assayed by using methods for measuring immune responses that are well known in the art. For example, the generation of cytotoxic T cells can be demonstrated in a standard $^{51}$Cr release assay, by measuring intracellular cytokine expression, or by using MHC tetramers. Standard assays, such as ELISA or ELISPOT, can also be used to measure cytokine profiles attributable to T cell activation. T cell proliferation can also be measured using assays such as $^{3}$H-thymidine uptake and other assays known in the art. DTH responses can be measured to assess T cell reactivity. B cell responses can be measured using art recognized assays such as ELISA.

Other methodologies, e.g., digital imaging and cytologic, colposcopic and histological evaluations, can also be used to evaluate the effects of immunogenic peptides, and of nucleic acid encoding the immunogenic peptides, on various types of proliferative disease or cancer.

The following are examples of the practice of the invention. They are not to be construed as limiting the scope of the invention in any way.

EXAMPLES

Example 1

Generation of Human CYP1B1 cDNA Constructs cDNAs encoding human CYP1B1 (SEQ ID NO:2) and CYP1B1-delta3 (SEQ ID NO:38) were each cloned into two different plasmid expression vectors, pCDNA-3 and p3K. The CYP1B1 nucleic acid constructs contained a cDNA coding for a 543 amino acid protein, but lacking all untranslated regions of CYP1B1. The CYP1B1-delta3 construct contained three substitutions, relative to the wild type CYP1B1 of SEQ ID NO:2, at amino acid positions 57, 61 and 365 (amino acids 57: Trp changed to a Cys; amino acid 61: Gly changed to a Glu; amino acid 365: Gly changed to a Trp; see SEQ ID NO:38). The expression vectors pcDNA3-CYPHu1B1, p3k-CYPHu1B1, pcDNA3-CYPHu1B1-delta 3 (pcDNAhu1B1d3), p3K-CYPHu1B1-delta 3 (p3khu1B1d3), and control vectors pcDNA3 and p3K were purified from transformed *Esherichia coli* using Qiagen columns according to the manufacturers instructions (Qiagen, Chatsworth, Calif.). Each construct was sequenced to confirm the introduction of the desired changes.

Additional CYP1B1 constructs were made as follows. Deletions were introduced using PCR, in the background of pcDNA3hu1B1d5. pcDNA3hu1B1d5 encodes a human CYP1B1 protein in which five amino acids are substituted: W57C, G61E, G365W, P379L, and E387K. Upstream primers contained a restriction site and an ATG codon in frame with the subsequent coding sequences. Downstream primers contained the appropriate CYP1B1 coding sequences, followed by the stop codon, and a restriction site for cloning purposes. pcDNA3hu1B1-deltaPPGP encodes the whole CYP1B1 protein, with the exception of amino acids 51 to 54 (PPGP), which were deleted. The pcDNA3hu1B1-F1R1-encoded protein contains a deletion of the first 60 amino acids of CYP1B1, and the pcDNA3hu1B1-F1R2 protein contains the same N-terminal deletion, in addition to the last 82 amino acids of the CYP1B1 protein. The pcDNA3hu1B1-F2R1 protein encompasses a deletion of the first 171 amino acids of CYP1B1, and the pcDNA3hu1B1-F2R2-encoded protein contains the same N-terminal deletion, in addition to the last 82 amino acids of CYP1B1. The pcDNA3hu1B1-F3R1 protein contains a deletion of the first 292 amino acids of CYP1B1, and pcDNA3hu1B1-F3R2 contains the same N-terminal deletion, in addition to the last 82 amino acids of the CYP1B1 protein (FIG. 3). The Double PEP-Padre protein is depicted as SEQ ID NO:41 in FIG. 3.

The HLA-A2/$K^b$ transgenic C57B1/6 mouse line produces a hybrid MHC class I molecule. In this hybrid molecule, the peptide binding domains (alpha1 and alpha2) are derived from the human class I molecule HLA-A*0201, whereas the domain (alpha3) which interacts with the CD8 co-receptor on T cells is derived from the murine class I molecule $K^b$. The resulting animal is capable of responding to immunogens which contain HLA-A2 restricted epitopes and of generating murine cytotoxic T cells (CTLs) that recognize human target cells expressing HLA-A2 (Vitiello et al., J. Exp. Med. 173:1007, 1991).

The experiments described in the following examples demonstrated that: 1) plasmids encoding CYP1B1 were expressed; 2) the CYP1B1 protein was translated; 3) the encoded proteins were processed and the peptides presented on class I receptors in vivo; 4) and the T cell repertoire contained cells capable of recognizing the class I/peptide complex.

Example 2

Immunization of Mice with DNA Expression Vector Encoding Wild Type CYP1B1 Elicits T Cell Immunity in HLA-A2 Transgenic Mice in vivo Groups of at least three 6–8 week old female transgenic mice, expressing the human Class I molecule HLA-A2.1 were immunized with pcDNA3-CYPHu1B1 or pcDNA3 plasmid vectors. 100 micrograms of plasmid DNA was injected into each anterior tibialis muscle. A booster immunization was performed 14 days after the first immunization. Twelve days following the second immunization, splenocytes were harvested.

Figure 4:
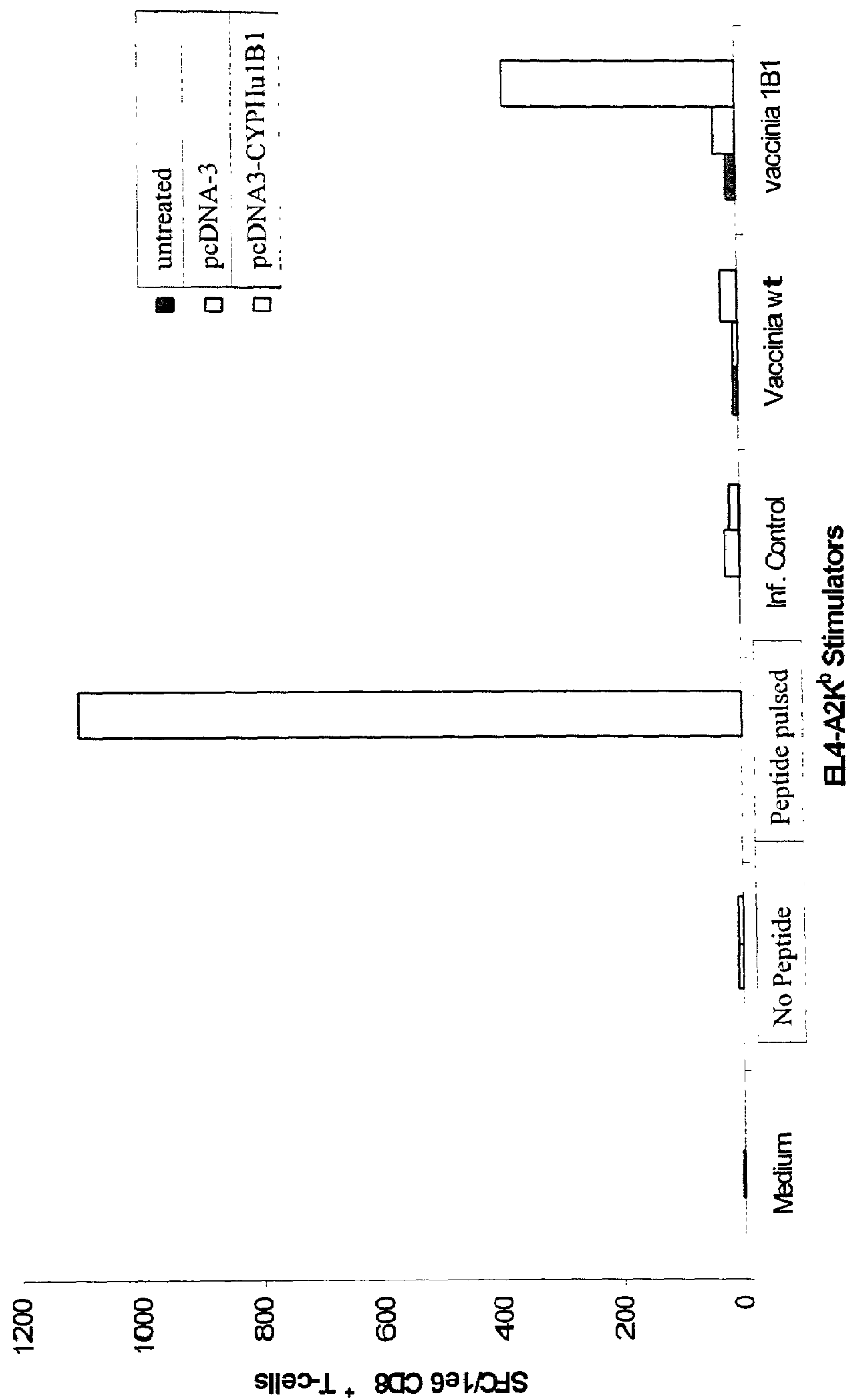
FIG. 4 depicts the generation of CYP1B1 reactive T cells in mice immunized with CYP1B1-expressing vectors.

Single cell suspension of spleens from two to three mice were prepared in RPMI-1640 medium with 10% fetal calf serum and antibiotics. Red blood cells were lysed by incubation of the cells in 0.83% NH4Cl at 4° C. for 10 minutes. After washing, the cells were separated on a CD8 T cell enrichment column according to the manufacturer's protocol (Murine T cell CD8 Subset column kit, R&D System, Minneapolis, Minn.). A mouse interferon-gamma (IFN-g) enzyme-linked immunospot (ELISpot) assay, was used for the detection of individual human CYP1B1 epitope specific CD8+ T cells (Mouse IFN-g ELISpot, R&D Systems). Briefly $1\times10^5$ purified spleen cells were incubated in vitro with equal number of syngeneic EL-4-A2/Kb target cells, which had been pre-pulsed with 10 micromole synthetic HLA-A2.1 binding peptide, FLDPRPLTV (SEQ ID NO:22) or infected with a human CYP1B1-expressing vaccinia vector for 14 hours. After 24 hours of co-culture, T cell activity was determined by performing the ELIspot assay according to the manufacturer's instructions (Mouse IFN-g ELISpot, R&D Systems). The spots, representing the frequency of CYP1B1 reactive T cells, were counted with an automated ELISpot reader system (FIG. 4).

Example 3

A CYP1B1 Variant cDNA Construct Elicits T Cell Immunity in HLA-A2 Transgenic Mice in vivo Groups of at least three 6–8 week old female transgenic mice, expressing the human Class I molecule HLA-A2.1 were immunized with p3K-CYPHu1B1-delta 3 or p3K plasmid vectors. 100 micrograms of plasmid DNA was injected into each anterior tibialis muscle. A booster immunization was performed 14 days after the first immunization. Twelve days following the second immunization, splenocytes were harvested.

Figure 5:
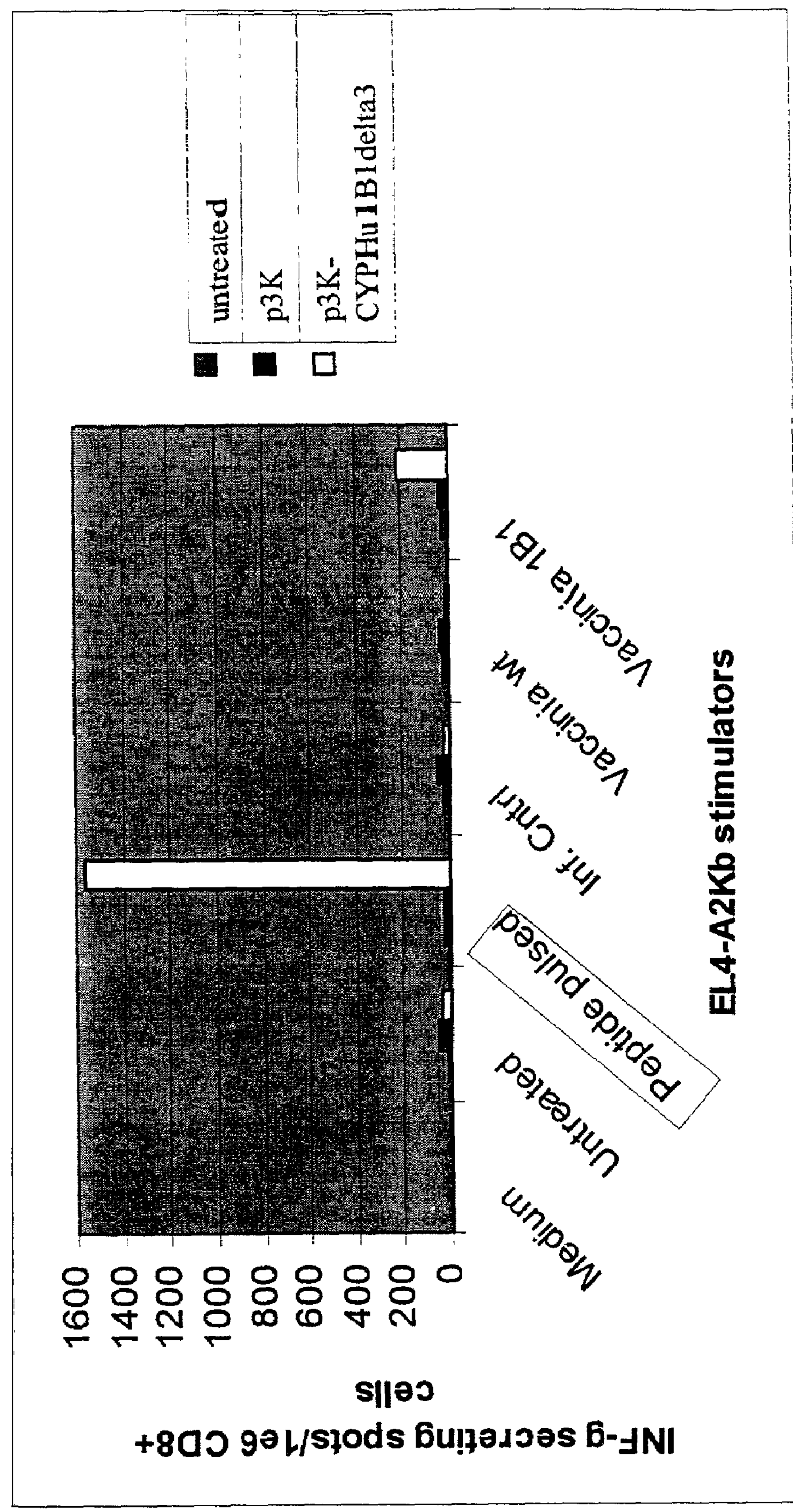
FIG. 5 depicts the generation of CYP1B1 reactive T cells in mice immunized with CYP1B1 variant-expressing vectors.

Single cell suspension of spleens from two to three mice were prepared in RPMI-1640 medium with 10% fetal calf serum and antibiotics. Red blood cells were lysed by incubation of the cells in 0.83% NH4Cl at 4° C. for 10 minutes. After washing the cells were separated on a CD8 T cell enrichment column according to the manufacturer's protocol (Murine T cell CD8 Subset column kit, R&D System, Minneapolis, Minn.). A mouse interferon-gamma (IFN-g) enzyme-linked immunospot (ELISpot) assay, was used for the detection of individual human CYP1B1 epitope specific CD8+ T cells (Mouse IFN-g ELISpot, R&D Systems). Briefly $1\times10^5$ purified spleen cells were incubated in vitro with equal number of syngeneic EL-4-A2/Kb target cells, which had been pre-pulsed with 10 micromole synthetic HLA-A2.1 biding peptide, FLDPRPLTV (SEQ ID NO:22) or infected with a human 1B1 expressing vaccinia vector for 14 hours. After 24 hours of co-culture, T cell activity was determined by performing the ELIspot assay according to the manufacturer's instructions (Mouse IFN-g ELISpot, R&D Systems). The spots, representing the frequency of CYP1B1 reactive T cells, were counted with an automated ELISpot reader system (FIG. 5).

Example 4

Detection of Anti-CYP1B1 Antibodies by Western Blot Analysis

Serum of an animal immunized with a CYP1B1 encoding nucleic acid can be tested for the presence of anti-CYP1B1 antibodies, as follows. Human CYP1B1 microsomes (Gentest, Woburn Mass.) containing 30 ug of microsomal protein are boiled in SDS sample buffer (Boston Bioproducts, Ashland, Mass.) and electrophoretically separated on 10% Tris-HCl acrylamide gels (Bio-Rad, Chicago, Ill.). The gel is electroblotted onto nitrocellulose (Bio-Rad). Non-specific protein binding sites are blocked by incubation of nitrocellulose membranes for 60 minutes at room temperature with 5% non-fat milk in TBST buffer (50 mM Tris [pH 8], 150 mM NaCl, and 0.05% Tween-20). Nitrocellulose filters are incubated with either variable dilutions of immune mouse test serum (e.g., from mice immunized with CYP1B1 peptides or nucleic acid) or a 1:40 to 1:3000 dilution of mouse anti human CYP1B1 443–457 peptide 5D3 mAb in hybridoma culture supernatant diluted in TBST-5% non-fat milk. The membrane is then incubated with a 1:2000 dilution of goat anti-mouse-horseradish peroxidase antibody (Santa Cruz Biotechnology, Santa Cruz, Calif.) diluted in TBST 5% non-fat skim milk. After incubation with each antibody the membrane is washed for five 10 minute periods in TBST. The membrane is developed with ECL reagent (Amersham Pharmacia Biotech, Uppsala, Sweden) to demonstrate the presence of specific protein bands.

Example 5

Electroporation of CYP1B1 Nucleic Acid Constructs

The effect of electroporation on the T cell response induced in a A2/$K^b$ transgenic mouse following a single immunization with p3khu1B1d3 DNA was investigated. Mice were injected with p3khu1B1d3, p3K control vector, or were untreated. Treatment groups were subsequently divided and treated by electroporation or subjected to no further treatment. Electroporation significantly increased the frequency of T cells reactive against EL4-A2/$K^b$ cells either pulsed with CYP190 peptide or infected with recombinant vaccinia virus expressing the native CYP1B1 protein.

Figure 6:
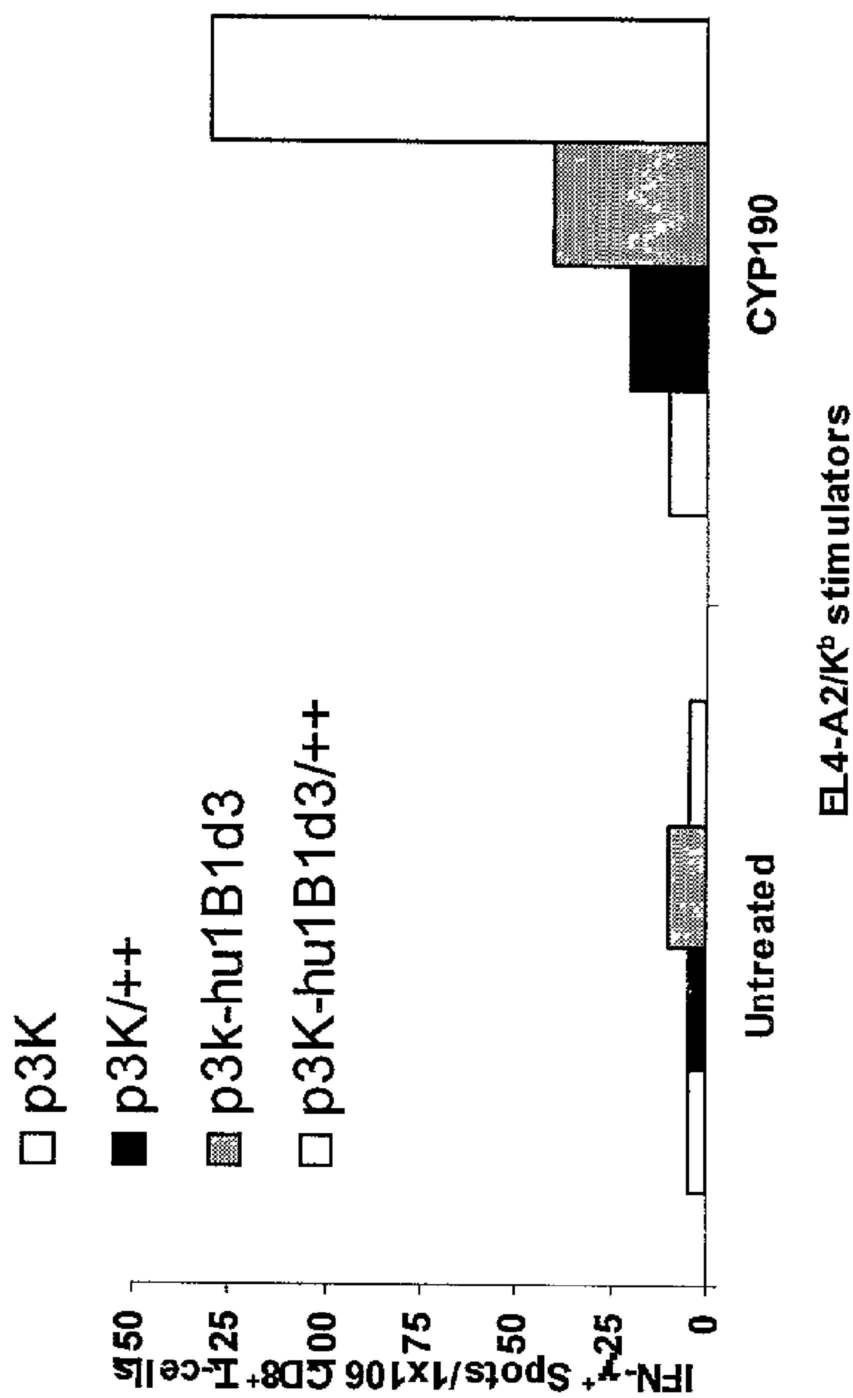
FIG. 6 depicts the generation of CYP1B1 reactive T cells in mice immunized with CYP1B1-expressing vectors followed by electroporation.

FIG. 6 shows that T cell reactivity in HLA-A2/$K^b$ transgenic mice is enhanced by electroporation. Paired groups of mice were immunized once with p3khu1B1d3 DNA, p3K control DNA, and one group per treatment was subjected to electroporation (++) or left untreated. CD8+ T-enriched spleen cells were tested in a direct IFN-γ ELISpot assay against EL4-A2/$K^b$ cells either pulsed with human peptide CYP190(CYP190) or left untreated (untreated). Antigen-specific T-cell frequencies are reported as spot forming cells/10e6 CD8+ T cells.

HLA-A2/$K^b$ transgenic female mice 6–8 weeks of age were used. Plasmid DNA for injection was made with endotoxin-free plasmid purification kits according to the manufacturer's instructions (QIAGEN Inc., Chatsworth, Calif.). A 25 μl volume was injected into the tibialis anterior muscle of each leg for a total dose of 100 μg of DNA. Electroporation was performed on anesthetized mice immediately thereafter by intramuscular insertion of a BTX needle array (Model 532) across the DNA injection site and delivery of pulses (100V, 20msec pulse length×8) by an ElectoSquarePorator Model T820 (Genetronics). Animals were immunized once (two mice per group) and assayed 12 days later. Murine $CD8^+$ T-cell responses to CYP1B1 were analyzed by IFN-γ ELISPOT using a commercial IFN-γ ELISPOT assay kit according to the manufacturer's recommendations (R&D Systems, Minneapolis, Minn.). As effector cells, pooled spleen cells were enriched for $CD8^+$ T-cells (Murine T Cell CD8 Subset column Kit; R&D Systems) and plated in duplicate at $1\times10^5$ cells/well. T-cells were stimulated with $1\times10^5$ EL4-A2/$K^b$ cells/well pulsed with 10 ug/ml peptide or infected with recombinant vaccinia virus or wt vaccinia for 16–18 hours prior to plating (MOI, 10). Plates were incubated for 24 hours, developed, and analyzed by automated image analysis (Zellnet Consulting, Inc., New York, N.Y.). Antigen-specific T-cell frequencies are reported as spot forming cells (SFC)/$1\times10^6$ $CD8^+$ T-cells. The murine thymoma cell line EL4 was obtained from ATCC (Manassas, Va.) and was transfected with the HLA-A2/$K^b$ cDNA inserted into the pSV2neo vector. The human CYP1B1 peptide CYP190(FLDPRPLTV; SEQ ID NO:22) was purchased from Harvard Medical School Biopolymers Laboratory (Boston, Mass.).

Example 6

Hydrogels and Microparticles Containing CYP1B1 Nucleic Acid Constructs

Delivery of CYP1B1d3 DNA by different delivery systems can elicit specific immune responses in HLA-A2/$K^b$ transgenic mice. HLA-A2/$K^b$ transgenic mice were used to evaluate if DNA delivered in a hydrogel could generate an immune response in vivo. Administration of 3 doses of 2% polymeric network, hydrogel formulation or microparticles containing a DNA construct encoding a mutated CYP1B1 cDNA (pcDNA3hu1B1d3) elicited a high frequency of splenic CD8+ T cells with specific reactivity against EL4-A2/$K^b$ cells either pulsed with the HLA-A2 restricted CYP190 peptide or infected with a recombinant vaccinia virus encoding the full length, native huCYP1B1 CDNA. Significant reactivity was not observed against either EL4-A2/$K^b$ cells left untreated or infected with wild type vaccinia virus. Animals immunized with formulated vector (pcDNA 3) DNA did not elicit a response.

Figure 7:
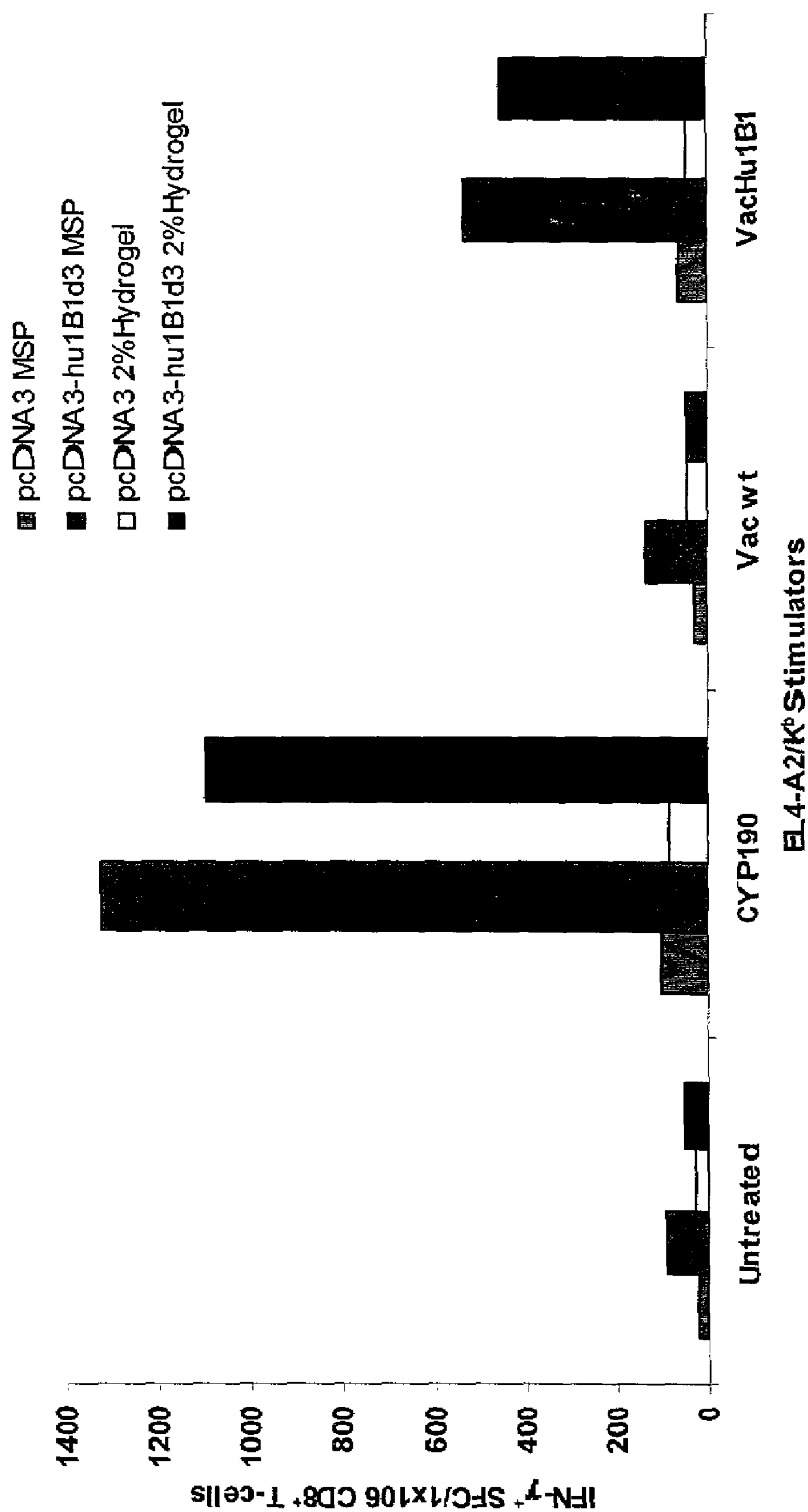
FIG. 7 depicts the generation of CYP1B1 reactive T cells in mice immunized with CYP1B1-expressing vectors contained in polymeric networks.

FIG. 7 shows the induction of a CYP1B1-specific T cell response in A2/$K^b$ transgenic mice by immunization with a CY1B1 DNA/hydrogel formulation. HLA-A2 transgenic mice were immunized 3 times with pcDNA3 DNA or pcDNA3hu1B1d3 delivered in either PLG microparticles or 2% polymeric network hydrogels. CD8+ T-enriched spleen cells were tested in a direct IFN-γ ELISpot assay against EL4-A2/$K^b$ cells either pulsed with human peptide CYP 190(CYP 190) or infected with vaccinia virus encoding CYP1B1 (vacHu1B1). Untreated (untreated) as well as, vaccinia wild type-infected EL4-A2/Kb cells (Vac wt) were included as controls. Antigen-specific T-cell frequencies are reported as spot forming cells (SFC)/$1\times10^6$ $CD8^+$ T-cells.

Female mice 6–8 weeks of age were used in all experiments. Plasmid DNA for injection was made with endotoxin-free plasmid purification kits according to the manufacturer's instructions (QIAGEN Inc., Chatsworth, Calif.). A 25 μl volume was injected into the tibialis anterior muscle of each leg for a total dose of 100 μg of DNA. The plasmid DNA was encapsulated into microparticles or formulated into polymeric network hydrogels as described herein and used for immunization. Animals were immunized three times at biweekly intervals (two mice per group) and assayed 12 days after last immunization. Microparticles were administered in 3 muscles/6 sites per animal: tibialis, calf (soleus muscle),and thigh. Polymeric network hydrogels were injected as 100 ug DNA/100 ul volume; 50 ul per tibialis. Murine $CD8^+$ T-cell responses to CYP1B1 were analyzed by IFN-γ ELISPOT using a commercial IFN-γ ELISPOT assay kit according to the manufacturer's recommendations (R&D Systems, Minneapolis, Minn.). As effector cells, pooled spleen cells were enriched for $CD8^+$ T-cells (Murine T Cell CD8 Subset column Kit; R&D Systems) and plated in duplicate at $1\times10^5$ cells/well. T-cells were stimulated with $1\times10^5$ EL4-A2/$K^b$ cells/well pulsed with 10 ug/ml peptide or infected with recombinant vaccinia virus or wt vaccinia for 16–18 hours prior to plating (MOI, 10). Plates were incubated for 24 hours, developed, and analyzed by automated image analysis (Zellnet Consulting, Inc., New York, N.Y.). Antigen-specific T-cell frequencies are reported as spot forming cells (SFC)/$1\times10^6$ $CD8^+$ T-cells.

Example 7

Microparticles Containing CYP1B1 Nucleic Acid Constructs

HLA-A2/$K^b$ transgenic mice were used to evaluate whether DNA encapsulated in PLG microparticles could generate an immune response in vivo. Administration of two doses of microparticles containing a DNA construct encoding a mutated CYP1B1 cDNA (p3khu1B1d3; ZYC300) elicited T cells with specific reactivity against EL4-A2/$K^b$ cells infected with a recombinant vaccinia virus encoding the full length, native huCYP1B1 cDNA. Significant reactivity was not observed against EL4-A2/$K^b$ cells infected with wild-type vaccinia virus. Neither non-immunized animals nor animals immunized with a vector control showed an IFN-γ response to either stimulator.

Induction of effective anti-tumor immunity involves expansion of an effector T-cell repertoire against self antigens. Data suggesting the effectiveness of CYP1B1 as a therapeutic tumor antigen in this transgenic mouse model would demonstrate that a T-cell response to mouse CYP1B1 self determinants in the context of the endogenous murine class I MHC are elicited following immunization. Mouse and human CYP1B1 share significant sequence homology at the amino acid level. Using the previously described peptide-binding algorithms, a predicted H-$K^b$ binding CYP1B1 peptide was identified as a reagent to test for induction of mouse-specific self responses. This CYP1B1 residue 77–84 (LARRYGDV; SEQ ID NO:42) is shared between human and mouse orthologs. The peptide was included together with the human CYP190 HLA-A2 epitope to test for its ability to detect responses in mice immunized with microparticles containing human CYP1B1 DNA. As shown, a clear response could be detected against this peptide.

Figure 8:
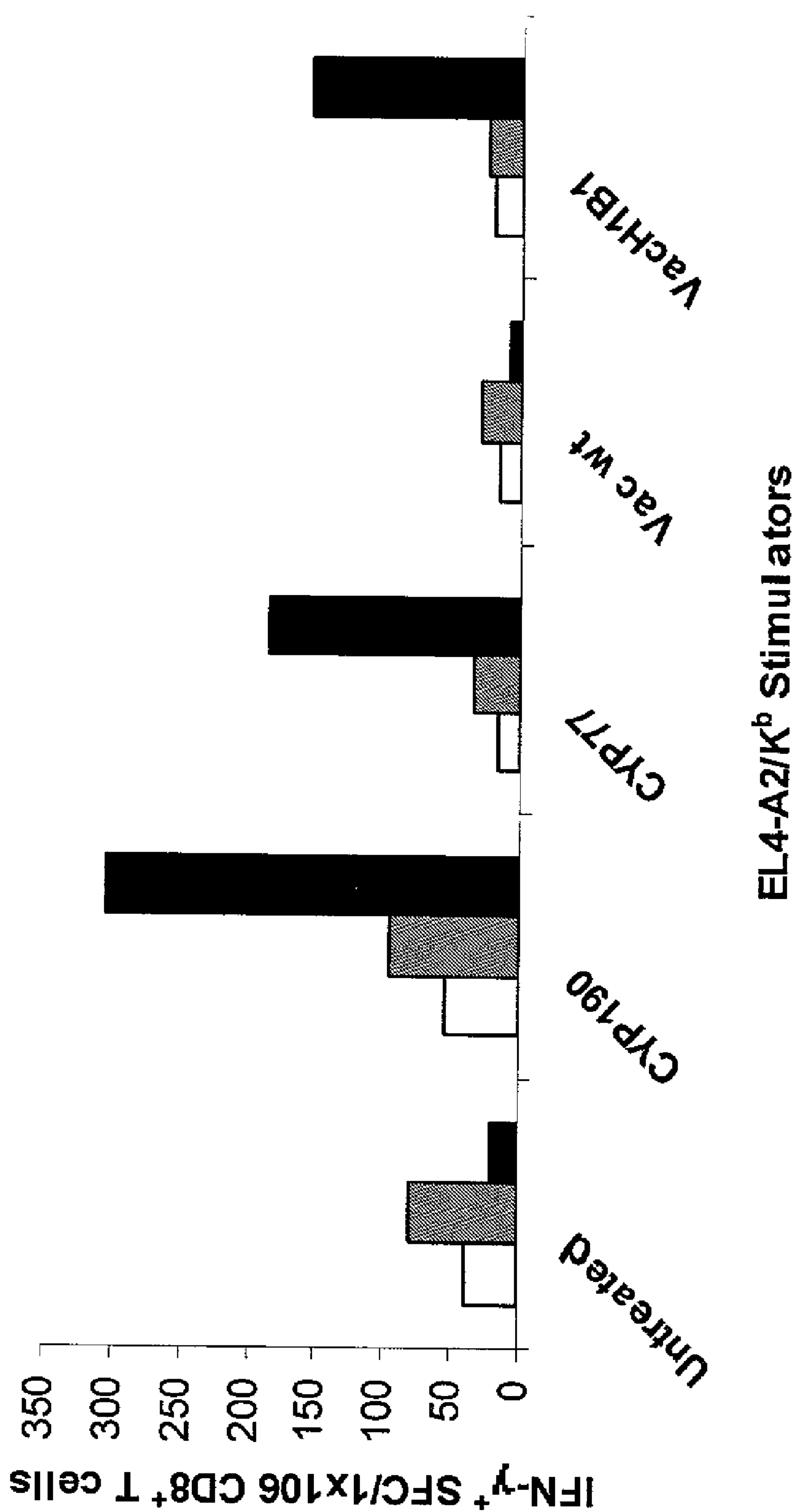
FIG. 8 depicts the generation of CYP1B1 reactive T cells in mice immunized with CYP1B1-expressing vectors contained in microparticles.

FIG. 8 shows that immunization of mice with encapsulated DNA encoding CYP1B1 elicits CYP1B1-specific immune responses in transgenic mice. HLA-A2/$K^b$ transgenic mice were not immunized (left bars), or were immunized twice with microparticles containing p3khu1B1d3 (right bars) or p3k control (center bars). CD8+ enriched spleen cells were tested for immune response against EL4-A2$K^b$ tumor cells in a direct ELISpot assay. Target cells were pulsed with HLA-A2 peptides CYP190, peptide CYP77, or were infected with either CYP1B1-vaccinia (VacHu1B1) or vaccinia wild-type control (Vac Wt).

HLA-A2/$K^b$ transgenic mice were immunized as described above with endotoxin-free plasmid encapsulated in PLG microparticles into the tibialis anterior muscle of each leg for a total dose of 100 μg of DNA. Animals were immunized at two-week intervals and assayed 12 days after the last immunization. Murine $CD8^+$ T cell responses to CYP1B1 were analyzed by IFN-γ ELISpot assay. Effector spleen cells, were enriched for $CD8^+$ T-cells and plated in duplicate at $1\times10^5$ cells/well. T cells were stimulated with $1\times10^5$ EL4-A2$K^b$ cells/well pulsed with 10 μg/ml peptide or infected with recombinant vaccinia virus or wt vaccinia for 16–18 hours prior to plating (MOI, 10). Antigen-specific T-cell frequencies are reported as spot forming cells/$1\times10^6$ $CD8^+$ T-cells. Peptide CYP77 (LARRYGDV; SEQ ID NO:42) is shared between human and mouse CYP1B1 DNA sequence and was purchased from Multiple Peptide Systems (San Diego, Calif.).

Example 8

MHC Class II Responses in Mice Injected With CYP1B1 Nucleic Acid Constructs

Experiments were performed to evaluate whether pcDNA3-hu1B1 encodes a protein that is processed, presented, and can stimulate MHC class II CD4+T cell responses in multiple strains of inbred mice. Class II CD4+T cell responses were detected using an ex-vivo IFN-g Elispot assay with synthetic peptides derived from the CYP1B1 protein.

Three strains of mice (C3H, C57/B16 and Balb/c) were injected (intramuscularly) with 100 μg of pcDNA3-hu1B1. Mice were boosted (intramuscularly) on day 14 with the same dose of pcDNA3-hu1B1. Spleens were harvested on day 27 and IFN-g ELISPOT assays were performed using CD4+T cell enriched splenocytes tested against syngeneic APC pulsed with peptide. In addition, CD4+T cells isolated from naive mice were screened to serve as a negative control. All CD4+T cells were screened against a panel of synthetic CYP1B1 30 mer peptides (see Table 3 for sequences), PHA (positive assay control), and HBV-2(negative assay control).

TABLE 3

Synthetic CYP1B1 Peptides

| 1B1 Peptide # | Sequence | SEQ ID NO |
|---|---|---|
| 2 | RQRRRQLRSAPPGPFAWPLIGNAAAVGQAA | 43 |
| 3 | HLSFARLARRYGDVFQIRLGSCPIVVLNGE | 44 |
| 4 | RAIHQALVQQGSAFADRPAFASFRVVSGGR | 45 |
| 5 | SMAFGHYSEHWKVQRRAAHSMMRNFFTRQP | 46 |
| 6 | RSRQVLEGHVLSEARELVALLVRGSADGAF | 47 |
| 8 | GCRYSHDDPEFRELLSHNEEFGRTVGAGSL | 48 |
| 9 | FGRTVGAGSLVDVMPWLQYFPNPVRTVFRE | 49 |
| 10 | FEQLNRNFSNFILDKFLRHCESLRPGAAPR | 50 |
| 12 | WLLLLFTRYPDVQTRVQAELDQVVGRDRLP | 51 |
| 13 | CMGDQPNLPYVLAFLYEAMRFSSFVPVTIP | 52 |
| 14 | HATTANTSVLGYHIPKDTVVFVNQWSVNHD | 53 |
| 16 | IGEELSKMQLFLFISILAHQCDFRANPNEP | 54 |
| 17 | KSFKVNVTLRESMELLDSAVQNLQAKETCQ | 55 |

Table 4 depicts the results of the above assay for those CYP1B1 peptides that stimulated a response in each of the three mouse strains tested. All reported values IFN-g Spot Forming Cells (SFC)/1,000,000 CD4+ T cells.

TABLE 4

| MHC class II response in C3H, C57/B16, and Balb/c Mice | | | | | | |
|---|---|---|---|---|---|---|
| C3H mice receiving | Media | HBV-2 | PHA | Peptide # 9 | Peptide # 10 | |
| pcDNA3-hu1B1 | 4 | 0 | 78 | 22 | 48 | |
| Naïve C3H mice | 0 | 0 | 148 | 6 | 6 | |
| C57/B16 mice receiving | Media | HBV-2 | PHA | Peptide # 2 | Peptide # 13 | Peptide # 17 |
| pcDNA3-hu1B1 | 0 | 4 | 28 | 44 | 196 | 176 |
| Naïve C57/B16 mice | 0 | 4 | 24 | 8 | 2 | 0 |
| Balb/c mice receiving | Media | HBV-2 | PHA | Peptide # 6 | Peptide # 9 | Peptide # 12 |
| pcDNA3-hu1B1 | 8 | 2 | 158 | 204 | 20 | 28 |
| Naïve Balb/c mice | 0 | 2 | 110 | 2 | 4 | 0 |

Example 9

Immunization with Deletion Constructs of CYP1B

To examine if CYP1B1 can be altered to yield an effective immunogen, a series of CYP1B1 cDNAs were engineered in which progressive portions of the N- and C-termini were deleted. The constructs were cloned into the p3khu1B1d5 background, and hence contained the 5 point mutations of this construct. To verify expression, the constructs were transfected into 293T cells (ATCC) and two days later lysates were generated from the transfected cells. The lysates were analyzed by SDS-PAGE and a Western analysis was performed on the transferred gel. The blot was probed with a monoclonal antibody specific for CYP1B1 and detection was via enhanced chemiluminescence (ECL kit, Amersham). The data from this experiment demonstrated that the variant CYP1B1 proteins were expressed from the deletion constructs.

Figure 9:
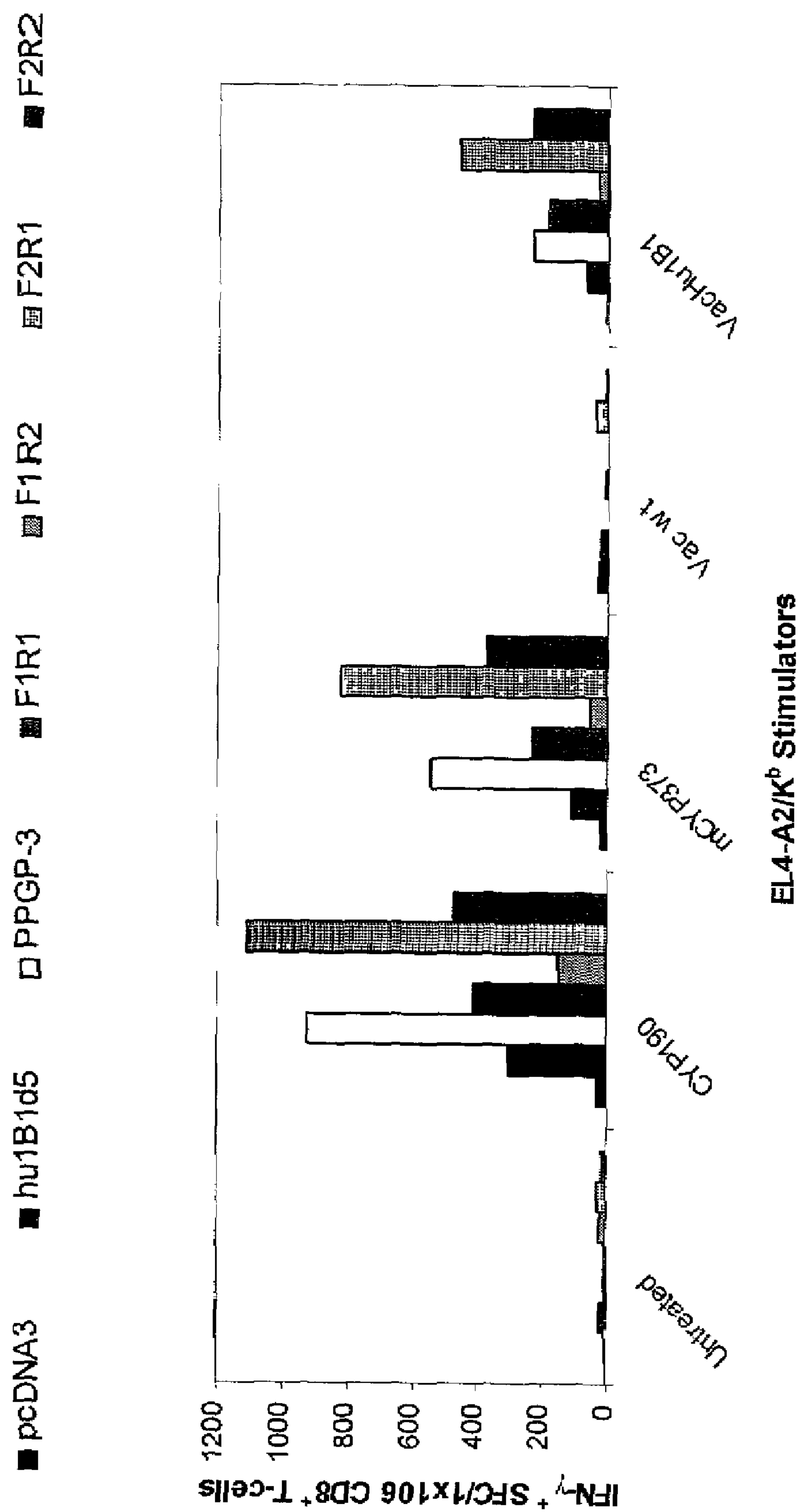
FIG. 9 depicts the generation of CYP1B1 reactive MHC class II restricted T cells in mice immunized with CYP1B1 expressing vectors.

To determine if the constructs induced CYP1B1-specific T cells, HLA-A2/$K^b$ transgenic mice were immunized with DNA constructs encoding the truncated CYP1B1 cDNAs. FIG. 9 shows that CYP1B1-specific T-cells were induced by immunization with truncated CYP1B1 DNA constructs. HLA-A2 transgenic mice were untreated or were immunized with cDNA constructs encoding mutated and/or truncated forms of the CYP1B1 protein. CD8+ T-enriched spleen cells from immunized mice were tested in a direct IFN-g ELISpot assay against EL4-A2/$K^b$ cells either pulsed with human peptide CYP190 (CYP 190), mouse peptide CYP373 (mCYP373), or infected with wild type vaccinia (Vac wt) or vaccinia virus encoding CYP1B1 (VacHu1B1). Untreated as well as vaccinia wild type-infected EL4-A2/$K^b$ cells were included as controls. Antigen-specific T-cell frequencies are reported as spot forming cells (SFC)/$1\times10^6$ $CD8^+$ T-cells. Mice were immunized with DNA encoding the indicated construct.

Female mice 6–8 weeks of age were used in all experiments. Plasmid DNA for injection was made with endotoxin-free plasmid purification kits according to the manufacturer's instructions (QIAGEN Inc., Chatsworth, Calif.). A 25 μl volume was injected into the tibialis anterior muscle of each leg for a total dose of 100 μg of DNA. Animals were immunized at days 0 and 14 (two mice per group) and assayed 12 days after last immunization. Murine $CD8^+$ T-cell responses to CYP1B1 were analyzed by IFN-g ELISPOT using an assay kit according to the manufacturer's recommendations (R&D Systems, Minneapolis, Minn.). As effector cells, pooled spleen cells were enriched for $CD8^+$ T-cells (Murine T Cell CD8 Subset column Kit; R&D Systems) and plated in duplicate at $1\times10^5$ cells/well. T-cells were stimulated with $1\times10^5$ EL4-A2/$K^b$ cells/well pulsed with 10 ug/ml peptide or infected with recombinant vaccinia virus or wt vaccinia for 16–18 hours prior to plating (MOI, 10). Plates were incubated for 24 hours, developed, and analyzed by automated image analysis (Zellnet Consulting, Inc., New York, N.Y.). Antigen-specific T-cell frequencies are reported as spot forming cells (SFC)/$1\times10^6$ $CD8^+$ T-cells. Murine peptide CYP373 (SDQQQPNLPYV; SEQ ID NO:56), was purchased from Multiple Peptide Systems (San Diego, Calif).

OTHER EMBODIMENTS

It is to be understood that while the invention has been described in conjunction with the detailed description thereof, that the foregoing description is intended to illustrate and not limit the scope of the appended claims. Other aspects, advantages, and modifications are within the scope of the following claims.

What is claimed is:

1. A method of inducing an immune response in a mammal having a cancer, the method comprising administering to a mammal having a cancer an effective amount of a composition comprising a microparticle comprising a polymeric matrix or shell and a plasmid expression vector comprising a nucleic acid sequence encoding a polypeptide comprising SEQ ID NQ:38, wherein the nucleic acid sequence is operably linked to an expression control sequence, and wherein the composition is administered intramuscularly or subcutaneously.

2. The method of claim 1, wherein the composition is administered intramuscularly.

3. The method of claim 1, wherein the composition is administered subcutaneously.

4. The method of claim 1, wherein the immune response is a T cell response.

5. The method of claim l, wherein the cancer is a cancer of the bladder, breast, colon, connective tissue, lung, esophagus, skin, lymph node, brain, ovary, stomach, uterus, testis, or prostate.

6. The method of claim 5, wherein the cancer is a cancer of the colon.

7. The method of claim 5, wherein the cancer is a cancer of the lymph node.

8. The method of claim 5, wherein the cancer is a cancer of the ovary.

9. The method of claim 5, wherein the cancer is a cancer of the prostate.

10. The method of claim 1, wherein the polymeric matrix comprises poly lactide-co-glycolide (PLG).

11. The method of claim 1, wherein the microparticle comprises a lipid.

12. The method of claim 10, wherein the microparticle comprises a lipid.

13. A nucleic acid comprising a sequence encoding a polypeptide comprising SEQ ID NO:38.

14. A plasmid expression vector comprising a nucleic acid sequence encoding a polypeptide comprising SEQ ID NO:38, wherein the nucleic acid sequence is operably linked to an expression control sequence.

15. A microparticle comprising a polymeric matrix or shell and the nucleic acid of claim 13.

16. The microparticle of claim 15, wherein the microparticle comprises a polymeric matrix comprising PLG.

17. The microparticle of claim 15, wherein the microparticle comprises a lipid.

18. The microparticle of claim 16, wherein the microparticle comprises a lipid.

19. A microparticle comprising a polymeric matrix or shell and the expression vector of claim 14.

20. The microparticle of claim 19, wherein the microparticle comprises a polymeric matrix comprising PLG.

21. The microparticle of claim 19, wherein the microparticle comprises a lipid.

22. The microparticle of claim 20, wherein the microparticle comprises a lipid.

* * * * *

SEQUENCE LISTING

```
<160> NUMBER OF SEQ ID NOS: 56

<210> SEQ ID NO 1
<211> LENGTH: 5134
<212> TYPE: DNA
<213> ORGANISM: Homo sapiens
<220> FEATURE:
<221> NAME/KEY: CDS
<222> LOCATION: (379)...(2007)

<400> SEQUENCE: 1

actctggagt gggagtggga gtgggagcga gcgcttctgc gactccagtt gtgagagccg      60

caagggcatg ggaattgacg ccactcaccg acccccagtc tcaatctcaa cgctgtgagg     120

aaacctcgac tttgccaggt ccccaagggc agcggggctc ggcgagcgag gcacccttct     180
```

-continued

```
ccgtccccat cccaatccaa gcgctcctgg cactgacgac gccaagagac tcgagtggga    240

gttaaagctt ccagtgaggg cagcaggtgt ccaggccggg cctgcgggtt cctgttgacg    300

tcttgcccta ggcaaaggtc ccagttcctt ctcggagccg gctgtcccgc gccactggaa    360

accgcacctc cccgcagc atg ggc acc agc ctc agc ccg aac gac cct tgg      411
                    Met Gly Thr Ser Leu Ser Pro Asn Asp Pro Trp
                    1               5                   10

ccg cta aac ccg ctg tcc atc cag cag acc acg ctc ctg cta ctc ctg      459
Pro Leu Asn Pro Leu Ser Ile Gln Gln Thr Thr Leu Leu Leu Leu Leu
            15                  20                  25

tcg gtg ctg gcc act gtg cat gtg ggc cag cgg ctg ctg agg caa cgg      507
Ser Val Leu Ala Thr Val His Val Gly Gln Arg Leu Leu Arg Gln Arg
        30                  35                  40

agg cgg cag ctc cgg tcc gcg ccc ccg ggc ccg ttt gcg tgg cca ctg      555
Arg Arg Gln Leu Arg Ser Ala Pro Pro Gly Pro Phe Ala Trp Pro Leu
    45                  50                  55

atc gga aac gcg gcg gcg gtg ggc cag gcg gct cac ctc tcg ttc gct      603
Ile Gly Asn Ala Ala Ala Val Gly Gln Ala Ala His Leu Ser Phe Ala
60                  65                  70                  75

cgc ctg gcg cgg cgc tac ggc gac gtt ttc cag atc cgc ctg ggc agc      651
Arg Leu Ala Arg Arg Tyr Gly Asp Val Phe Gln Ile Arg Leu Gly Ser
                80                  85                  90

tgc ccc ata gtg gtg ctg aat ggc gag cgc gcc atc cac cag gcc ctg      699
Cys Pro Ile Val Val Leu Asn Gly Glu Arg Ala Ile His Gln Ala Leu
            95                  100                 105

gtg cag cag ggc tcg gcc ttc gcc gac cgg ccg gcc ttc gcc tcc ttc      747
Val Gln Gln Gly Ser Ala Phe Ala Asp Arg Pro Ala Phe Ala Ser Phe
        110                 115                 120

cgt gtg gtg tcc ggc ggc cgc agc atg gct ttc ggc cac tac tcg gag      795
Arg Val Val Ser Gly Gly Arg Ser Met Ala Phe Gly His Tyr Ser Glu
    125                 130                 135

cac tgg aag gtg cag cgg cgc gca gcc cac agc atg atg cgc aac ttc      843
His Trp Lys Val Gln Arg Arg Ala Ala His Ser Met Met Arg Asn Phe
140                 145                 150                 155

ttc acg cgc cag ccg cgc agc cgc caa gtc ctc gag ggc cac gtg ctg      891
Phe Thr Arg Gln Pro Arg Ser Arg Gln Val Leu Glu Gly His Val Leu
                160                 165                 170

agc gag gcg cgc gag ctg gtg gcg ctg ctg gtg cgc ggc agc gcg gac      939
Ser Glu Ala Arg Glu Leu Val Ala Leu Leu Val Arg Gly Ser Ala Asp
            175                 180                 185

ggc gcc ttc ctc gac ccg agg ccg ctg acc gtc gtg gcc gtg gcc aac      987
Gly Ala Phe Leu Asp Pro Arg Pro Leu Thr Val Val Ala Val Ala Asn
        190                 195                 200

gtc atg agt gcc gtg tgt ttc ggc tgc cgc tac agc cac gac gac ccc     1035
Val Met Ser Ala Val Cys Phe Gly Cys Arg Tyr Ser His Asp Asp Pro
    205                 210                 215

gag ttc cgt gag ctg ctc agc cac aac gaa gag ttc ggg cgc acg gtg     1083
Glu Phe Arg Glu Leu Leu Ser His Asn Glu Glu Phe Gly Arg Thr Val
220                 225                 230                 235

ggc gcg ggc agc ctg gtg gac gtg atg ccc tgg ctg cag tac ttc ccc     1131
Gly Ala Gly Ser Leu Val Asp Val Met Pro Trp Leu Gln Tyr Phe Pro
                240                 245                 250

aac ccg gtg cgc acc gtt ttc cgc gaa ttc gag cag ctc aac cgc aac     1179
Asn Pro Val Arg Thr Val Phe Arg Glu Phe Glu Gln Leu Asn Arg Asn
            255                 260                 265

ttc agc aac ttc atc ctg gac aag ttc ttg agg cac tgc gaa agc ctt     1227
Phe Ser Asn Phe Ile Leu Asp Lys Phe Leu Arg His Cys Glu Ser Leu
        270                 275                 280

cgg ccc ggg gcc gcc ccc cgc gac atg atg gac gcc ttt atc ctc tct     1275
```

-continued

```
Arg Pro Gly Ala Ala Pro Arg Asp Met Met Asp Ala Phe Ile Leu Ser
    285                 290                 295

gcg gaa aag aag gcg gcc ggg gac tcg cac ggt ggt ggc gcg cgg ctg     1323
Ala Glu Lys Lys Ala Ala Gly Asp Ser His Gly Gly Gly Ala Arg Leu
300                 305                 310                 315

gat ttg gag aac gta ccg gcc act atc act gac atc ttc ggc gcc agc     1371
Asp Leu Glu Asn Val Pro Ala Thr Ile Thr Asp Ile Phe Gly Ala Ser
                320                 325                 330

cag gac acc ctg tcc acc gcg ctg cag tgg ctg ctc ctc ctc ttc acc     1419
Gln Asp Thr Leu Ser Thr Ala Leu Gln Trp Leu Leu Leu Leu Phe Thr
            335                 340                 345

agg tat cct gat gtg cag act cga gtg cag gca gaa ttg gat cag gtc     1467
Arg Tyr Pro Asp Val Gln Thr Arg Val Gln Ala Glu Leu Asp Gln Val
        350                 355                 360

gtg ggg agg gac cgt ctg cct tgt atg ggt gac cag ccc aac ctg ccc     1515
Val Gly Arg Asp Arg Leu Pro Cys Met Gly Asp Gln Pro Asn Leu Pro
    365                 370                 375

tat gtc ctg gcc ttc ctt tat gaa gcc atg cgc ttc tcc agc ttt gtg     1563
Tyr Val Leu Ala Phe Leu Tyr Glu Ala Met Arg Phe Ser Ser Phe Val
380                 385                 390                 395

cct gtc act att cct cat gcc acc act gcc aac acc tct gtc ttg ggc     1611
Pro Val Thr Ile Pro His Ala Thr Thr Ala Asn Thr Ser Val Leu Gly
                400                 405                 410

tac cac att ccc aag gac act gtg gtt ttt gtc aac cag tgg tct gtg     1659
Tyr His Ile Pro Lys Asp Thr Val Val Phe Val Asn Gln Trp Ser Val
            415                 420                 425

aat cat gac cca gtg aag tgg cct aac ccg gag aac ttt gat cca gct     1707
Asn His Asp Pro Val Lys Trp Pro Asn Pro Glu Asn Phe Asp Pro Ala
        430                 435                 440

cga ttc ttg gac aag gat ggc ctc atc aac aag gac ctg acc agc aga     1755
Arg Phe Leu Asp Lys Asp Gly Leu Ile Asn Lys Asp Leu Thr Ser Arg
    445                 450                 455

gtg atg att ttt tca gtg ggc aaa agg cgg tgc att ggc gaa gaa ctt     1803
Val Met Ile Phe Ser Val Gly Lys Arg Arg Cys Ile Gly Glu Glu Leu
460                 465                 470                 475

tct aag atg cag ctt ttt ctc ttc atc tcc atc ctg gct cac cag tgc     1851
Ser Lys Met Gln Leu Phe Leu Phe Ile Ser Ile Leu Ala His Gln Cys
                480                 485                 490

gat ttc agg gcc aac cca aat gag cct gcg aaa atg aat ttc agt tat     1899
Asp Phe Arg Ala Asn Pro Asn Glu Pro Ala Lys Met Asn Phe Ser Tyr
            495                 500                 505

ggt cta acc att aaa ccc aag tca ttt aaa gtc aat gtc act ctc aga     1947
Gly Leu Thr Ile Lys Pro Lys Ser Phe Lys Val Asn Val Thr Leu Arg
        510                 515                 520

gag tcc atg gag ctc ctt gat agt gct gtc caa aat tta caa gcc aag     1995
Glu Ser Met Glu Leu Leu Asp Ser Ala Val Gln Asn Leu Gln Ala Lys
    525                 530                 535

gaa act tgc caa taagaagcaa gaggcaagct gaaattttag aaatattcac         2047
Glu Thr Cys Gln
540

atcttcggag atgaggagta aaattcagtt tttttccagt tcctcttttg tgctgcttct   2107

caattagcgt ttaaggtgag cataaatcaa ctgtccatca ggtgaggtgt gctccatacc   2167

cagcggttct tcatgagtag tgggctatgc aggagcttct gggagatttt tttgagtcaa   2227

agacttaaag ggcccaatga attattatat acatactgca tcttggttat ttctgaaggt   2287

agcattcttt ggagttaaaa tgcacatata gacacataca cccaaacact tacaccaaac   2347

tactgaatga agaagtattt tggtaaccag gccatttttg gtgggaatcc aagattggtc   2407
```

-continued

```
tcccatatgc agaaatagac aaaaagtata ttaaacaaag tttcagagta tattgttgaa   2467
gagacagaga caagtaattt cagtgtaaag tgtgtgattg aaggtgataa gggaaaagat   2527
aaagaccaga aattcccttt tcaccttttc aggaaaataa cttagactct agtatttatg   2587
ggtggattta tccttttgcc ttctggtata cttccttact tttaaggata aatcataaag   2647
tcagttgctc aaaaagaaat caatagttga attagtgagt atagtggggt tccatgagtt   2707
atcatgaatt ttaaagtatg cattattaaa ttgtaaaact ccaaggtgat gttgtacctc   2767
ttttgcttgc caaagtacag aatttgaatt atcagcaaag aaaaaaaaaa aagccagcca   2827
agctttaaat tatgtgacca taatgtactg atttcagtaa gtctcatagg ttaaaaaaaa   2887
aagtcaccaa atagtgtgaa atatattact taactgtccg taagcagtat attagtatta   2947
tcttgttcag gaaaaggttg aataatatat gccttgtgta atattgaaaa ttgaaaagta   3007
caactaacgc aaccaagtgt gctaaaaatg agcttgatta aatcaaccac ctatttttga   3067
catggaaatg aagcagggtt tcttttcttc actcaaattt tggcgaatct caaaattaga   3127
tcctaagatg tgttcttatt tttataacat ctttattgaa attctattta taatacagaa   3187
tcttgttttg aaaataacct aattaatata ttaaaattcc aaattcatgg catgcttaaa   3247
ttttaactaa attttaaagc cattctgatt attgagttcc agttgaagtt agtggaaatc   3307
tgaacattct cctgtggaag gcagagaaat ctaagctgtg tctgcccaat gaataatgga   3367
aaatgccatg aattacctgg atgttctttt tacgaggtga caagagttgg ggacagaact   3427
cccattacaa ctgaccaagt ttctcttcta gatgattttt tgaaagttaa cattaatgcc   3487
tgctttttgg aaagtcagaa tcagaagata gtcttggaag ctgtttggaa aagacagtgg   3547
agatgaggtc agttgtgttt tttaagatgg caattacttt ggtagctggg aaagcataaa   3607
gctcaaatga aatgtatgca ttcacattta gaaaagtgaa ttgaagtttc aagttttaaa   3667
gttcattgca attaaacttc caaagaaagt tctacagtgt cctaagtgct aagtgcttat   3727
tacattttat taagcttttt ggaatctttg taccaaaatt ttaaaaaagg gagtttttga   3787
tagttgtgtg tatgtgtgtg tggggtgggg ggatggtaag agaaaagaga gaaacactga   3847
aaagaaggaa agatggttaa acattttccc actcattctg aattaattaa tttggagcac   3907
aaaattcaaa gcatggacat ttagaagaaa gatgtttggc gtagcagagt taaatctcaa   3967
ataggctatt aaaaaagtct acaacatagc agatctgttt tgtggtttgg aatattaaaa   4027
aacttcatgt aattttattt taaaatttca tagctgtact tcttgaatat aaaaaatcat   4087
gccagtattt ttaaaggcat tagagtcaac tacacaaagc aggcttgccc agtacattta   4147
aattttttgg cacttgccat tccaaaatat tatgccccac caaggctgag acagtgaatt   4207
tgggctgctg tagcctattt ttttagattg agaaatgtgt agctgcaaaa ataatcatga   4267
accaatctgg atgcctcatt atgtcaacca ggtccagatg tgctataatc tgtttttacg   4327
tatgtaggcc cagtcgtcat cagatgcttg cggcaaaaga aagctgtgtt tatatggaag   4387
aaagtaaggt gcttggagtt tacctggctt atttaatatg cttataacct agttaaagaa   4447
aggaaaagaa aacaaaaaac gaatgaaaat aactgaattt ggaggctgga gtaatcagat   4507
tactgcttta atcagaaacc ctcattgtgt ttctaccgga gagagaatgt atttgctgac   4567
aaccattaaa gtcagaagtt ttactccagg ttattgcaat aaagtataat gtttattaaa   4627
tgcttcattt gtatgtcaaa gctttgactc tataagcaaa ttgctttttt ccaaaacaaa   4687
aagatgtctc aggtttgttt tgtgaatttt ctaaaagctt tcatgtccca gaacttagcc   4747
tttacctgtg aagtgttact acagccttaa tattttccta gtagatctat attagatcaa   4807
```

-continued

```
atagttgcat agcagtatat gttaatttgt gtgtttttag ctgtgacaca actgtgtgat   4867

taaaaggtat actttagtag acatttataa ctcaaggata ccttcttatt taatcttttc   4927

ttatttttgt actttatcat gaatgctttt agtgtgtgca taatagctac agtgcatagt   4987

tgtagacaaa gtacattctg gggaaacaac atttatatgt agcctttact gtttgatata   5047

ccaaattaaa aaaaaattgt atctcattac ttatactggg acaccattac caaaataata   5107

aaaatcactt tcataatctt gaaaaaa                                       5134


<210> SEQ ID NO 2
<211> LENGTH: 543
<212> TYPE: PRT
<213> ORGANISM: Homo sapiens

<400> SEQUENCE: 2

Met Gly Thr Ser Leu Ser Pro Asn Asp Pro Trp Pro Leu Asn Pro Leu
 1               5                  10                  15

Ser Ile Gln Gln Thr Thr Leu Leu Leu Leu Leu Ser Val Leu Ala Thr
            20                  25                  30

Val His Val Gly Gln Arg Leu Leu Arg Gln Arg Arg Arg Gln Leu Arg
        35                  40                  45

Ser Ala Pro Pro Gly Pro Phe Ala Trp Pro Leu Ile Gly Asn Ala Ala
    50                  55                  60

Ala Val Gly Gln Ala Ala His Leu Ser Phe Ala Arg Leu Ala Arg Arg
65                  70                  75                  80

Tyr Gly Asp Val Phe Gln Ile Arg Leu Gly Ser Cys Pro Ile Val Val
                85                  90                  95

Leu Asn Gly Glu Arg Ala Ile His Gln Ala Leu Val Gln Gln Gly Ser
            100                 105                 110

Ala Phe Ala Asp Arg Pro Ala Phe Ala Ser Phe Arg Val Val Ser Gly
        115                 120                 125

Gly Arg Ser Met Ala Phe Gly His Tyr Ser Glu His Trp Lys Val Gln
    130                 135                 140

Arg Arg Ala Ala His Ser Met Met Arg Asn Phe Phe Thr Arg Gln Pro
145                 150                 155                 160

Arg Ser Arg Gln Val Leu Glu Gly His Val Leu Ser Glu Ala Arg Glu
                165                 170                 175

Leu Val Ala Leu Leu Val Arg Gly Ser Ala Asp Gly Ala Phe Leu Asp
            180                 185                 190

Pro Arg Pro Leu Thr Val Val Ala Val Ala Asn Val Met Ser Ala Val
        195                 200                 205

Cys Phe Gly Cys Arg Tyr Ser His Asp Asp Pro Glu Phe Arg Glu Leu
    210                 215                 220

Leu Ser His Asn Glu Glu Phe Gly Arg Thr Val Gly Ala Gly Ser Leu
225                 230                 235                 240

Val Asp Val Met Pro Trp Leu Gln Tyr Phe Pro Asn Pro Val Arg Thr
                245                 250                 255

Val Phe Arg Glu Phe Glu Gln Leu Asn Arg Asn Phe Ser Asn Phe Ile
            260                 265                 270

Leu Asp Lys Phe Leu Arg His Cys Glu Ser Leu Arg Pro Gly Ala Ala
        275                 280                 285

Pro Arg Asp Met Met Asp Ala Phe Ile Leu Ser Ala Glu Lys Lys Ala
    290                 295                 300

Ala Gly Asp Ser His Gly Gly Gly Ala Arg Leu Asp Leu Glu Asn Val
```

-continued

```
305                 310                 315                 320

Pro Ala Thr Ile Thr Asp Ile Phe Gly Ala Ser Gln Asp Thr Leu Ser
                325                 330                 335

Thr Ala Leu Gln Trp Leu Leu Leu Leu Phe Thr Arg Tyr Pro Asp Val
            340                 345                 350

Gln Thr Arg Val Gln Ala Glu Leu Asp Gln Val Val Gly Arg Asp Arg
        355                 360                 365

Leu Pro Cys Met Gly Asp Gln Pro Asn Leu Pro Tyr Val Leu Ala Phe
    370                 375                 380

Leu Tyr Glu Ala Met Arg Phe Ser Ser Phe Val Pro Val Thr Ile Pro
385                 390                 395                 400

His Ala Thr Thr Ala Asn Thr Ser Val Leu Gly Tyr His Ile Pro Lys
                405                 410                 415

Asp Thr Val Val Phe Val Asn Gln Trp Ser Val Asn His Asp Pro Val
            420                 425                 430

Lys Trp Pro Asn Pro Glu Asn Phe Asp Pro Ala Arg Phe Leu Asp Lys
        435                 440                 445

Asp Gly Leu Ile Asn Lys Asp Leu Thr Ser Arg Val Met Ile Phe Ser
    450                 455                 460

Val Gly Lys Arg Arg Cys Ile Gly Glu Glu Leu Ser Lys Met Gln Leu
465                 470                 475                 480

Phe Leu Phe Ile Ser Ile Leu Ala His Gln Cys Asp Phe Arg Ala Asn
                485                 490                 495

Pro Asn Glu Pro Ala Lys Met Asn Phe Ser Tyr Gly Leu Thr Ile Lys
            500                 505                 510

Pro Lys Ser Phe Lys Val Asn Val Thr Leu Arg Glu Ser Met Glu Leu
        515                 520                 525

Leu Asp Ser Ala Val Gln Asn Leu Gln Ala Lys Glu Thr Cys Gln
    530                 535                 540


<210> SEQ ID NO 3
<211> LENGTH: 21
<212> TYPE: DNA
<213> ORGANISM: Homo sapiens

<400> SEQUENCE: 3

actccagttg tgagagccgc a                                                21


<210> SEQ ID NO 4
<211> LENGTH: 41
<212> TYPE: DNA
<213> ORGANISM: Homo sapiens

<400> SEQUENCE: 4

gaattgacgc cactcaccga cccccagtct caatctcaac g                          41


<210> SEQ ID NO 5
<211> LENGTH: 61
<212> TYPE: DNA
<213> ORGANISM: Homo sapiens

<400> SEQUENCE: 5

agcaggtgtc caggccgggc ctgcgggttc ctgttgacgt cttgccctag gcaaaggtcc      60

c                                                                      61


<210> SEQ ID NO 6
<211> LENGTH: 101
```

-continued

<212> TYPE: DNA
<213> ORGANISM: Homo sapiens

<400> SEQUENCE: 6
agcaggtgtc caggccgggc ctgcgggttc ctgttgacgt cttgccctag gcaaaggtcc 60
cagttccttc tcggagccgg ctgtcccgcg ccactggaaa c 101

<210> SEQ ID NO 7
<211> LENGTH: 71
<212> TYPE: DNA
<213> ORGANISM: Homo sapiens

<400> SEQUENCE: 7
caagctgaaa ttttagaaat attcacatct tcggagatga ggagtaaaat tcagtttttt 60
tccagttcct c 71

<210> SEQ ID NO 8
<211> LENGTH: 71
<212> TYPE: DNA
<213> ORGANISM: Homo sapiens

<400> SEQUENCE: 8
cttttgtgct gcttctcaat tagcgtttaa ggtgagcata aatcaactgt ccatcaggtg 60
aggtgtgctc c 71

<210> SEQ ID NO 9
<211> LENGTH: 21
<212> TYPE: DNA
<213> ORGANISM: Homo sapiens

<400> SEQUENCE: 9
agtcaaagac ttaaagggcc c 21

<210> SEQ ID NO 10
<211> LENGTH: 2181
<212> TYPE: DNA
<213> ORGANISM: Homo sapiens

<400> SEQUENCE: 10
cttttgtgct gcttctcaat tagcgtttaa ggtgagcata aatcaactgt ccatcaggtg 60
aggtgtgctc catacccagc ggttcttcat gagtagtggg ctatgcagga gcttctggga 120
gatttttttg agtcaaagac ttaaagggcc caatgaatta ttatatacat actgcatctt 180
ggttatttct gaaggtagca ttctttggag ttaaaatgca catatagaca catacaccca 240
aacacttaca ccaaactact gaatgaagaa gtattttggt aaccaggcca tttttggtgg 300
gaatccaaga ttggtctccc atatgcagaa atagacaaaa agtatattaa acaaagtttc 360
agagtatatt gttgaagaga cagagacaag taatttcagt gtaaagtgtg tgattgaagg 420
tgataaggga aaagataaag accagaaatt cccttttcac cttttcagga aaataactta 480
gactctagta tttatgggtg gatttatcct tttgccttct ggtatacttc cttactttta 540
aggataaatc ataaagtcag ttgctcaaaa agaaatcaat agttgaatta gtgagtatag 600
tggggttcca tgagttatca tgaattttaa agtatgcatt attaaattgt aaaactccaa 660
ggtgatgttg tacctctttt gcttgccaaa gtacagaatt tgaattatca gcaaagaaaa 720
aaaaaaaagc cagccaagct ttaaattatg tgaccataat gtactgattt cagtaagtct 780
cataggttaa aaaaaaaagt caccaaatag tgtgaaatat attacttaac tgtccgtaag 840

-continued

```
cagtatatta gtattatctt gttcaggaaa aggttgaata atatatgcct tgtgtaatat    900

tgaaaattga aaagtacaac taacgcaacc aagtgtgcta aaaatgagct tgattaaatc    960

aaccacctat ttttgacatg gaaatgaagc agggtttctt ttcttcactc aaattttggc   1020

gaatctcaaa attagatcct aagatgtgtt cttattttta taacatcttt attgaaattc   1080

tatttataat acagaatctt gttttgaaaa taacctaatt aatatattaa aattccaaat   1140

tcatggcatg cttaaatttt aactaaattt taaagccatt ctgattattg agttccagtt   1200

gaagttagtg gaaatctgaa cattctcctg tggaaggcag agaaatctaa gctgtgtctg   1260

cccaatgaat aatggaaaat gccatgaatt acctggatgt tctttttacg aggtgacaag   1320

agttggggac agaactccca ttacaactga ccaagtttct cttctagatg attttttgaa   1380

agttaacatt aatgcctgct ttttggaaag tcagaatcag aagatagtct tggaagctgt   1440

ttggaaaaga cagtggagat gaggtcagtt gtgtttttta agatggcaat tactttggta   1500

gctgggaaag cataaagctc aaatgaaatg tatgcattca catttagaaa agtgaattga   1560

agtttcaagt tttaaagttc attgcaatta aacttccaaa gaaagttcta cagtgtccta   1620

agtgctaagt gcttattaca ttttattaag ctttttggaa tctttgtacc aaaattttaa   1680

aaaagggagt ttttgatagt tgtgtgtatg tgtgtgtggg gtgggggat ggtaagagaa    1740

aagagagaaa cactgaaaag aaggaaagat ggttaaacat tttcccactc attctgaatt   1800

aattaatttg gagcacaaaa ttcaaagcat ggacatttag aagaaagatg tttggcgtag   1860

cagagttaaa tctcaaatag gctattaaaa aagtctacaa catagcagat ctgttttgtg   1920

gtttggaata ttaaaaaact tcatgtaatt ttattttaaa atttcatagc tgtacttctt   1980

gaatataaaa aatcatgcca gtatttttaa aggcattaga gtcaactaca caaagcaggc   2040

ttgcccagta catttaaatt ttttggcact tgccattcca aaatattatg ccccaccaag   2100

gctgagacag tgaatttggg ctgctgtagc ctattttttt agattgagaa atgtgtagct   2160

gcaaaaataa tcatgaacca a                                              2181
```

<210> SEQ ID NO 11
<211> LENGTH: 476
<212> TYPE: DNA
<213> ORGANISM: Homo sapiens

<400> SEQUENCE: 11

```
tagcattctt tggagttaaa atgcacatat agacacatac acccaaacac ttacaccaaa     60

ctactgaatg aagaagtatt ttggtaacca ggccattttt ggtgggaatc caagattggt    120

ctcccatatg cagaaataga caaaaagtat attaaacaaa gtttcagagt atattgttga    180

agagacagag acaagtaatt tcagtgtaaa gtgtgtgatt gaaggtgata agggaaaaga    240

taaagaccag aaattccctt ttcacctttt caggaaaata acttagactc tagtatttat    300

gggtggattt atccttttgc cttctggtat acttccttac ttttaaggat aaatcataaa    360

gtcagttgct caaaaagaaa tcaatagttg aattagtgag tatagtgggg ttccatgagt    420

tatcatgaat tttaaagtat gcattattaa attgtaaaac tccaaggtga tgttgt        476
```

<210> SEQ ID NO 12
<211> LENGTH: 2721
<212> TYPE: DNA
<213> ORGANISM: Homo sapiens

<400> SEQUENCE: 12

```
ttatatacat actgcatctt ggttatttct gaaggtagca ttctttggag ttaaaatgca     60
```

-continued

```
catatagaca catacaccca aacacttaca ccaaactact gaatgaagaa gtattttggt    120
aaccaggcca tttttggtgg gaatccaaga ttggtctccc atatgcagaa atagacaaaa    180
agtatattaa acaaagtttc agagtatatt gttgaagaga cagagacaag taatttcagt    240
gtaaagtgtg tgattgaagg tgataaggga aaagataaag accagaaatt cccttttcac    300
cttttcagga aaataactta gactctagta tttatgggtg gatttatcct tttgccttct    360
ggtatacttc cttactttta aggataaatc ataaagtcag ttgctcaaaa agaaatcaat    420
agttgaatta gtgagtatag tggggttcca tgagttatca tgaattttaa agtatgcatt    480
attaaattgt aaaactccaa ggtgatgttg tacctctttt gcttgccaaa gtacagaatt    540
tgaattatca gcaaagaaaa aaaaaaaagc cagccaagct ttaaattatg tgaccataat    600
gtactgattt cagtaagtct cataggttaa aaaaaaaagt caccaaatag tgtgaaatat    660
attacttaac tgtccgtaag cagtatatta gtattatctt gttcaggaaa aggttgaata    720
atatatgcct tgtgtaatat tgaaaattga aaagtacaac taacgcaacc aagtgtgcta    780
aaaatgagct tgattaaatc aaccacctat ttttgacatg gaaatgaagc agggtttctt    840
ttcttcactc aaattttggc gaatctcaaa attagatcct aagatgtgtt cttattttta    900
taacatcttt attgaaattc tatttataat acagaatctt gttttgaaaa taacctaatt    960
aatatattaa aattccaaat tcatggcatg cttaaatttt aactaaattt taaagccatt   1020
ctgattattg agttccagtt gaagttagtg gaaatctgaa cattctcctg tggaaggcag   1080
agaaatctaa gctgtgtctg cccaatgaat aatggaaaat gccatgaatt acctggatgt   1140
tctttttacg aggtgacaag agttggggac agaactccca ttacaactga ccaagtttct   1200
cttctagatg attttttgaa agttaacatt aatgcctgct tttggaaag  tcagaatcag   1260
aagatagtct tggaagctgt ttggaaaaga cagtggagat gaggtcagtt gtgtttttta   1320
agatggcaat tactttggta gctgggaaag cataaagctc aaatgaaatg tatgcattca   1380
catttagaaa agtgaattga agtttcaagt tttaaagttc attgcaatta aacttccaaa   1440
gaaagttcta cagtgtccta agtgctaagt gcttattaca ttttattaag ctttttggaa   1500
tctttgtacc aaaattttaa aaaagggagt ttttgatagt tgtgtgtatg tgtgtgtggg   1560
gtggggggat ggtaagagaa aagagagaaa cactgaaaag aaggaaagat ggttaaacat   1620
tttcccactc attctgaatt aattaatttg gagcacaaaa ttcaaagcat ggacatttag   1680
aagaaagatg tttggcgtag cagagttaaa tctcaaatag gctattaaaa aagtctacaa   1740
catagcagat ctgttttgtg gtttggaata ttaaaaaact tcatgtaatt ttattttaaa   1800
atttcatagc tgtacttctt gaatataaaa aatcatgcca gtatttttaa aggcattaga   1860
gtcaactaca caaagcaggc ttgcccagta catttaaatt ttttggcact tgccattcca   1920
aaatattatg ccccaccaag gctgagacag tgaatttggg ctgctgtagc ctattttttt   1980
agattgagaa atgtgtagct gcaaaaataa tcatgaacca atctggatgc ctcattatgt   2040
caaccaggtc cagatgtgct ataatctgtt tttacgtatg taggcccagt cgtcatcaga   2100
tgcttgcggc aaaagaaagc tgtgtttata tggaagaaag taaggtgctt ggagtttacc   2160
tggcttattt aatatgctta taacctagtt aaagaaagga aaagaaaaca aaaaacgaat   2220
gaaaataact gaatttggag gctggagtaa tcagattact gctttaatca gaaaccctca   2280
ttgtgtttct accggagaga gaatgtattt gctgacaacc attaaagtca gaagttttac   2340
tccaggttat tgcaataaag tataatgttt attaaatgct tcatttgtat gtcaaagctt   2400
```

-continued

```
tgactctata agcaaattgc ttttttccaa aacaaaaaga tgtctcaggt ttgttttgtg   2460

aattttctaa aagctttcat gtcccagaac ttagccttta cctgtgaagt gttactacag   2520

ccttaatatt ttcctagtag atctatatta gatcaaatag ttgcatagca gtatatgtta   2580

atttgtgtgt ttttagctgt gacacaactg tgtgattaaa aggtatactt tagtagacat   2640

ttataactca aggatacctt cttatttaat cttttcttat ttttgtactt tatcatgaat   2700

gcttttagtg tgtgcataat a                                             2721
```

<210> SEQ ID NO 13
<211> LENGTH: 461
<212> TYPE: DNA
<213> ORGANISM: Homo sapiens

<400> SEQUENCE: 13

```
tgcttgcggc aaaagaaagc tgtgtttata tggaagaaag taaggtgctt ggagtttacc     60

tggcttattt aatatgctta taacctagtt aaagaaagga aaagaaaaca aaaaacgaat    120

gaaaataact gaatttggag gctggagtaa tcagattact gctttaatca gaaaccctca    180

ttgtgtttct accggagaga gaatgtattt gctgacaacc attaaagtca gaagttttac    240

tccaggttat tgcaataaag tataatgttt attaaatgct tcatttgtat gtcaaagctt    300

tgactctata agcaaattgc ttttttccaa aacaaaaaga tgtctcaggt ttgttttgtg    360

aattttctaa aagctttcat gtcccagaac ttagccttta cctgtgaagt gttactacag    420

ccttaatatt ttcctagtag atctatatta gatcaaatag t                        461
```

<210> SEQ ID NO 14
<211> LENGTH: 451
<212> TYPE: DNA
<213> ORGANISM: Homo sapiens

<400> SEQUENCE: 14

```
tgtgtttata tggaagaaag taaggtgctt ggagtttacc tggcttattt aatatgctta     60

taacctagtt aaagaaagga aaagaaaaca aaaaacgaat gaaaataact gaatttggag    120

gctggagtaa tcagattact gctttaatca gaaaccctca ttgtgtttct accggagaga    180

gaatgtattt gctgacaacc attaaagtca gaagttttac tccaggttat tgcaataaag    240

tataatgttt attaaatgct tcatttgtat gtcaaagctt tgactctata agcaaattgc    300

ttttttccaa aacaaaaaga tgtctcaggt ttgttttgtg aattttctaa aagctttcat    360

gtcccagaac ttagccttta cctgtgaagt gttactacag ccttaatatt ttcctagtag    420

atctatatta gatcaaatag ttgcatagca g                                   451
```

<210> SEQ ID NO 15
<211> LENGTH: 61
<212> TYPE: DNA
<213> ORGANISM: Homo sapiens

<400> SEQUENCE: 15

```
atttgtgtgt ttttagctgt gacacaactg tgtgattaaa aggtatactt tagtagacat     60

t                                                                     61
```

<210> SEQ ID NO 16
<211> LENGTH: 61
<212> TYPE: DNA
<213> ORGANISM: Homo sapiens

<400> SEQUENCE: 16

```
tatcatgaat gcttttagtg tgtgcataat agctacagtg catagttgta gacaaagtac     60

a                                                                     61
```

<210> SEQ ID NO 17
<211> LENGTH: 123
<212> TYPE: DNA
<213> ORGANISM: Homo sapiens

<400> SEQUENCE: 17

```
aacaacattt atatgtagcc tttactgttt gatataccaa attaaaaaaa aattgtatct     60

cattacttat actgggacac cattaccaaa ataataaaaa tcactttcat aatcttgaaa    120

aaa                                                                  123
```

<210> SEQ ID NO 18
<211> LENGTH: 362
<212> TYPE: DNA
<213> ORGANISM: Homo sapiens

<400> SEQUENCE: 18

```
actctggagt gggagtggga gtgggagcga gcgcttctgc gactccagtt gtgagagccg     60

caagggcatg ggaattgacg ccactcaccg acccccagtc tcaatctcaa cgctgtgagg    120

aaacctcgac tttgccaggt ccccaagggc agcggggctc ggcgagcgag gcacccttct    180

ccgtccccat cccaatccaa gcgctcctgg cactgacgac gccaagagac tcgagtggga    240

gttaaagctt ccagtgaggg cagcaggtgt ccaggccggg cctgcgggtt cctgttgacg    300

tcttgcccta ggcaaaggtc ccagttcctt ctcggagccg gctgtcccgc gccactggaa    360

ac                                                                   362
```

<210> SEQ ID NO 19
<211> LENGTH: 3118
<212> TYPE: DNA
<213> ORGANISM: Homo sapiens

<400> SEQUENCE: 19

```
gaagcaagag gcaagctgaa attttagaaa tattcacatc ttcggagatg aggagtaaaa     60

ttcagttttt ttccagttcc tcttttgtgc tgcttctcaa ttagcgttta aggtgagcat    120

aaatcaactg tccatcaggt gaggtgtgct ccatacccag cggttcttca tgagtagtgg    180

gctatgcagg agcttctggg agattttttt gagtcaaaga cttaaagggc ccaatgaatt    240

attatataca tactgcatct tggttatttc tgaaggtagc attctttgga gttaaaatgc    300

acatatagac acatacaccc aaacacttac accaaactac tgaatgaaga agtattttgg    360

taaccaggcc atttttggtg ggaatccaag attggtctcc catatgcaga aatagacaaa    420

aagtatatta aacaaagttt cagagtatat tgttgaagag acagagacaa gtaatttcag    480

tgtaaagtgt gtgattgaag gtgataaggg aaaagataaa gaccagaaat tccctttttca    540

ccttttcagg aaaataactt agactctagt atttatgggt ggatttatcc ttttgccttc    600

tggtatactt ccttactttt aaggataaat cataaagtca gttgctcaaa aagaaatcaa    660

tagttgaatt agtgagtata gtggggttcc atgagttatc atgaatttta aagtatgcat    720

tattaaattg taaaactcca aggtgatgtt gtacctcttt tgcttgccaa agtacagaat    780

ttgaattatc agcaaagaaa aaaaaaaaag ccagccaagc tttaaattat gtgaccataa    840

tgtactgatt tcagtaagtc tcataggtta aaaaaaaaag tcaccaaata gtgtgaaata    900
```

-continued

```
tattacttaa ctgtccgtaa gcagtatatt agtattatct tgttcaggaa aaggttgaat     960
aatatatgcc ttgtgtaata ttgaaaattg aaaagtacaa ctaacgcaac caagtgtgct    1020
aaaaatgagc ttgattaaat caaccaccta tttttgacat ggaaatgaag cagggtttct    1080
tttcttcact caaattttgg cgaatctcaa aattagatcc taagatgtgt tcttattttt    1140
ataacatctt tattgaaatt ctatttataa tacagaatct tgttttgaaa ataacctaat    1200
taatatatta aaattccaaa ttcatggcat gcttaaattt taactaaatt ttaaagccat    1260
tctgattatt gagttccagt tgaagttagt ggaaatctga acattctcct gtggaaggca    1320
gagaaatcta agctgtgtct gcccaatgaa taatggaaaa tgccatgaat tacctggatg    1380
ttctttttac gaggtgacaa gagttgggga cagaactccc attacaactg accaagtttc    1440
tcttctagat gattttttga aagttaacat taatgcctgc tttttggaaa gtcagaatca    1500
gaagatagtc ttggaagctg tttggaaaag acagtggaga tgaggtcagt tgtgtttttt    1560
aagatggcaa ttactttggt agctgggaaa gcataaagct caaatgaaat gtatgcattc    1620
acatttagaa aagtgaattg aagtttcaag ttttaaagtt cattgcaatt aaacttccaa    1680
agaaagttct acagtgtcct aagtgctaag tgcttattac attttattaa gctttttgga    1740
atctttgtac caaaatttta aaaaagggag tttttgatag ttgtgtgtat gtgtgtgtgg    1800
ggtgggggga tggtaagaga aaagagagaa acactgaaaa gaaggaaaga tggttaaaca    1860
ttttcccact cattctgaat taattaattt ggagcacaaa attcaaagca tggacattta    1920
gaagaaagat gtttggcgta gcagagttaa atctcaaata ggctattaaa aaagtctaca    1980
acatagcaga tctgttttgt ggtttggaat attaaaaaac ttcatgtaat tttattttaa    2040
aatttcatag ctgtacttct tgaatataaa aaatcatgcc agtattttta aaggcattag    2100
agtcaactac acaaagcagg cttgcccagt acatttaaat tttttggcac ttgccattcc    2160
aaaatattat gccccaccaa ggctgagaca gtgaatttgg gctgctgtag cctatttttt    2220
tagattgaga aatgtgtagc tgcaaaaata atcatgaacc aatctggatg cctcattatg    2280
tcaaccaggt ccagatgtgc tataatctgt ttttacgtat gtaggcccag tcgtcatcag    2340
atgcttgcgg caaaagaaag ctgtgtttat atggaagaaa gtaaggtgct tggagtttac    2400
ctggcttatt taatatgctt ataacctagt taaagaaagg aaaagaaaac aaaaaacgaa    2460
tgaaaataac tgaatttgga ggctggagta atcagattac tgctttaatc agaaaccctc    2520
attgtgtttc taccggagag agaatgtatt tgctgacaac cattaaagtc agaagtttta    2580
ctccaggtta ttgcaataaa gtataatgtt tattaaatgc ttcatttgta tgtcaaagct    2640
ttgactctat aagcaaattg ctttttttcca aaacaaaaag atgtctcagg tttgttttgt    2700
gaattttcta aaagctttca tgtcccagaa cttagccttt acctgtgaag tgttactaca    2760
gccttaatat tttcctagta gatctatatt agatcaaata gttgcatagc agtatatgtt    2820
aatttgtgtg tttttagctg tgacacaact gtgtgattaa aaggtatact ttagtagaca    2880
tttataactc aaggatacct tcttatttaa tcttttctta tttttgtact ttatcatgaa    2940
tgcttttagt gtgtgcataa tagctacagt gcatagttgt agacaaagta cattctgggg    3000
aaacaacatt tatatgtagc ctttactgtt tgatatacca aattaaaaaa aaattgtatc    3060
tcattactta tactgggaca ccattaccaa aataataaaa atcactttca taatcttg      3118
```

<210> SEQ ID NO 20
<211> LENGTH: 272
<212> TYPE: PRT
<213> ORGANISM: Homo sapiens

<400> SEQUENCE: 20

```
Met Gly Thr Ser Leu Ser Pro Asn Asp Pro Trp Pro Leu Asn Pro Leu
 1               5                  10                  15

Ser Ile Gln Gln Thr Thr Leu Leu Leu Leu Leu Ser Val Leu Ala Thr
            20                  25                  30

Val His Val Gly Gln Arg Leu Leu Arg Gln Arg Arg Arg Gln Leu Arg
        35                  40                  45

Ser Ala Pro Pro Gly Pro Phe Ala Trp Pro Leu Ile Gly Asn Ala Ala
    50                  55                  60

Ala Val Gly Gln Ala Ala His Leu Ser Phe Ala Arg Leu Ala Arg Arg
65                  70                  75                  80

Tyr Gly Asp Val Phe Gln Ile Arg Leu Gly Ser Cys Pro Ile Val Val
                85                  90                  95

Leu Asn Gly Glu Arg Ala Ile His Gln Ala Leu Val Gln Gln Gly Ser
            100                 105                 110

Ala Phe Ala Asp Arg Pro Ala Phe Ala Ser Phe Arg Val Val Ser Gly
        115                 120                 125

Gly Arg Ser Met Ala Phe Gly His Tyr Ser Glu His Trp Lys Val Gln
    130                 135                 140

Arg Arg Ala Ala His Ser Met Met Arg Asn Phe Phe Thr Arg Gln Pro
145                 150                 155                 160

Arg Ser Arg Gln Val Leu Glu Gly His Val Leu Ser Glu Ala Arg Glu
                165                 170                 175

Leu Val Ala Leu Leu Val Arg Gly Ser Ala Asp Gly Ala Phe Leu Asp
            180                 185                 190

Pro Arg Pro Leu Thr Val Val Ala Val Ala Asn Val Met Ser Ala Val
        195                 200                 205

Cys Phe Gly Cys Arg Tyr Ser His Asp Asp Pro Glu Phe Arg Glu Leu
    210                 215                 220

Leu Ser His Asn Glu Glu Phe Gly Arg Thr Val Gly Ala Gly Ser Leu
225                 230                 235                 240

Val Asp Val Met Pro Trp Leu Gln Tyr Phe Pro Asn Pro Val Arg Thr
                245                 250                 255

Val Phe Arg Glu Phe Glu Gln Leu Asn Arg Asn Phe Ser Asn Phe Ile
            260                 265                 270
```

<210> SEQ ID NO 21
<211> LENGTH: 271
<212> TYPE: PRT
<213> ORGANISM: Homo sapiens

<400> SEQUENCE: 21

```
Leu Asp Lys Phe Leu Arg His Cys Glu Ser Leu Arg Pro Gly Ala Ala
 1               5                  10                  15

Pro Arg Asp Met Met Asp Ala Phe Ile Leu Ser Ala Glu Lys Lys Ala
            20                  25                  30

Ala Gly Asp Ser His Gly Gly Gly Ala Arg Leu Asp Leu Glu Asn Val
        35                  40                  45

Pro Ala Thr Ile Thr Asp Ile Phe Gly Ala Ser Gln Asp Thr Leu Ser
    50                  55                  60

Thr Ala Leu Gln Trp Leu Leu Leu Leu Phe Thr Arg Tyr Pro Asp Val
65                  70                  75                  80

Gln Thr Arg Val Gln Ala Glu Leu Asp Gln Val Val Gly Arg Asp Arg
                85                  90                  95
```

```
Leu Pro Cys Met Gly Asp Gln Pro Asn Leu Pro Tyr Val Leu Ala Phe
            100                 105                 110

Leu Tyr Glu Ala Met Arg Phe Ser Ser Phe Val Pro Val Thr Ile Pro
        115                 120                 125

His Ala Thr Thr Ala Asn Thr Ser Val Leu Gly Tyr His Ile Pro Lys
    130                 135                 140

Asp Thr Val Val Phe Val Asn Gln Trp Ser Val Asn His Asp Pro Val
145                 150                 155                 160

Lys Trp Pro Asn Pro Glu Asn Phe Asp Pro Ala Arg Phe Leu Asp Lys
                165                 170                 175

Asp Gly Leu Ile Asn Lys Asp Leu Thr Ser Arg Val Met Ile Phe Ser
            180                 185                 190

Val Gly Lys Arg Arg Cys Ile Gly Glu Glu Leu Ser Lys Met Gln Leu
        195                 200                 205

Phe Leu Phe Ile Ser Ile Leu Ala His Gln Cys Asp Phe Arg Ala Asn
    210                 215                 220

Pro Asn Glu Pro Ala Lys Met Asn Phe Ser Tyr Gly Leu Thr Ile Lys
225                 230                 235                 240

Pro Lys Ser Phe Lys Val Asn Val Thr Leu Arg Glu Ser Met Glu Leu
                245                 250                 255

Leu Asp Ser Ala Val Gln Asn Leu Gln Ala Lys Glu Thr Cys Gln
            260                 265                 270


<210> SEQ ID NO 22
<211> LENGTH: 9
<212> TYPE: PRT
<213> ORGANISM: Homo sapiens

<400> SEQUENCE: 22

Phe Leu Asp Pro Arg Pro Leu Thr Val
 1               5


<210> SEQ ID NO 23
<211> LENGTH: 21
<212> TYPE: PRT
<213> ORGANISM: Homo sapiens

<400> SEQUENCE: 23

Ser Ala Asp Gly Ala Phe Leu Asp Pro Arg Pro Leu Thr Val Val Ala
 1               5                  10                  15

Val Ala Asn Val Met
            20


<210> SEQ ID NO 24
<211> LENGTH: 4
<212> TYPE: PRT
<213> ORGANISM: Homo sapiens

<400> SEQUENCE: 24

Lys Asp Glu Leu
 1


<210> SEQ ID NO 25
<211> LENGTH: 5
<212> TYPE: PRT
<213> ORGANISM: Homo sapiens

<400> SEQUENCE: 25

Lys Phe Glu Arg Gln
```

```
 1               5


<210> SEQ ID NO 26
<211> LENGTH: 5
<212> TYPE: PRT
<213> ORGANISM: Homo sapiens

<400> SEQUENCE: 26

Gln Arg Glu Phe Lys
 1               5


<210> SEQ ID NO 27
<211> LENGTH: 25
<212> TYPE: PRT
<213> ORGANISM: Homo sapiens

<400> SEQUENCE: 27

Met Ala Ile Ser Gly Val Pro Val Leu Gly Phe Phe Ile Ile Ala Val
 1               5                  10                  15

Leu Met Ser Ala Gln Glu Ser Trp Ala
            20                  25


<210> SEQ ID NO 28
<211> LENGTH: 17
<212> TYPE: PRT
<213> ORGANISM: Homo sapiens

<400> SEQUENCE: 28

Ala Val Lys Arg Pro Ala Ala Thr Lys Lys Ala Gly Gln Ala Lys Lys
 1               5                  10                  15

Lys


<210> SEQ ID NO 29
<211> LENGTH: 17
<212> TYPE: PRT
<213> ORGANISM: Homo sapiens

<400> SEQUENCE: 29

Arg Pro Ala Ala Thr Lys Lys Ala Gly Gln Ala Lys Lys Lys Lys Leu
 1               5                  10                  15

Asp


<210> SEQ ID NO 30
<211> LENGTH: 19
<212> TYPE: PRT
<213> ORGANISM: Homo sapiens

<400> SEQUENCE: 30

Ala Val Lys Arg Pro Ala Ala Thr Lys Lys Ala Gly Gln Ala Lys Lys
 1               5                  10                  15

Lys Leu Asp


<210> SEQ ID NO 31
<211> LENGTH: 549
<212> TYPE: PRT
<213> ORGANISM: Homo sapiens

<400> SEQUENCE: 31

Met Gly Thr Ser Leu Ser Pro Asn Asp Pro Trp Pro Leu Asn Pro Leu
 1               5                  10                  15

Ser Ile Gln Gln Thr Thr Leu Leu Leu Leu Leu Ser Val Leu Ala Thr
            20                  25                  30
```

-continued

```
Val His Val Gly Gln Arg Leu Leu Arg Gln Arg Arg Arg Gln Leu Arg
        35                  40                  45

Ser Ala Phe Ala Cys Pro Leu Ile Glu Asn Ala Ala Ala Val Gly Gln
    50                  55                  60

Ala Ala His Leu Ser Phe Ala Arg Leu Ala Arg Arg Tyr Gly Asp Val
65                  70                  75                  80

Phe Gln Ile Arg Leu Gly Ser Cys Pro Ile Val Val Leu Asn Gly Glu
                85                  90                  95

Arg Ala Ile His Gln Ala Leu Val Gln Gln Gly Ser Ala Phe Ala Asp
            100                 105                 110

Arg Pro Ala Phe Ala Ser Phe Arg Val Val Ser Gly Gly Arg Ser Met
        115                 120                 125

Ala Phe Gly His Tyr Ser Glu His Trp Lys Val Gln Arg Arg Ala Ala
    130                 135                 140

His Ser Met Met Arg Asn Phe Phe Thr Arg Gln Pro Arg Ser Arg Gln
145                 150                 155                 160

Val Leu Glu Gly His Val Leu Ser Glu Ala Arg Glu Leu Val Ala Leu
                165                 170                 175

Leu Val Arg Gly Ser Ala Asp Gly Ala Phe Leu Asp Pro Arg Pro Leu
            180                 185                 190

Thr Val Val Ala Val Ala Asn Val Met Ser Ala Val Cys Phe Gly Cys
        195                 200                 205

Arg Tyr Ser His Asp Asp Pro Glu Phe Arg Glu Leu Leu Ser His Asn
    210                 215                 220

Glu Glu Phe Gly Arg Thr Val Gly Ala Gly Ser Leu Val Asp Val Met
225                 230                 235                 240

Pro Trp Leu Gln Tyr Phe Pro Asn Pro Val Arg Thr Val Phe Arg Glu
                245                 250                 255

Phe Glu Gln Leu Asn Arg Asn Phe Ser Asn Phe Ile Leu Asp Lys Phe
            260                 265                 270

Leu Arg His Cys Glu Ser Leu Arg Pro Gly Ala Ala Pro Arg Asp Met
        275                 280                 285

Met Asp Ala Phe Ile Leu Ser Ala Glu Lys Lys Ala Ala Gly Asp Ser
    290                 295                 300

His Gly Gly Gly Ala Arg Leu Asp Leu Glu Asn Val Pro Ala Thr Ile
305                 310                 315                 320

Thr Asp Ile Phe Gly Ala Ser Gln Asp Thr Leu Ser Thr Ala Leu Gln
                325                 330                 335

Trp Leu Leu Leu Leu Phe Thr Arg Tyr Pro Asp Val Gln Thr Arg Val
            340                 345                 350

Gln Ala Glu Leu Asp Gln Val Val Trp Arg Asp Arg Leu Pro Cys Met
        355                 360                 365

Gly Asp Gln Pro Asn Leu Leu Tyr Val Leu Ala Phe Leu Tyr Lys Ala
    370                 375                 380

Met Arg Phe Ser Ser Phe Val Pro Val Thr Ile Pro His Ala Thr Thr
385                 390                 395                 400

Ala Asn Thr Ser Val Leu Gly Tyr His Ile Pro Lys Asp Thr Val Val
                405                 410                 415

Phe Val Asn Gln Trp Ser Val Asn His Asp Pro Val Lys Trp Pro Asn
            420                 425                 430

Pro Glu Asn Phe Asp Pro Ala Arg Phe Leu Asp Lys Asp Gly Leu Ile
        435                 440                 445
```

-continued

```
Asn Lys Asp Leu Thr Ser Arg Val Met Ile Phe Ser Val Gly Lys Arg
    450                 455                 460

Arg Cys Ile Gly Glu Glu Leu Ser Lys Met Gln Leu Phe Leu Phe Ile
465                 470                 475                 480

Ser Ile Leu Ala His Gln Cys Asp Phe Arg Ala Asn Pro Asn Glu Pro
                485                 490                 495

Ala Lys Met Asn Phe Ser Tyr Gly Leu Thr Ile Lys Pro Lys Ser Phe
            500                 505                 510

Lys Val Asn Val Thr Leu Arg Glu Ser Met Glu Leu Leu Asp Ser Ala
        515                 520                 525

Val Gln Asn Leu Gln Ala Lys Glu Thr Cys Gln Glu Gln Lys Leu Ile
    530                 535                 540

Ser Glu Glu Asp Leu
545
```

<210> SEQ ID NO 32
<211> LENGTH: 494
<212> TYPE: PRT
<213> ORGANISM: Homo sapiens

<400> SEQUENCE: 32

```
Met Gly Asn Ala Ala Ala Val Gly Gln Ala Ala His Leu Ser Phe Ala
 1               5                  10                  15

Arg Leu Ala Arg Arg Tyr Gly Asp Val Phe Gln Ile Arg Leu Gly Ser
            20                  25                  30

Cys Pro Ile Val Val Leu Asn Gly Glu Arg Ala Ile His Gln Ala Leu
        35                  40                  45

Val Gln Gln Gly Ser Ala Phe Ala Asp Arg Pro Ala Phe Ala Ser Phe
    50                  55                  60

Arg Val Val Ser Gly Gly Arg Ser Met Ala Phe Gly His Tyr Ser Glu
65                  70                  75                  80

His Trp Lys Val Gln Arg Arg Ala Ala His Ser Met Met Arg Asn Phe
                85                  90                  95

Phe Thr Arg Gln Pro Arg Ser Arg Gln Val Leu Glu Gly His Val Leu
            100                 105                 110

Ser Glu Ala Arg Glu Leu Val Ala Leu Leu Val Arg Gly Ser Ala Asp
        115                 120                 125

Gly Ala Phe Leu Asp Pro Arg Pro Leu Thr Val Val Ala Val Ala Asn
    130                 135                 140

Val Met Ser Ala Val Cys Phe Gly Cys Arg Tyr Ser His Asp Asp Pro
145                 150                 155                 160

Glu Phe Arg Glu Leu Leu Ser His Asn Glu Glu Phe Gly Arg Thr Val
                165                 170                 175

Gly Ala Gly Ser Leu Val Asp Val Met Pro Trp Leu Gln Tyr Phe Pro
            180                 185                 190

Asn Pro Val Arg Thr Val Phe Arg Glu Phe Glu Gln Leu Asn Arg Asn
        195                 200                 205

Phe Ser Asn Phe Ile Leu Asp Lys Phe Leu Arg His Cys Glu Ser Leu
    210                 215                 220

Arg Pro Gly Ala Ala Pro Arg Asp Met Met Asp Ala Phe Ile Leu Ser
225                 230                 235                 240

Ala Glu Lys Lys Ala Ala Gly Asp Ser His Gly Gly Gly Ala Arg Leu
                245                 250                 255

Asp Leu Glu Asn Val Pro Ala Thr Ile Thr Asp Ile Phe Gly Ala Ser
            260                 265                 270
```

-continued

```
Gln Asp Thr Leu Ser Thr Ala Leu Gln Trp Leu Leu Leu Leu Phe Thr
        275                 280                 285

Arg Tyr Pro Asp Val Gln Thr Arg Val Gln Ala Glu Leu Asp Gln Val
    290                 295                 300

Val Trp Arg Asp Arg Leu Pro Cys Met Gly Asp Gln Pro Asn Leu Leu
305                 310                 315                 320

Tyr Val Leu Ala Phe Leu Tyr Lys Ala Met Arg Phe Ser Ser Phe Val
                325                 330                 335

Pro Val Thr Ile Pro His Ala Thr Thr Ala Asn Thr Ser Val Leu Gly
            340                 345                 350

Tyr His Ile Pro Lys Asp Thr Val Val Phe Val Asn Gln Trp Ser Val
        355                 360                 365

Asn His Asp Pro Val Lys Trp Pro Asn Pro Glu Asn Phe Asp Pro Ala
    370                 375                 380

Arg Phe Leu Asp Lys Asp Gly Leu Ile Asn Lys Asp Leu Thr Ser Arg
385                 390                 395                 400

Val Met Ile Phe Ser Val Gly Lys Arg Arg Cys Ile Gly Glu Glu Leu
                405                 410                 415

Ser Lys Met Gln Leu Phe Leu Phe Ile Ser Ile Leu Ala His Gln Cys
            420                 425                 430

Asp Phe Arg Ala Asn Pro Asn Glu Pro Ala Lys Met Asn Phe Ser Tyr
        435                 440                 445

Gly Leu Thr Ile Lys Pro Lys Ser Phe Lys Val Asn Val Thr Leu Arg
    450                 455                 460

Glu Ser Met Glu Leu Leu Asp Ser Ala Val Gln Asn Leu Gln Ala Lys
465                 470                 475                 480

Glu Thr Cys Gln Glu Gln Lys Leu Ile Ser Glu Glu Asp Leu
                485                 490


<210> SEQ ID NO 33
<211> LENGTH: 412
<212> TYPE: PRT
<213> ORGANISM: Homo sapiens

<400> SEQUENCE: 33

Met Gly Asn Ala Ala Ala Val Gly Gln Ala Ala His Leu Ser Phe Ala
 1               5                  10                  15

Arg Leu Ala Arg Arg Tyr Gly Asp Val Phe Gln Ile Arg Leu Gly Ser
            20                  25                  30

Cys Pro Ile Val Val Leu Asn Gly Glu Arg Ala Ile His Gln Ala Leu
        35                  40                  45

Val Gln Gln Gly Ser Ala Phe Ala Asp Arg Pro Ala Phe Ala Ser Phe
    50                  55                  60

Arg Val Val Ser Gly Gly Arg Ser Met Ala Phe Gly His Tyr Ser Glu
65                  70                  75                  80

His Trp Lys Val Gln Arg Arg Ala Ala His Ser Met Met Arg Asn Phe
                85                  90                  95

Phe Thr Arg Gln Pro Arg Ser Arg Gln Val Leu Glu Gly His Val Leu
            100                 105                 110

Ser Glu Ala Arg Glu Leu Val Ala Leu Leu Val Arg Gly Ser Ala Asp
        115                 120                 125

Gly Ala Phe Leu Asp Pro Arg Pro Leu Thr Val Val Ala Val Ala Asn
    130                 135                 140

Val Met Ser Ala Val Cys Phe Gly Cys Arg Tyr Ser His Asp Asp Pro
```

-continued

```
145                 150                 155                 160

Glu Phe Arg Glu Leu Leu Ser His Asn Glu Glu Phe Gly Arg Thr Val
                165                 170                 175

Gly Ala Gly Ser Leu Val Asp Val Met Pro Trp Leu Gln Tyr Phe Pro
            180                 185                 190

Asn Pro Val Arg Thr Val Phe Arg Glu Phe Glu Gln Leu Asn Arg Asn
        195                 200                 205

Phe Ser Asn Phe Ile Leu Asp Lys Phe Leu Arg His Cys Glu Ser Leu
    210                 215                 220

Arg Pro Gly Ala Ala Pro Arg Asp Met Met Asp Ala Phe Ile Leu Ser
225                 230                 235                 240

Ala Glu Lys Lys Ala Ala Gly Asp Ser His Gly Gly Gly Ala Arg Leu
                245                 250                 255

Asp Leu Glu Asn Val Pro Ala Thr Ile Thr Asp Ile Phe Gly Ala Ser
            260                 265                 270

Gln Asp Thr Leu Ser Thr Ala Leu Gln Trp Leu Leu Leu Leu Phe Thr
        275                 280                 285

Arg Tyr Pro Asp Val Gln Thr Arg Val Gln Ala Glu Leu Asp Gln Val
    290                 295                 300

Val Trp Arg Asp Arg Leu Pro Cys Met Gly Asp Gln Pro Asn Leu Leu
305                 310                 315                 320

Tyr Val Leu Ala Phe Leu Tyr Lys Ala Met Arg Phe Ser Ser Phe Val
                325                 330                 335

Pro Val Thr Ile Pro His Ala Thr Thr Ala Asn Thr Ser Val Leu Gly
            340                 345                 350

Tyr His Ile Pro Lys Asp Thr Val Val Phe Val Asn Gln Trp Ser Val
        355                 360                 365

Asn His Asp Pro Val Lys Trp Pro Asn Pro Glu Asn Phe Asp Pro Ala
    370                 375                 380

Arg Phe Leu Asp Lys Asp Gly Leu Ile Asn Lys Asp Leu Thr Ser Arg
385                 390                 395                 400

Val Met Glu Gln Lys Leu Ile Ser Glu Glu Asp Leu
                405                 410


<210> SEQ ID NO 34
<211> LENGTH: 383
<212> TYPE: PRT
<213> ORGANISM: Homo sapiens

<400> SEQUENCE: 34

Met Ser Glu Ala Arg Glu Leu Val Ala Leu Leu Val Arg Gly Ser Ala
 1               5                  10                  15

Asp Gly Ala Phe Leu Asp Pro Arg Pro Leu Thr Val Val Ala Val Ala
            20                  25                  30

Asn Val Met Ser Ala Val Cys Phe Gly Cys Arg Tyr Ser His Asp Asp
        35                  40                  45

Pro Glu Phe Arg Glu Leu Leu Ser His Asn Glu Glu Phe Gly Arg Thr
    50                  55                  60

Val Gly Ala Gly Ser Leu Val Asp Val Met Pro Trp Leu Gln Tyr Phe
65                  70                  75                  80

Pro Asn Pro Val Arg Thr Val Phe Arg Glu Phe Glu Gln Leu Asn Arg
                85                  90                  95

Asn Phe Ser Asn Phe Ile Leu Asp Lys Phe Leu Arg His Cys Glu Ser
            100                 105                 110
```

-continued

```
Leu Arg Pro Gly Ala Ala Pro Arg Asp Met Met Asp Ala Phe Ile Leu
        115                 120                 125

Ser Ala Glu Lys Lys Ala Ala Gly Asp Ser His Gly Gly Gly Ala Arg
    130                 135                 140

Leu Asp Leu Glu Asn Val Pro Ala Thr Ile Thr Asp Ile Phe Gly Ala
145                 150                 155                 160

Ser Gln Asp Thr Leu Ser Thr Ala Leu Gln Trp Leu Leu Leu Leu Phe
                165                 170                 175

Thr Arg Tyr Pro Asp Val Gln Thr Arg Val Gln Ala Glu Leu Asp Gln
            180                 185                 190

Val Val Trp Arg Asp Arg Leu Pro Cys Met Gly Asp Gln Pro Asn Leu
        195                 200                 205

Leu Tyr Val Leu Ala Phe Leu Tyr Lys Ala Met Arg Phe Ser Ser Phe
    210                 215                 220

Val Pro Val Thr Ile Pro His Ala Thr Thr Ala Asn Thr Ser Val Leu
225                 230                 235                 240

Gly Tyr His Ile Pro Lys Asp Thr Val Val Phe Val Asn Gln Trp Ser
                245                 250                 255

Val Asn His Asp Pro Val Lys Trp Pro Asn Pro Glu Asn Phe Asp Pro
            260                 265                 270

Ala Arg Phe Leu Asp Lys Asp Gly Leu Ile Asn Lys Asp Leu Thr Ser
        275                 280                 285

Arg Val Met Ile Phe Ser Val Gly Lys Arg Arg Cys Ile Gly Glu Glu
    290                 295                 300

Leu Ser Lys Met Gln Leu Phe Leu Phe Ile Ser Ile Leu Ala His Gln
305                 310                 315                 320

Cys Asp Phe Arg Ala Asn Pro Asn Glu Pro Ala Lys Met Asn Phe Ser
                325                 330                 335

Tyr Gly Leu Thr Ile Lys Pro Lys Ser Phe Lys Val Asn Val Thr Leu
            340                 345                 350

Arg Glu Ser Met Glu Leu Leu Asp Ser Ala Val Gln Asn Leu Gln Ala
        355                 360                 365

Lys Glu Thr Cys Gln Glu Gln Lys Leu Ile Ser Glu Glu Asp Leu
    370                 375                 380


<210> SEQ ID NO 35
<211> LENGTH: 301
<212> TYPE: PRT
<213> ORGANISM: Homo sapiens

<400> SEQUENCE: 35

Met Ser Glu Ala Arg Glu Leu Val Ala Leu Leu Val Arg Gly Ser Ala
 1               5                  10                  15

Asp Gly Ala Phe Leu Asp Pro Arg Pro Leu Thr Val Val Ala Val Ala
            20                  25                  30

Asn Val Met Ser Ala Val Cys Phe Gly Cys Arg Tyr Ser His Asp Asp
        35                  40                  45

Pro Glu Phe Arg Glu Leu Leu Ser His Asn Glu Glu Phe Gly Arg Thr
    50                  55                  60

Val Gly Ala Gly Ser Leu Val Asp Val Met Pro Trp Leu Gln Tyr Phe
65                  70                  75                  80

Pro Asn Pro Val Arg Thr Val Phe Arg Glu Phe Glu Gln Leu Asn Arg
                85                  90                  95

Asn Phe Ser Asn Phe Ile Leu Asp Lys Phe Leu Arg His Cys Glu Ser
            100                 105                 110
```

```
Leu Arg Pro Gly Ala Ala Pro Arg Asp Met Met Asp Ala Phe Ile Leu
        115                 120                 125

Ser Ala Glu Lys Lys Ala Ala Gly Asp Ser His Gly Gly Gly Ala Arg
    130                 135                 140

Leu Asp Leu Glu Asn Val Pro Ala Thr Ile Thr Asp Ile Phe Gly Ala
145                 150                 155                 160

Ser Gln Asp Thr Leu Ser Thr Ala Leu Gln Trp Leu Leu Leu Leu Phe
                165                 170                 175

Thr Arg Tyr Pro Asp Val Gln Thr Arg Val Gln Ala Glu Leu Asp Gln
            180                 185                 190

Val Val Trp Arg Asp Arg Leu Pro Cys Met Gly Asp Gln Pro Asn Leu
        195                 200                 205

Leu Tyr Val Leu Ala Phe Leu Tyr Lys Ala Met Arg Phe Ser Ser Phe
    210                 215                 220

Val Pro Val Thr Ile Pro His Ala Thr Thr Ala Asn Thr Ser Val Leu
225                 230                 235                 240

Gly Tyr His Ile Pro Lys Asp Thr Val Val Phe Val Asn Gln Trp Ser
                245                 250                 255

Val Asn His Asp Pro Val Lys Trp Pro Asn Pro Glu Asn Phe Asp Pro
            260                 265                 270

Ala Arg Phe Leu Asp Lys Asp Gly Leu Ile Asn Lys Asp Leu Thr Ser
        275                 280                 285

Arg Val Met Glu Gln Lys Leu Ile Ser Glu Glu Asp Leu
    290                 295                 300


<210> SEQ ID NO 36
<211> LENGTH: 261
<212> TYPE: PRT
<213> ORGANISM: Homo sapiens

<400> SEQUENCE: 36

Met Asp Ala Phe Ile Leu Ser Ala Glu Lys Lys Ala Ala Gly Asp Ser
 1               5                  10                  15

His Gly Gly Gly Ala Arg Leu Asp Leu Glu Asn Val Pro Ala Thr Ile
            20                  25                  30

Thr Asp Ile Phe Gly Ala Ser Gln Asp Thr Leu Ser Thr Ala Leu Gln
        35                  40                  45

Trp Leu Leu Leu Leu Phe Thr Arg Tyr Pro Asp Val Gln Thr Arg Val
    50                  55                  60

Gln Ala Glu Leu Asp Gln Val Val Trp Arg Asp Arg Leu Pro Cys Met
65                  70                  75                  80

Gly Asp Gln Pro Asn Leu Leu Tyr Val Leu Ala Phe Leu Tyr Lys Ala
                85                  90                  95

Met Arg Phe Ser Ser Phe Val Pro Val Thr Ile Pro His Ala Thr Thr
            100                 105                 110

Ala Asn Thr Ser Val Leu Gly Tyr His Ile Pro Lys Asp Thr Val Val
        115                 120                 125

Phe Val Asn Gln Trp Ser Val Asn His Asp Pro Val Lys Trp Pro Asn
    130                 135                 140

Pro Glu Asn Phe Asp Pro Ala Arg Phe Leu Asp Lys Asp Gly Leu Ile
145                 150                 155                 160

Asn Lys Asp Leu Thr Ser Arg Val Met Ile Phe Ser Val Gly Lys Arg
                165                 170                 175

Arg Cys Ile Gly Glu Glu Leu Ser Lys Met Gln Leu Phe Leu Phe Ile
```

-continued

```
            180                 185                 190

Ser Ile Leu Ala His Gln Cys Asp Phe Arg Ala Asn Pro Asn Glu Pro
        195                 200                 205

Ala Lys Met Asn Phe Ser Tyr Gly Leu Thr Ile Lys Pro Lys Ser Phe
    210                 215                 220

Lys Val Asn Val Thr Leu Arg Glu Ser Met Glu Leu Leu Asp Ser Ala
225                 230                 235                 240

Val Gln Asn Leu Gln Ala Lys Glu Thr Cys Gln Glu Gln Lys Leu Ile
                245                 250                 255

Ser Glu Glu Asp Leu
            260


<210> SEQ ID NO 37
<211> LENGTH: 179
<212> TYPE: PRT
<213> ORGANISM: Homo sapiens

<400> SEQUENCE: 37

Met Asp Ala Phe Ile Leu Ser Ala Glu Lys Lys Ala Ala Gly Asp Ser
 1               5                  10                  15

His Gly Gly Gly Ala Arg Leu Asp Leu Glu Asn Val Pro Ala Thr Ile
            20                  25                  30

Thr Asp Ile Phe Gly Ala Ser Gln Asp Thr Leu Ser Thr Ala Leu Gln
        35                  40                  45

Trp Leu Leu Leu Leu Phe Thr Arg Tyr Pro Asp Val Gln Thr Arg Val
    50                  55                  60

Gln Ala Glu Leu Asp Gln Val Val Trp Arg Asp Arg Leu Pro Cys Met
65                  70                  75                  80

Gly Asp Gln Pro Asn Leu Leu Tyr Val Leu Ala Phe Leu Tyr Lys Ala
                85                  90                  95

Met Arg Phe Ser Ser Phe Val Pro Val Thr Ile Pro His Ala Thr Thr
            100                 105                 110

Ala Asn Thr Ser Val Leu Gly Tyr His Ile Pro Lys Asp Thr Val Val
        115                 120                 125

Phe Val Asn Gln Trp Ser Val Asn His Asp Pro Val Lys Trp Pro Asn
    130                 135                 140

Pro Glu Asn Phe Asp Pro Ala Arg Phe Leu Asp Lys Asp Gly Leu Ile
145                 150                 155                 160

Asn Lys Asp Leu Thr Ser Arg Val Met Glu Gln Lys Leu Ile Ser Glu
                165                 170                 175

Glu Asp Leu


<210> SEQ ID NO 38
<211> LENGTH: 543
<212> TYPE: PRT
<213> ORGANISM: Homo sapiens

<400> SEQUENCE: 38

Met Gly Thr Ser Leu Ser Pro Asn Asp Pro Trp Pro Leu Asn Pro Leu
 1               5                  10                  15

Ser Ile Gln Gln Thr Thr Leu Leu Leu Leu Leu Ser Val Leu Ala Thr
            20                  25                  30

Val His Val Gly Gln Arg Leu Leu Arg Gln Arg Arg Arg Gln Leu Arg
        35                  40                  45

Ser Ala Pro Pro Gly Pro Phe Ala Cys Pro Leu Ile Glu Asn Ala Ala
    50                  55                  60
```

```
Ala Val Gly Gln Ala Ala His Leu Ser Phe Ala Arg Leu Ala Arg Arg
65                  70                  75                  80

Tyr Gly Asp Val Phe Gln Ile Arg Leu Gly Ser Cys Pro Ile Val Val
                85                  90                  95

Leu Asn Gly Glu Arg Ala Ile His Gln Ala Leu Val Gln Gln Gly Ser
            100                 105                 110

Ala Phe Ala Asp Arg Pro Ala Phe Ala Ser Phe Arg Val Val Ser Gly
        115                 120                 125

Gly Arg Ser Met Ala Phe Gly His Tyr Ser Glu His Trp Lys Val Gln
    130                 135                 140

Arg Arg Ala Ala His Ser Met Met Arg Asn Phe Phe Thr Arg Gln Pro
145                 150                 155                 160

Arg Ser Arg Gln Val Leu Glu Gly His Val Leu Ser Glu Ala Arg Glu
                165                 170                 175

Leu Val Ala Leu Leu Val Arg Gly Ser Ala Asp Gly Ala Phe Leu Asp
            180                 185                 190

Pro Arg Pro Leu Thr Val Val Ala Val Ala Asn Val Met Ser Ala Val
        195                 200                 205

Cys Phe Gly Cys Arg Tyr Ser His Asp Asp Pro Glu Phe Arg Glu Leu
    210                 215                 220

Leu Ser His Asn Glu Glu Phe Gly Arg Thr Val Gly Ala Gly Ser Leu
225                 230                 235                 240

Val Asp Val Met Pro Trp Leu Gln Tyr Phe Pro Asn Pro Val Arg Thr
                245                 250                 255

Val Phe Arg Glu Phe Glu Gln Leu Asn Arg Asn Phe Ser Asn Phe Ile
            260                 265                 270

Leu Asp Lys Phe Leu Arg His Cys Glu Ser Leu Arg Pro Gly Ala Ala
        275                 280                 285

Pro Arg Asp Met Met Asp Ala Phe Ile Leu Ser Ala Glu Lys Lys Ala
    290                 295                 300

Ala Gly Asp Ser His Gly Gly Gly Ala Arg Leu Asp Leu Glu Asn Val
305                 310                 315                 320

Pro Ala Thr Ile Thr Asp Ile Phe Gly Ala Ser Gln Asp Thr Leu Ser
                325                 330                 335

Thr Ala Leu Gln Trp Leu Leu Leu Leu Phe Thr Arg Tyr Pro Asp Val
            340                 345                 350

Gln Thr Arg Val Gln Ala Glu Leu Asp Gln Val Val Trp Arg Asp Arg
        355                 360                 365

Leu Pro Cys Met Gly Asp Gln Pro Asn Leu Pro Tyr Val Leu Ala Phe
    370                 375                 380

Leu Tyr Glu Ala Met Arg Phe Ser Ser Phe Val Pro Val Thr Ile Pro
385                 390                 395                 400

His Ala Thr Thr Ala Asn Thr Ser Val Leu Gly Tyr His Ile Pro Lys
                405                 410                 415

Asp Thr Val Val Phe Val Asn Gln Trp Ser Val Asn His Asp Pro Val
            420                 425                 430

Lys Trp Pro Asn Pro Glu Asn Phe Asp Pro Ala Arg Phe Leu Asp Lys
        435                 440                 445

Asp Gly Leu Ile Asn Lys Asp Leu Thr Ser Arg Val Met Ile Phe Ser
    450                 455                 460

Val Gly Lys Arg Arg Cys Ile Gly Glu Glu Leu Ser Lys Met Gln Leu
465                 470                 475                 480
```

```
Phe Leu Phe Ile Ser Ile Leu Ala His Gln Cys Asp Phe Arg Ala Asn
                485                 490                 495

Pro Asn Glu Pro Ala Lys Met Asn Phe Ser Tyr Gly Leu Thr Ile Lys
            500                 505                 510

Pro Lys Ser Phe Lys Val Asn Val Thr Leu Arg Glu Ser Met Glu Leu
        515                 520                 525

Leu Asp Ser Ala Val Gln Asn Leu Gln Ala Lys Glu Thr Cys Gln
    530                 535                 540


<210> SEQ ID NO 39
<211> LENGTH: 543
<212> TYPE: PRT
<213> ORGANISM: Homo sapiens

<400> SEQUENCE: 39

Met Gly Thr Ser Leu Ser Pro Asn Asp Pro Trp Pro Leu Asn Pro Leu
 1               5                  10                  15

Ser Ile Gln Gln Thr Thr Leu Leu Leu Leu Leu Ser Val Leu Ala Thr
            20                  25                  30

Val His Val Gly Gln Arg Leu Leu Arg Gln Arg Arg Arg Gln Leu Arg
        35                  40                  45

Ser Ala Pro Pro Gly Pro Phe Ala Cys Pro Leu Ile Glu Asn Ala Ala
    50                  55                  60

Ala Val Gly Gln Ala Ala His Leu Ser Phe Ala Arg Leu Ala Arg Arg
65                  70                  75                  80

Tyr Gly Asp Val Phe Gln Ile Arg Leu Gly Ser Cys Pro Ile Val Val
                85                  90                  95

Leu Asn Gly Glu Arg Ala Ile His Gln Ala Leu Val Gln Gln Gly Ser
            100                 105                 110

Ala Phe Ala Asp Arg Pro Ala Phe Ala Ser Phe Arg Val Val Ser Gly
        115                 120                 125

Gly Arg Ser Met Ala Phe Gly His Tyr Ser Glu His Trp Lys Val Gln
    130                 135                 140

Arg Arg Ala Ala His Ser Met Met Arg Asn Phe Phe Thr Arg Gln Pro
145                 150                 155                 160

Arg Ser Arg Gln Val Leu Glu Gly His Val Leu Ser Glu Ala Arg Glu
                165                 170                 175

Leu Val Ala Leu Leu Val Arg Gly Ser Ala Asp Gly Ala Phe Leu Asp
            180                 185                 190

Pro Arg Pro Leu Thr Val Val Ala Val Ala Asn Val Met Ser Ala Val
        195                 200                 205

Cys Phe Gly Cys Arg Tyr Ser His Asp Asp Pro Glu Phe Arg Glu Leu
    210                 215                 220

Leu Ser His Asn Glu Glu Phe Gly Arg Thr Val Gly Ala Gly Ser Leu
225                 230                 235                 240

Val Asp Val Met Pro Trp Leu Gln Tyr Phe Pro Asn Pro Val Arg Thr
                245                 250                 255

Val Phe Arg Glu Phe Glu Gln Leu Asn Arg Asn Phe Ser Asn Phe Ile
            260                 265                 270

Leu Asp Lys Phe Leu Arg His Cys Glu Ser Leu Arg Pro Gly Ala Ala
        275                 280                 285

Pro Arg Asp Met Met Asp Ala Phe Ile Leu Ser Ala Glu Lys Lys Ala
    290                 295                 300

Ala Gly Asp Ser His Gly Gly Gly Ala Arg Leu Asp Leu Glu Asn Val
305                 310                 315                 320
```

-continued

```
Pro Ala Thr Ile Thr Asp Ile Phe Gly Ala Ser Gln Asp Thr Leu Ser
                325                 330                 335

Thr Ala Leu Gln Trp Leu Leu Leu Leu Phe Thr Arg Tyr Pro Asp Val
            340                 345                 350

Gln Thr Arg Val Gln Ala Glu Leu Asp Gln Val Val Trp Arg Asp Arg
        355                 360                 365

Leu Pro Cys Met Gly Asp Gln Pro Asn Leu Leu Tyr Val Leu Ala Phe
    370                 375                 380

Leu Tyr Lys Ala Met Arg Phe Ser Ser Phe Val Pro Val Thr Ile Pro
385                 390                 395                 400

His Ala Thr Thr Ala Asn Thr Ser Val Leu Gly Tyr His Ile Pro Lys
                405                 410                 415

Asp Thr Val Val Phe Val Asn Gln Trp Ser Val Asn His Asp Pro Val
            420                 425                 430

Lys Trp Pro Asn Pro Glu Asn Phe Asp Pro Ala Arg Phe Leu Asp Lys
        435                 440                 445

Asp Gly Leu Ile Asn Lys Asp Leu Thr Ser Arg Val Met Ile Phe Ser
    450                 455                 460

Val Gly Lys Arg Arg Cys Ile Gly Glu Glu Leu Ser Lys Met Gln Leu
465                 470                 475                 480

Phe Leu Phe Ile Ser Ile Leu Ala His Gln Cys Asp Phe Arg Ala Asn
                485                 490                 495

Pro Asn Glu Pro Ala Lys Met Asn Phe Ser Tyr Gly Leu Thr Ile Lys
            500                 505                 510

Pro Lys Ser Phe Lys Val Asn Val Thr Leu Arg Glu Ser Met Glu Leu
        515                 520                 525

Leu Asp Ser Ala Val Gln Asn Leu Gln Ala Lys Glu Thr Cys Gln
    530                 535                 540


<210> SEQ ID NO 40
<211> LENGTH: 29
<212> TYPE: PRT
<213> ORGANISM: Homo sapiens

<400> SEQUENCE: 40

Met Ala Ile Ser Gly Val Pro Val Leu Gly Phe Phe Ile Ile Ala Met
 1               5                  10                  15

Leu Met Ser Ala Gln Glu Ser Trp Ala Pro Arg Ala Thr
            20                  25


<210> SEQ ID NO 41
<211> LENGTH: 42
<212> TYPE: PRT
<213> ORGANISM: Homo sapiens
<220> FEATURE:
<221> NAME/KEY: VARIANT
<222> LOCATION: 33
<223> OTHER INFORMATION: Xaa = Leu or Glu

<400> SEQUENCE: 41

Met Phe Leu Asp Pro Arg Pro Leu Thr Val Ala Ala Ala Ser Leu Val
 1               5                  10                  15

Asp Val Met Pro Trp Leu Ala Ala Ala Lys Phe Val Ala Ala Trp Thr
            20                  25                  30

Xaa Gln Lys Leu Ile Ser Glu Glu Asp Leu
        35                  40
```

-continued

<210> SEQ ID NO 42
<211> LENGTH: 8
<212> TYPE: PRT
<213> ORGANISM: Homo sapiens

<400> SEQUENCE: 42

```
Leu Ala Arg Arg Tyr Gly Asp Val
 1               5
```

<210> SEQ ID NO 43
<211> LENGTH: 30
<212> TYPE: PRT
<213> ORGANISM: Artificial Sequence
<220> FEATURE:
<223> OTHER INFORMATION: Synthetic CYP1B1 Peptide

<400> SEQUENCE: 43

```
Arg Gln Arg Arg Arg Gln Leu Arg Ser Ala Pro Pro Gly Pro Phe Ala
 1               5                  10                  15

Trp Pro Leu Ile Gly Asn Ala Ala Ala Val Gly Gln Ala Ala
            20                  25                  30
```

<210> SEQ ID NO 44
<211> LENGTH: 30
<212> TYPE: PRT
<213> ORGANISM: Artificial Sequence
<220> FEATURE:
<223> OTHER INFORMATION: Synthetic CYP1B1 Peptide

<400> SEQUENCE: 44

```
His Leu Ser Phe Ala Arg Leu Ala Arg Arg Tyr Gly Asp Val Phe Gln
 1               5                  10                  15

Ile Arg Leu Gly Ser Cys Pro Ile Val Val Leu Asn Gly Glu
            20                  25                  30
```

<210> SEQ ID NO 45
<211> LENGTH: 30
<212> TYPE: PRT
<213> ORGANISM: Artificial Sequence
<220> FEATURE:
<223> OTHER INFORMATION: Synthetic CYP1B1 Peptide

<400> SEQUENCE: 45

```
Arg Ala Ile His Gln Ala Leu Val Gln Gln Gly Ser Ala Phe Ala Asp
 1               5                  10                  15

Arg Pro Ala Phe Ala Ser Phe Arg Val Val Ser Gly Gly Arg
            20                  25                  30
```

<210> SEQ ID NO 46
<211> LENGTH: 30
<212> TYPE: PRT
<213> ORGANISM: Artificial Sequence
<220> FEATURE:
<223> OTHER INFORMATION: Synthetic CYP1B1 Peptide

<400> SEQUENCE: 46

```
Ser Met Ala Phe Gly His Tyr Ser Glu His Trp Lys Val Gln Arg Arg
 1               5                  10                  15

Ala Ala His Ser Met Met Arg Asn Phe Phe Thr Arg Gln Pro
            20                  25                  30
```

<210> SEQ ID NO 47
<211> LENGTH: 30
<212> TYPE: PRT
<213> ORGANISM: Artificial Sequence
<220> FEATURE:
<223> OTHER INFORMATION: Synthetic CYP1B1 Peptide

<400> SEQUENCE: 47

```
Arg Ser Arg Gln Val Leu Glu Gly His Val Leu Ser Glu Ala Arg Glu
 1               5                  10                  15

Leu Val Ala Leu Leu Val Arg Gly Ser Ala Asp Gly Ala Phe
            20                  25                  30
```

<210> SEQ ID NO 48
<211> LENGTH: 30
<212> TYPE: PRT
<213> ORGANISM: Artificial Sequence
<220> FEATURE:
<223> OTHER INFORMATION: Synthetic CYP1B1 Peptide

<400> SEQUENCE: 48

```
Gly Cys Arg Tyr Ser His Asp Asp Pro Glu Phe Arg Glu Leu Leu Ser
 1               5                  10                  15

His Asn Glu Glu Phe Gly Arg Thr Val Gly Ala Gly Ser Leu
            20                  25                  30
```

<210> SEQ ID NO 49
<211> LENGTH: 30
<212> TYPE: PRT
<213> ORGANISM: Artificial Sequence
<220> FEATURE:
<223> OTHER INFORMATION: Synthetic CYP1B1 Peptide

<400> SEQUENCE: 49

```
Phe Gly Arg Thr Val Gly Ala Gly Ser Leu Val Asp Val Met Pro Trp
 1               5                  10                  15

Leu Gln Tyr Phe Pro Asn Pro Val Arg Thr Val Phe Arg Glu
            20                  25                  30
```

<210> SEQ ID NO 50
<211> LENGTH: 30
<212> TYPE: PRT
<213> ORGANISM: Artificial Sequence
<220> FEATURE:
<223> OTHER INFORMATION: Synthetic CYP1B1 Peptide

<400> SEQUENCE: 50

```
Phe Glu Gln Leu Asn Arg Asn Phe Ser Asn Phe Ile Leu Asp Lys Phe
 1               5                  10                  15

Leu Arg His Cys Glu Ser Leu Arg Pro Gly Ala Ala Pro Arg
            20                  25                  30
```

<210> SEQ ID NO 51
<211> LENGTH: 30
<212> TYPE: PRT
<213> ORGANISM: Artificial Sequence
<220> FEATURE:
<223> OTHER INFORMATION: Synthetic CYP1B1 Peptide

<400> SEQUENCE: 51

```
Trp Leu Leu Leu Leu Phe Thr Arg Tyr Pro Asp Val Gln Thr Arg Val
 1               5                  10                  15

Gln Ala Glu Leu Asp Gln Val Val Gly Arg Asp Arg Leu Pro
            20                  25                  30
```

<210> SEQ ID NO 52
<211> LENGTH: 30
<212> TYPE: PRT

<213> ORGANISM: Artificial Sequence
<220> FEATURE:
<223> OTHER INFORMATION: Synthetic CYP1B1 Peptide

<400> SEQUENCE: 52

Cys Met Gly Asp Gln Pro Asn Leu Pro Tyr Val Leu Ala Phe Leu Tyr
1 5 10 15

Glu Ala Met Arg Phe Ser Ser Phe Val Pro Val Thr Ile Pro
20 25 30

<210> SEQ ID NO 53
<211> LENGTH: 30
<212> TYPE: PRT
<213> ORGANISM: Artificial Sequence
<220> FEATURE:
<223> OTHER INFORMATION: Synthetic CYP1B1 Peptide

<400> SEQUENCE: 53

His Ala Thr Thr Ala Asn Thr Ser Val Leu Gly Tyr His Ile Pro Lys
1 5 10 15

Asp Thr Val Val Phe Val Asn Gln Trp Ser Val Asn His Asp
20 25 30

<210> SEQ ID NO 54
<211> LENGTH: 30
<212> TYPE: PRT
<213> ORGANISM: Artificial Sequence
<220> FEATURE:
<223> OTHER INFORMATION: Synthetic CYP1B1 Peptide

<400> SEQUENCE: 54

Ile Gly Glu Glu Leu Ser Lys Met Gln Leu Phe Leu Phe Ile Ser Ile
1 5 10 15

Leu Ala His Gln Cys Asp Phe Arg Ala Asn Pro Asn Glu Pro
20 25 30

<210> SEQ ID NO 55
<211> LENGTH: 30
<212> TYPE: PRT
<213> ORGANISM: Artificial Sequence
<220> FEATURE:
<223> OTHER INFORMATION: Synthetic CYP1B1 Peptide

<400> SEQUENCE: 55

Lys Ser Phe Lys Val Asn Val Thr Leu Arg Glu Ser Met Glu Leu Leu
1 5 10 15

Asp Ser Ala Val Gln Asn Leu Gln Ala Lys Glu Thr Cys Gln
20 25 30

<210> SEQ ID NO 56
<211> LENGTH: 11
<212> TYPE: PRT
<213> ORGANISM: Mus musculus

<400> SEQUENCE: 56

Ser Asp Gln Gln Gln Pro Asn Leu Pro Tyr Val
1 5 10